United States Patent
Yamashita et al.

(10) Patent No.: US 10,793,599 B2
(45) Date of Patent: Oct. 6, 2020

(54) MPHOSPH1-DERIVED PEPTIDE, AND VACCINE INCLUDING SAME

(71) Applicant: OncoTherapy Science, Inc., Kawasaki-shi (JP)

(72) Inventors: Sachiko Yamashita, Kawasaki (JP); Tetsuro Hikichi, Kawasaki (JP)

(73) Assignee: ONCOTHERAPY SCIENCE, INC., Kawasaki-shi, Kanagawa (JP)

( * ) Notice: Subject to any disclaimer, the term of this patent is extended or adjusted under 35 U.S.C. 154(b) by 0 days.

(21) Appl. No.: 15/762,480

(22) PCT Filed: Oct. 6, 2016

(86) PCT No.: PCT/JP2016/079716
§ 371 (c)(1),
(2) Date: Aug. 22, 2018

(87) PCT Pub. No.: WO2017/061522
PCT Pub. Date: Apr. 13, 2017

(65) Prior Publication Data
US 2018/0362581 A1  Dec. 20, 2018

(30) Foreign Application Priority Data
Oct. 8, 2015 (JP) .................... 2015-200220

(51) Int. Cl.
| | |
|---|---|
| *C07K 7/06* | (2006.01) |
| *A61K 35/15* | (2015.01) |
| *A61K 39/00* | (2006.01) |
| *A61K 35/17* | (2015.01) |
| *C12N 1/00* | (2006.01) |
| *C12N 15/09* | (2006.01) |
| *C07K 16/28* | (2006.01) |
| *A61K 48/00* | (2006.01) |
| *C07K 16/18* | (2006.01) |
| *C12N 5/0783* | (2010.01) |
| *G01N 33/50* | (2006.01) |

(52) U.S. Cl.
CPC .............. *C07K 7/06* (2013.01); *A61K 35/15* (2013.01); *A61K 35/17* (2013.01); *A61K 39/00* (2013.01); *A61K 48/00* (2013.01); *C07K 16/18* (2013.01); *C07K 16/28* (2013.01); *C12N 1/00* (2013.01); *C12N 5/0638* (2013.01); *C12N 15/09* (2013.01); *G01N 33/505* (2013.01); *C12N 2502/11* (2013.01); *C12N 2502/1114* (2013.01)

(58) Field of Classification Search
None
See application file for complete search history.

(56) References Cited

U.S. PATENT DOCUMENTS

| | | |
|---|---|---|
| 6,294,663 B1 | 9/2001 | O'Brien |
| 7,745,391 B2 | 6/2010 | Mintz |
| 2004/0028692 A1 | 2/2004 | Zitvogel |
| 2006/0024692 A1 | 2/2006 | Nakamura |
| 2007/0099251 A1 | 5/2007 | Zhang |
| 2008/0207497 A1 | 8/2008 | Ramakrishna |
| 2009/0175844 A1 | 7/2009 | Nakamura |
| 2010/0028373 A1 | 2/2010 | Fujioka |
| 2012/0014996 A1 | 1/2012 | Nakamura |
| 2012/0282286 A1 | 11/2012 | Fujioka |
| 2012/0288514 A1 | 11/2012 | Fujioka |
| 2013/0011933 A1 | 1/2013 | Nakamura |
| 2013/0129759 A1 | 5/2013 | Fujioka |
| 2014/0154281 A1 | 6/2014 | Tsunoda |
| 2015/0231222 A1 | 8/2015 | Fujioka |

FOREIGN PATENT DOCUMENTS

| | | |
|---|---|---|
| JP | 2010-506826 A | 3/2010 |
| JP | 2014-510513 A | 5/2014 |
| RU | 2612905 C2 | 11/2016 |
| RU | 2612905 C2 | 3/2017 |
| WO | 1993/03764 A1 | 3/1993 |
| WO | 2000/073801 A2 | 12/2000 |
| WO | 2003/040165 A2 | 5/2003 |
| WO | 2003/064609 A2 | 8/2003 |
| WO | 2004/031413 A2 | 4/2004 |

(Continued)

OTHER PUBLICATIONS

Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*

(Continued)

*Primary Examiner* — Bridget E Bunner
*Assistant Examiner* — Fozia Hamud
(74) *Attorney, Agent, or Firm* — Kilpatrick Townsend & Stockton LLP

(57) ABSTRACT

The present invention provides MPHOSPH1-derived epitope peptides having the ability to induce cytotoxic T cells. The present invention further provides polynucleotides encoding the peptides, antigen-presenting cells presenting the peptides, and cytotoxic T cells targeting the peptides, as well as methods of inducing the antigen-presenting cells or CTLs. The present invention also provides compositions and pharmaceutical compositions containing them as an active ingredient. Further, the present invention provides methods of treating and/or preventing cancer, and/or preventing post-operative recurrence thereof, using the peptides, polynucleotides, antigen-presenting cells, cytotoxic T cells or pharmaceutical compositions of the present invention. Methods of inducing an immune response against cancer are also provided.

14 Claims, 8 Drawing Sheets

Specification includes a Sequence Listing.

(56) References Cited

FOREIGN PATENT DOCUMENTS

| | | |
|---|---|---|
| WO | 2006/085684 A2 | 8/2006 |
| WO | 2008/023842 A1 | 2/2008 |
| WO | 2008/047473 A1 | 4/2008 |
| WO | 2013/024582 A1 | 2/2013 |
| WO | 2014/010232 A1 | 1/2014 |

OTHER PUBLICATIONS

Abaza, et al; M Phase Phosphoprotein 1 is a Human Plus-end-directed Kinesin-Related Protein Required for Cytokinesis; J Biol Chem. Jul. 25, 2003; 278(30):27844-52. Epub. May 11, 2003.
Adams, et al; Prediction of binding to MHC class I molecules; J Immunol Methods. Sep. 25, 1995;185(2):181-90.
Akiyoshi; Trials Using Peptide Derived from Tumor-Rejection Antigen; Gan to Kagakuryouhou.1997; 24(5):511-9.
Akiyoshi; Vaccine therapy using MAGE antigenic peptides; Igaku No Ayumi. 1999;190(2):139-42.
Belli, et al; Vaccination of Metastatic Melanoma Patients with Autologous Tumor-Derived Heat Shock Protein gp96-Peptide Complexes: Clinical and Immunologic Findings; J Clin Oncol. Oct. 15, 2002;20(20):4169-80.
Boon; Tumor Antigens Recognized by Cytolytic T Lymphocytes: Present perspectives for Specific Immunotherapy; Int J Cancer. May 8, 1993;54(2):177-80.
Boon et al; Human Tumor Antigens Recognized by T Lymphocytes; J Exp Med. Mar. 1, 1996;183(3):725-9.
Butterfield, et al; Generation of Human T-cell Responses to an HLA-A2.1-restricted Peptide Epitope Derived from α-Fetoprotein; Cancer Res. Jul. 1, 1999,59(13):3134-42.
Coulie, et al; Cytolytic T-cell responses of cancer patients vaccinated with a MAGE antigen; Immunol Rev. Oct. 2002;188:33-42.
Dionne, et al; Functional characterization of CTL against gp100 altered peptide ligands; Cancer Immunol Immunother. Apr. 2003;52(4):199-206. Epub Feb. 18, 2003.
Dionne, et al; Her-2/neu altered peptide ligand-induced CTL responses: implications for peptides with increased HLA affinity and T-cell-receptor interaction; Cancer Immunol Immunother. Apr. 2004;53(4):307-14. Epub Nov. 5, 2003.
Falk et al; Allele-specific motifs revealed by sequencing of self-peptides eluted from MHC molecules; Nature. May 23, 1991;351(6324): 290-6.
Ferries et al; Identification of p53 Peptides Recognized by CD8+ T Lymphocytes from Patients with Bladder Cancer; Hum Immunol. Aug. 2001; vol. 62, No. 8 pp. 791-798.
Fujie, et al; A MAGE 1-encoded HLA-A24-Binding Synthetic Peptide Induces Specific Anti-Tumor Cytotoxic T Lymphocytes; Int J Cancer. Jan. 18, 1999;80(2): 169-72.
Harig, et al; Induction of cytotoxic T-cell responses against immunoglobulin V region-derived peptides modified at human leukocyte antigen-A2 binding residues; Blood. Nov. 15, 2001;98(10):2999-3005.
Harris; Structure and Function of the p53 Tumor Suppressor Gene: Clues for Rational Cancer Therapeutic Strategies; J Natl Cancer Inst. Oct. 16, 1996;88(20):1442-55.
Hoffman.et al; The Ability of Variant Peptides to Reverse the Nonresponsiveness of T Lymphocytes to the Wild-Type Sequence $p^{53}{}_{264-272}$ Epitope; J Immunol. Feb. 1, 2002; 168(3):1338-47.
Ito, et al; Identification of Bladder Cancer Antigens Recognized by IgG Antibodies of a Patient with Metastatic Bladder Cancer; Int J Cancer. Feb. 20, 2004; 108(5):712-24.
Ishizaki et al; Inhibition of Tumor Growth with Antiangiogenic Cancer Vaccine Using Epitope Peptides Derived from Human Vascular Endothelial Growth Factor Receptor 1; Clin. Cancer Res. Oct. 1, 2006; 12(19):5841-9.
Kamimoto, et al; Identification of a Novel Kinesin-related Protein, KRMP1, as a Target for Mitotic Peptidyl-prolyl Isomerase Pin1*; J Biol Chem. Oct. 5, 2001; 276(40):37520-8. Epub Jul. 24, 2001.

Kanehira, et al; Oncogenic Role of MPHOSPH1, a Cancer-Testis Antigen Specific to Human Bladder Cancer; Cancer Res. Apr. 1, 2007; 67(7):3276-85.
Kanehira, et al; Proceedings, Sixty-Fifth Annual Meeting of the Japanese Cancer Association; Aug. 28, 2006; 436(#O-666).
Kanehira, et al; Proceedings, 66th Annual Meeting of the Japanese Cancer Association; Aug. 25, 2007; 474(#P-1008).
Kangawa, et al; Neuomedin K: A Novel Mammalian Tachykinin Identified in Porcine Spinal Cord; Biochem Biophys Res Commun. Jul. 29, 1983; 114(2):533-40.
Kikuchi, et al; Identification of a SART-1-Derived Peptide Capable of Inducing HLA-A24-Restricted and Tumor-Specific Cytotoxic T Lymphocytes; Int J Cancer. May 5, 1999; 81(3):459-66.
Komori, et al; Identification of HLA-A2- or HLA-A24-Restricted CTL Epitopes Possibly Useful for Glypican-3-Specific Immunotherapy of Hepatocellular Carcinoma; Clin Cancer Res. May 1, 2006; 12(9):2689-97.
Kondo, et al; Prominent Roles of Secondary Anchor Residues in Peptide Binding to HLA-A24 Human Class I Molecules; J Immunol. Nov. 1, 1995;155(9):4307-12.
Kubo, et al; Definition of Specific Peptide Motifs for Four Major HLA-A Alleles; J Immunol. Apr. 15, 1994;152(8):3913-24.
Lee et al; Increased Vaccine-Specific T Cell Frequency After Peptide-Based Vaccination Correlates with Increased Susceptibility to In Vitro Stimulation But Does Not Lead to Tumor Regression; J Immunol. Dec. 1, 1999;163(11):6292-300.
Lutgendorf, et al; Diurnal Cortisol Variations and Symptoms in Patients with Interstitial Cystitis; J Urol. Mar. 2002; 167(3):1338-43.
Mao, et al; Geneseq Accession No. ABB05654; Apr. 29, 2002; "Human DNA binding protein RFX2-89 N-terminal peptide SEQ ID No. 7".
Mayfield; "Progression-free Survival: Patient Benefit or Lower Standard?" NCI Cancer Bulletin. May 13, 2008; vol. 5, No. 10.
Murray, et al; Human Biochemistry; 1993 publishing house MIR, 1:34.
Nishiu, et al; Microarray Analysis of Gene-expression Profiles in Diffuse Large B-cell Lymphoma: Identification of Genes Related to Disease Progression; Jpn J Cancer Res. Aug. 2002;93(8):894-901.
Obara, et al; Cancer Peptide Vaccine Therapy Developed from Oncoantigens Identified through Genome-wide Expression Profile Analysis for Bladder Cancer; Jpn J Clin Oncol. Jul. 2012;42(7):591-600. Epub May 25, 2012.
Obara et al; Tumor Specific Vaccine Therapy Using Novel Tumor Antigen Genes MPHOSPH1 and DEPDC1-Derived HLA-A 24 Restricted Epitope Peptides; Japanese Journal of Urological Surgery. 2009; 22 (Extra Supplement):277-279.
Oiso, et al; A Newly Identified MAGE-3-Derived Epitope Recognized by HLA-A24-Restricted Cytotoxic T Lymphocytes; Int J Cancer. May 5, 1999; 81(3):387-94.
Parker, et al; Scheme for Ranking Potential HLA-A2 Binding Peptides Based on Independent Binding of Individual Peptide Side-Chains; J Immunol. Jan. 1, 1994;152(1): 163-75.
Rammensee, et al; MHC ligands and peptide motifs; first listing; Immunogenetics. 1995;41(4): 178-228.
Rammensee, et al; Geneseq Accession No. AEG71129; Jun. 1, 2006; "Human tumor associated T-helper cell peptide epitope SEQ ID No. 89".
Rosenberg et al; Cancer immunotherapy: moving beyond current vaccines; Nat Med. Sep. 2004; 10(9):909-15.
Schartz et al; From the antigen-presenting cell to the antigen-presenting vesicle: The exosomes; Curr Opin Mol Ther. Aug. 2002;4 (4):372-81.
Schwartzentruber et al; gp100 Peptide Vaccine and Interleukin-2 in Patients with Advanced Melanoma; N Engl J Med. Jun. 2, 2011;364(22):2119-27.
Schueler-Furman, et al; Structure-based prediction of binding peptides to MHC class I molecules: Application to a broad range of MHC alleles; Protein Sci. Sep. 2000; 9(9):1838-46.
Tanaka, et al; Induction of Antitumor Cytotoxic T Lymphocytes with a MAGE-3-encoded Synthetic Peptide Presented by Human Leukocytes Antigen-A24[1]; Cancer Res. Oct. 15, 1997; 57(20): 4465-8.

(56) References Cited

OTHER PUBLICATIONS

Uchida, et al; Ring Finger Protein 43 as a New Target for Cancer Immunotherapy; Clin Cancer Res. Dec. 15, 2004; 10(24):8577-86.
Uger, et al; Geneseq Accession No. ADB39054; Dec. 4, 2003; "Human tumour derived peptide Tyr 171".
Van Der Burg, et al; Immunogenicity of Peptides Bound to MHC Class I Molecules Depends on the MHC-Peptide Complex Stability; J Immunol. May 1, 1996;156(9):3308-14.
Vissers, et al; The Renal Cell Carcinoma-associated Antigen G250 Encodes a Human Leukocyte Antigen (HLA)-A2.1-restricted Epitope Recognized by Cytotoxic T Lymphocytes; Cancer Res. Nov. 1, 1999; 59(21):5554-9.
Yamaue; Antigenic peptide therapy for tumors 3 (Ayumi) Cancer immunotherapy using CEA antigenic peptides; Igaku No Ayumi. 1999; 190(2):135-8.
Zaremba, et al; Identification of an Enhancer Agonist Cytotoxic T Lymphocyte Peptide from Human Carcinoembryonic Antigen; Cancer Res. Oct. 15, 1997; 57(20):4570-7.

U.S. Dept. of Health and Human Services; Food and Drug Administration; Center for Biologics Evaluation and Research; "Guidance for Industry Clinical Considerations for Therapeutic Cancer Vaccines" 1-16, 2011.
ISA/Japan Patent Office; International Search Report of PCT/JP2016/079716; dated Dec. 6, 2016.
Chujoh, et al; The role of anchor residues in the binding of peptides to HLA-A*1101 molecules; Tissue Antigens; 1998; 52:501-509.
Falk, et al; Peptide motifs of HLA-A1, -A31, and -A33 molecules; Immunogenetics; 1994; 40:238-241.
Takiguchi, et al; Analysis of three HLA-A*3303 binding peptide anchors using an HLA-A*3303 stabilization assay; Tissue Antigens; 2000; 55:296-302.
Janeway et al.; Antigen recognition by T lymphocyte; Immunobiology—The Immune System in Health and Disease—$3^{rd}$ Ed.; Apr. 1, 1998; Supervisor of translation: T. Sasazuki; pp. 130-131.

* cited by examiner a b a b a b a b

MPHOSPH1-DERIVED PEPTIDE, AND VACCINE INCLUDING SAME

CROSS-REFERENCE TO RELATED APPLICATIONS

The present application is a § 371 National Phase Application of PCT/JP2016/079716, filed Oct. 6, 2016, which application claims the benefit of Japanese Patent Application No. JP 2015-200220, filed on Oct. 8, 2015, the entire contents of which are incorporated by reference in their entireties for all purposes herein.

TECHNICAL FIELD

The present invention relates to the field of biological science, more specifically to the field of cancer therapy. In particular, the present invention relates to novel peptides that are effective as cancer vaccines, methods for either or both of treating and preventing tumors using the peptide(s), and pharmaceutical compositions comprising the peptide(s).

BACKGROUND ART

CD8-positive cytotoxic T lymphocytes (CTLs) are known to recognize epitope peptides derived from the tumor-associated antigens (TAAs) presented on the major histocompatibility complex (MHC) class I molecule expressed on cell surfaces, and then kill the tumor cells. Since the discovery of the melanoma antigen (MAGE) family, many TAAs have been discovered through immunological approaches (NPL1: Boon T, Int J Cancer 1993, 54(2): 177-80; NPL2: Boon T & van der Bruggen P, J Exp Med 1996, 183(3): 725-9). A part of these TAAs is currently undergoing clinical development as immunotherapeutic targets.

In several of the numerous TAAs, epitope peptides that can be recognized by CTLs are identified and their application in immunotherapy for various cancer types is anticipated (NPL3: Harris C C, J Natl Cancer Inst 1996, 88(20): 1442-55; NPL4: Butterfield L H et al., Cancer Res 1999, 59(13): 3134-42; NPL5: Vissers J L et al., Cancer Res 1999, 59(21): 5554-9; NPL6: van der Burg S H et al., J Immunol 1996, 156(9): 3308-14; NPL7: Tanaka F et al., Cancer Res 1997, 57(20): 4465-8; NPL8: Fujie T et al., Int J Cancer 1999, 80(2): 169-72; NPL9: Kikuchi M et al., Int J Cancer 1999, 81(3): 459-66; NPL10: Oiso M et al., Int J Cancer 1999, 81(3): 387-94). Until now, several clinical trials using these TAA-derived epitope peptides have been reported. However, unfortunately, the response rate is not high in many clinical trials (NPL11: Belli F et al., J Clin Oncol 2002, 20(20): 4169-80; NPL12: Coulie P G et al., Immunol Rev 2002, 188: 33-42; NPL13: Rosenberg S A et al., Nat Med 2004, 10(9): 909-15). Therefore, there is still demand for identification of novel CTL epitope peptides that can be applied to cancer immunotherapy.

MPHOSPH1 (M-phase phosphoprotein 1); reference sequence: GenBank Accession Number NM_016195 (SEQ ID NO: 185) or NM_001284259 (SEQ ID NO: 187)) has been identified as a protein that is specifically phosphorylated in the G2/M transition phase and that is characterized as a cell cycle-promoting kinesin-related protein. In particular, MPHOSPH1 has been reported as being a molecular motor having a division-promoting effect which plays an important role during cytoplasmic division (NPL14: Abaza A et al., J Biol Chem 2003, 278:27844-52). On the other hand, MPHOSPH1 has been identified as a novel molecule which is upregulated in bladder cancer, by using gene expression profiles in a genome-wide cDNA microarray containing 27,648 genes (NPL15: Kanehira M et al., Cancer Res 2007, 67(7):3276-85). In addition, in Northern blot analysis, the MPHOSPH1 gene product was not expressed in normal important organs except the testis. Further, down-regulation of MPHOSPH1 expression by siRNAs caused suppression of cell proliferation of bladder cancer cell lines (PTL1: WO2006/085684; PTL2: WO2008/023842).

Recently, MPHOSPH1-derived HLA-A02-restricted CTL epitope peptides (PTL3: WO2013/024582; PTL4: WO2008/047473) and HLA-A24-restricted CTL epitope peptides (PTL4: WO2008/047473) have been identified. Therapeutic effect by these peptides can be expected in cancer patients having the HLA-A02 type or HLA-A24 type, but cannot be expected in other cancer patients.

CITATION LIST

Patent Literature

[PTL 1] WO2006/085684
[PTL 2] WO2008/023842
[PTL 3] WO2013/024582
[PTL 4] WO2008/047473

Non Patent Literature

[NPL 1] Boon T, Int J Cancer 1993, 54(2): 177-80
[NPL 2] Boon T & van der Bruggen P, J Exp Med 1996, 183(3): 725-9
[NPL 3] Harris C C, J Natl Cancer Inst 1996, 88(20): 1442-55
[NPL 4] Butterfield L H et al., Cancer Res 1999, 59(13): 3134-42
[NPL 5] Vissers J L et al., Cancer Res 1999, 59(21): 5554-9
[NPL 6] van der Burg S H et al., J Immunol 1996, 156(9): 3308-14
[NPL 7] Tanaka F et al., Cancer Res 1997, 57(20): 4465-8
[NPL 8] Fujie T et al., Int J Cancer 1999, 80(2): 169-72
[NPL 9] Kikuchi M et al., Int J Cancer 1999, 81(3): 459-66
[NPL 10] Oiso M et al., Int J Cancer 1999, 81(3): 387-94
[NPL 11] Belli F et al., J Clin Oncol 2002, 20(20): 4169-80
[NPL 12] Coulie P G et al., Immunol Rev 2002, 188: 33-42
[NPL 13] Rosenberg S A et al., Nat Med 2004, 10(9): 909-15
[NPL 14] Abaza A et al., J Biol Chem 2003, 278:27844-52
[NPL 15] Kanehira M et al., Cancer Res 2007, 67(7):3276-85

SUMMARY OF THE INVENTION

The present invention relates to peptides that can induce CTLs that specifically react to MPHOSPH1-expressing cells. When these peptides form a complex with the human leukocyte antigen (HLA) and are presented to CD8 positive T cells by antigen-presenting cells (APCs) that present on their surface this complex, CTLs that show peptide-specific cytotoxic activity are induced. MPHOSPH1-derived peptides that have been identified so far to have CTL-inducing ability (CTL inducibility) are either HLA-A02-restricted or HLA-A24-restricted peptides, and cannot induce CTLs when antigen-presenting cells do not express these HLAs. Therefore, conventional peptides are not suitable for performing immunotherapy in subjects that do not have these HLAs. HLA-A11 and HLA-A33 are alleles commonly seen in Asians (Cao K et al., Hum Immunol 2001; 62(9): 1009-30), and it is desirable to administer HLA-A11-restricted peptides to HLA-A11-positive subjects and to administer HLA-A33-restricted peptides to HLA-A33-positive subjects. Hence, the present invention relates to MPHOSPH1-derived peptides with CTL-inducing ability that are restrictive to HLA-A11 or HLA-A33. Based on results disclosed herein, the peptides of the present invention have been proven to be epitope peptides that can induce a specific and potent immune response against cancer cells expressing MPHOSPH1 and HLA-A11 or HLA-A33.

Therefore, one of the objectives of the present invention is to provide MPHOSPH1-derived peptides that can induce CTLs in an HLA-A11- or HLA-A33-restrictive manner. These peptides can be used to induce CTLs in vitro, ex vivo or in vivo, or can be used to administer to subjects for the purpose of inducing an immune response against MPHOSPH1-expressing cancer cells. Preferable peptides are peptides comprising the amino acid sequence selected from among SEQ ID NOs: 5, 12, 27, 52, 53, 118, 119, and 170; more preferable peptides are nonapeptides or decapeptides; and even more preferable peptides are peptides consisting of the amino acid sequence selected from among SEQ ID NOs: 5, 12, 27, 52, 53, 118, 119, and 170.

The peptides of the present invention encompass peptides in which one, two or more amino acid(s) is/are substituted, deleted, inserted and/or added, as long as the resultant modified peptides retain the CTL-inducing ability of the original peptide.

The present invention further provides isolated polynucleotides encoding any one of the peptides of the present invention. Similar to the peptides of the present invention, these polynucleotides can be used for inducing APCs with CTL-inducing ability, and can be administered to subjects for inducing an immune response against MPHOSPH1-expressing cancer cells.

The present invention also provides compositions comprising one or more types of peptides of the present invention, one or more types of polynucleotides encoding one or more types of peptides of the present invention, APCs of the present invention, exosomes presenting peptides of the present invention, and/or CTLs of the present invention. The compositions of the present invention are preferably pharmaceutical compositions. The pharmaceutical compositions of the present invention can be used for treating and/or preventing cancer, as well as preventing postoperative recurrence thereof. They can also be used for inducing an immune response against cancer. When administered to a subject, a peptide of the present invention is presented on the surface of an APC, and as a result CTLs targeting the peptide are induced. Therefore, another objective of the present invention is to provide compositions for inducing CTLs, wherein the compositions comprise one or more types of peptides of the present invention, one or more types of polynucleotides encoding one or more types of peptides of the present invention, APCs of the present invention, and/or exosomes presenting peptides of the present invention.

A further objective of the present invention is to provide methods of inducing APCs having CTL-inducing ability, wherein the methods comprise a step of contacting one or more types of peptides of the present invention with an APC, or a step of introducing a polynucleotide encoding any one peptide of the present invention into an APC.

The present invention further provides a method of inducing CTLs, comprising a step of co-culturing a CD8-positive T cell with an APC that presents on its surface a complex of an HLA antigen and a peptide of the present invention, a step of co-culturing a CD8-positive T cell with an exosome that presents on its surface a complex of an HLA antigen and a peptide of the present invention, or a step of introducing into a CD8-positive T cell a vector comprising a polynucleotide encoding each subunit of a T cell receptor (TCR) capable of binding to a peptide of the present invention presented by an HLA antigen on a cell surface. The preferred HLA antigen in the present invention is HLA-A11 or HLA-A33.

A further objective of the present invention is to provide isolated APCs that present on their surface a complex of an HLA antigen and a peptide of the present invention. The present invention further provides isolated CTLs targeting a peptide of the present invention. These APCs and CTLs can be used in immunotherapy for MPHOSPH1-expressing cancers. In the present invention, the cancer to be subjected to immunotherapy is, for example, a cancer present in patients who have a homozygote or heterozygote of HLA-A11 or HLA-A33. Thus, the APCs or CTLs are also cells having a homozygote or heterozygote of HLA-A11 or HLA-A33. That is, the present invention provides immunotherapy for cancers expressing MPHOSPH1 and at least one HLA antigen selected from HLA-A11 and HLA-A33.

Another objective of the present invention is to provide methods of inducing an immune response against cancer in a subject, wherein the methods comprise a step of administering to the subject a composition comprising a peptide(s) of the present invention or a polynucleotide(s) encoding the peptide(s), an APC(s) of the present invention, an exosome(s) presenting a peptide(s) of the present invention, and/or a CTL(s) of the present invention. Another objective of the present invention is to provide methods of treating and/or preventing cancer, as well as preventing postoperative recurrence thereof in a subject, wherein the methods comprise a step of administering to the subject a peptide(s) of the present invention, a polynucleotide(s) encoding the peptide(s), an APC(s) of the present invention, an exosome(s) presenting a peptide(s) of the present invention, and/or a CTL(s) of the present invention.

In addition to the above, other objects and features of the present invention will become more fully apparent when the following detailed description is read in conjunction with the accompanying figures and examples. However, it is to be understood that both the foregoing summary of the present invention and the following detailed description are of exemplified embodiments, and not restrictive of the present invention or other alternate embodiments of the present invention. In particular, while the present invention is described herein with reference to a number of specific embodiments, it will be appreciated that the description is illustrative of the present invention and is not constructed as limiting of the present invention. Various modifications and applications may occur to those who are skilled in the art, without departing from the spirit and the scope of the present invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

It can be seen by comparison with the negative controls that peptide-specific IFN-gamma production was observed in Well #4 with MPHOSPH1-A33-9-608 (SEQ ID NO: 118) (a), Well #6 with MPHOSPH1-A33-9-1474 (SEQ ID NO: 119) (b), and Well #8 with MPHOSPH1-A33-10-57 (SEQ ID NO: 170) (c). Cells that showed a reaction, boxed in the photos, were proliferated to establish a CTL line. Meanwhile, MPHOSPH1-A33-9-1663 (SEQ ID NO: 48) (d) is shown as an example of typical negative data in which peptide-specific IFN-gamma production was not observed.

Figure 6:
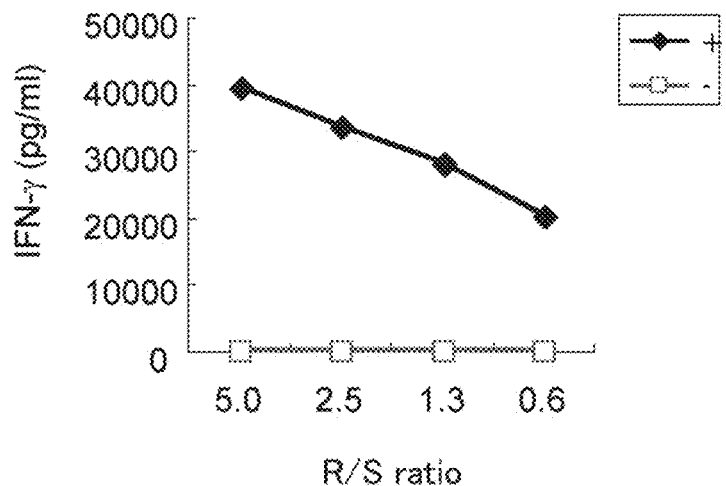
Figure 6:
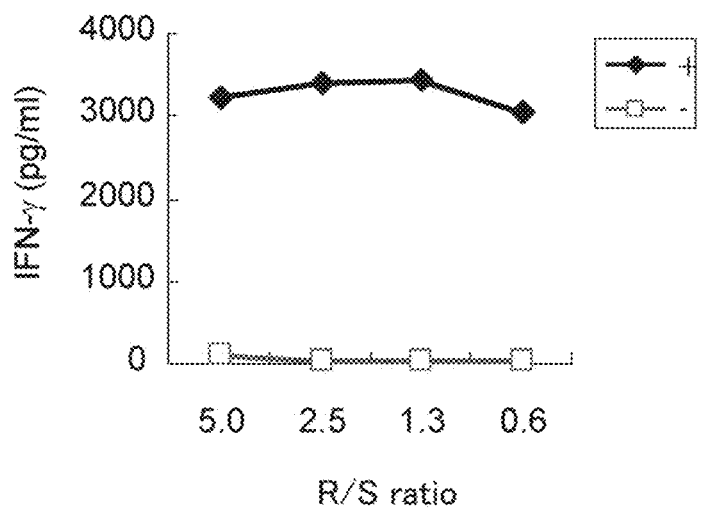

FIG. 6 consists of line graphs (a) to (b) showing results of measuring, by ELISA, IFN-gamma produced by a CTL line stimulated with MPHOSPH1-A33-9-608 (SEQ ID NO: 118) (a) or MPHOSPH1-A33-10-57 (SEQ ID NO: 170) (b). These results show that CTL lines that produce IFN-gamma in a peptide-specific manner were established after induction with each of the peptides. In the figure, "+" shows IFN-gamma production of the CTL line against target cells pulsed with a peptide of interest; and "−" shows IFN-gamma production of the CTL line against target cells that have not been pulsed with any peptide. The R/S ratio indicates the ratio of the cell number of CTL line (Responder cells) and the cell number of target cells that stimulate them (Stimulator cells).

Figure 7:
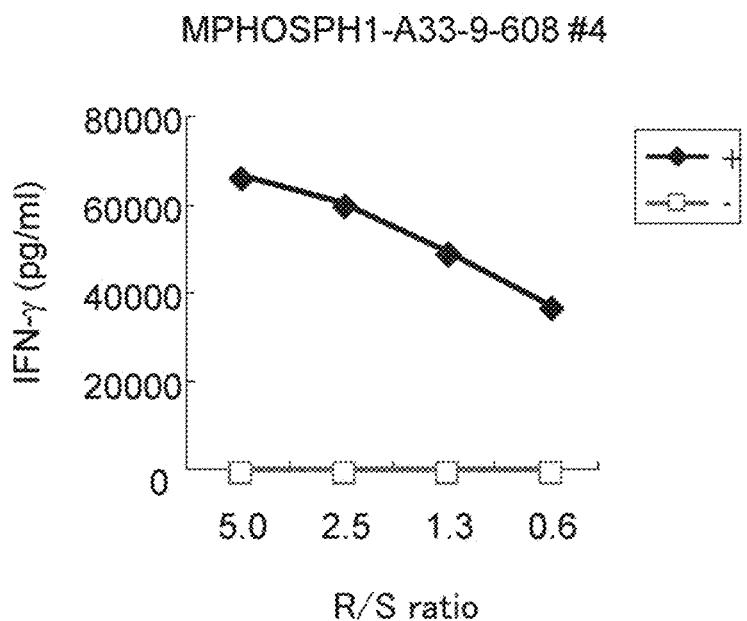
Figure 7:
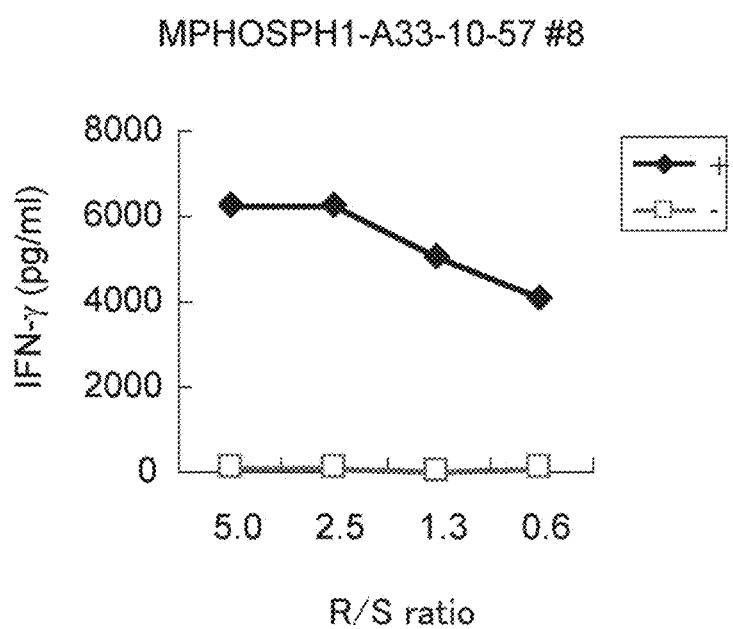

FIG. 7 consists of a series of line graphs (a) to (b) showing IFN-gamma production in a CTL clone established by the limiting dilution method following induction with MPHOSPH1-A33-9-608 (SEQ ID NO: 118) (a) or MPHOSPH1-A33-10-57 (SEQ ID NO: 170) (b). These results show the peptide-specific IFN-gamma production of the CTL clones. In the figure, "+" shows IFN-gamma production of the CTL clones against target cells pulsed with the peptide of interest; and "−" shows IFN-gamma production of the CTL clones against target cells that have not been pulsed with any peptide. The R/S ratio indicates the ratio of the cell number of CTL clone (Responder cells) and the cell number of target cells that stimulate them (Stimulator cells).

Figure 8:
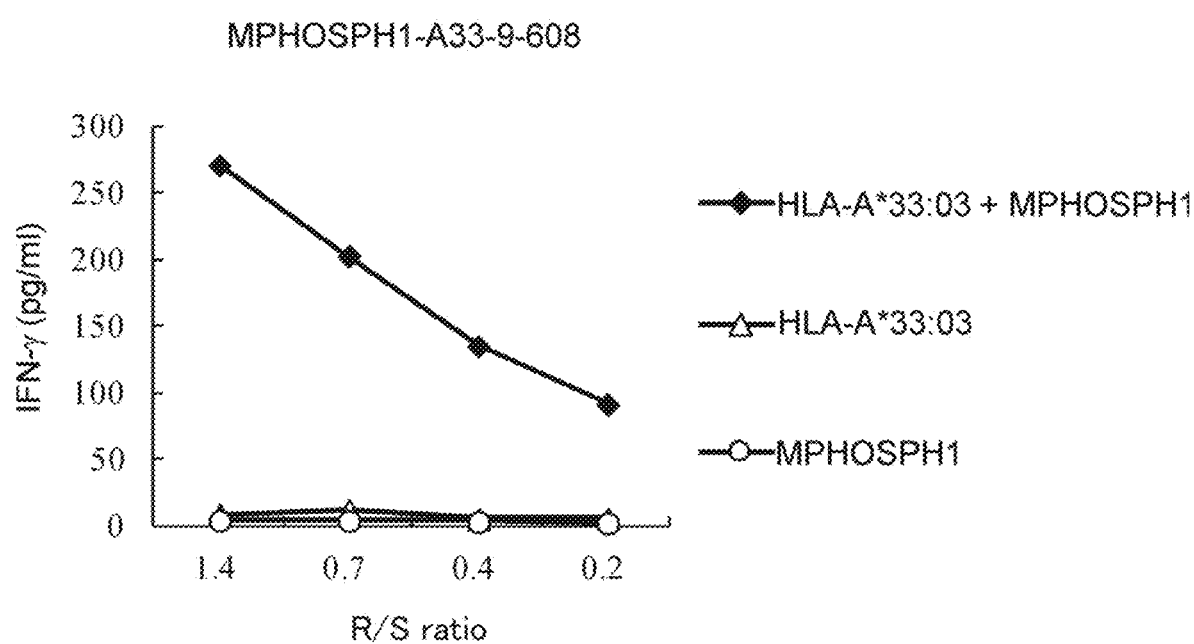

FIG. 8 is a line graph showing IFN-gamma production of CTL clones against target cells expressing both MPHOSPH1 and HLA-A*33:03. Target cells introduced with either HLA-A*33:03 or the full-length MPHOSPH1 gene were used as the negative control. The CTL clone established by induction using MPHOSPH1-A33-9-608 (SEQ ID NO: 118) showed IFN-gamma production against COS7 cells introduced with both the MPHOSPH1 and HLA-A*33:03 genes (black diamond). On the other hand, a significant IFN-gamma production was not shown against COS7 cells introduced with either one of HLA-A*33:03 (white triangle) and MPHOSPH1 (white circle).

MODE FOR CARRYING OUT THE INVENTION

Description of Embodiments

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

I. Definitions

The words "a", "an", and "the" as used herein mean "at least one" unless otherwise specifically indicated.

The terms "isolated" and "purified" used in relation with a substance (for example, peptide, antibody, polynucleotide or such) indicate that the substance does not substantially contain at least one substance that may else be included in a natural source. Thus, an isolated or purified peptide refers to a peptide that does not substantially contain another cellular material, for example, carbohydrate, lipid, and other contaminating proteins from the cell or tissue source from which the peptide is derived. When the peptide is chemically synthesized, an isolated or purified peptide refers to a peptide that does not substantially contain a precursor substance or another chemical substance. The phrase "does not substantially contain a cellular material" includes peptide preparations in which the peptide is separated from cellular components of the cells from which it is isolated or recombinantly produced. Thus, a peptide that does not substantially contain a cellular material encompasses peptide preparations that contain less than about 30%, 20%, 10%, or 5%, 3%, 2% or 1% (dry weight basis) of other cellular materials.

When the peptide is recombinantly produced, an isolated or purified peptide does not substantially contain culture medium, and a peptide which does not substantially contain culture medium encompasses peptide preparations that contain culture medium at less than about 20%, 10%, or 5%, 3%, 2% or 1% (dry weight basis) of the volume of the peptide preparation.

Alternatively, when the peptide is chemically synthesized, an isolated or purified peptide does not substantially contain a precursor substance or other chemical substances, and a peptide which does not substantially contain a precursor substance or other chemical substances encompasses peptide preparations that contain a precursor substance or other chemical substances at less than about 30%, 20%, 10%, 5%, 3%, 2% or 1% (dry weight basis) of the volume of the peptide preparation. That a particular peptide preparation is an isolated or purified peptide can be confirmed, for example, by the appearance of a single band following sodium dodecyl sulfate (SDS)-polyacrylamide gel electrophoresis and Coomassie Brilliant Blue staining or such of the gel. In a preferred embodiment, the peptides and polynucleotides of the present invention are isolated or purified.

The terms "polypeptide", "peptide" and "protein" are used interchangeably herein, and refer to polymers of amino acid residues. These terms are applied to also non-naturally occurring amino acid polymers comprising one or more non-naturally occurring amino acid residues, in addition to naturally occurring amino acid polymers. Non-naturally occurring amino acids include amino acid analogs, amino acid mimetics, and such.

The term "amino acid" as used herein refers to naturally occurring amino acids, as well as amino acid analogs and amino acid mimetics that functions similarly to the naturally occurring amino acids. Naturally occurring amino acids are those encoded by the genetic code, as well as those modified after translation in cells (e.g., hydroxyproline, gamma-carboxyglutamate, and O-phosphoserine, etc.). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine sulfoxide, methionine methyl sulfonium, and such). The phrase "amino acid mimetic" refers to compounds that have different structures from general amino acids but have similar functions to amino acids. Amino acids can be either L-amino acids or D-amino acids, and the peptides of the present invention are preferably L-amino acid polymers.

The terms "polynucleotide", "oligonucleotide", and "nucleic acid" are used interchangeably herein, and refer to a polymer of nucleotides.

The term "composition" used in the present specification is intended to encompass products that include specified ingredients in specified amounts, and any products generated directly or indirectly from combination of specified ingredients in the specified amounts. When the composition is a pharmaceutical composition, the term "composition" is intended to encompass products including active ingredient(s) and inert ingredient(s), as well as any products generated directly or indirectly from combination, complexation or aggregation of any two or more ingredients, from dissociation of one or more ingredients, or from other types of reactions or interactions of one or more ingredients. Thus, the pharmaceutical compositions of the present invention encompass any compositions made by admixing compounds or cells of the present invention with a pharmaceutically or physiologically acceptable carrier. Without being limited thereto, the terms "pharmaceutically acceptable carrier" or "physiologically acceptable carrier" used in the present specification include liquid or solid bulking agents, diluents, excipients, solvents, and encapsulation materials; and mean pharmaceutically or physiologically acceptable materials, compositions, substances or media.

Unless otherwise specified, the term "cancer" refers to a cancer that overexpresses the MPHOSPH1 gene; and examples thereof include bladder cancer, breast cancer, cervical cancer, cholangiocellular cancer, chronic myeloid leukemia (CML), colon cancer, gastric cancer, lung cancer, lymphoma, osteosarcoma, prostate cancer, kidney cancer, soft tissue tumor and such, without being limited thereto. In an exemplary embodiment, the "cancer" is a cancer that expresses MPHOSPH1 and HLA-A11 and/or HLA-A33.

Unless otherwise specified, the terms "cytotoxic T lymphocyte" and "cytotoxic T cell" and "CTL" are used interchangeably herein. Unless otherwise specifically indicated, they refer to a sub-group of T lymphocytes that can recognize non-self cells (for example, tumor/cancer cells, virus-infected cells) and induce the death of such cells.

Unless otherwise specified, the term "HLA-A11" refers to the HLA-A11 type which includes subtypes such as HLA-A*11:01, HLA-A*11:02, HLA-A*11:03, and HLA-A*11:04.

Unless otherwise specified, the term "HLA-A33" refers to the HLA-A33 type which includes subtypes such as HLA-A*33:03, HLA-A*33:01, and HLA-A*33:04.

In the context of a subject or patient, the phrase "HLA antigen of a subject (or patient) is HLA-A11" used herein indicates that a subject or patient has the HLA-A11 antigen gene homozygously or heterozygously as the MHC (Major Histocompatibility Complex) Class I molecule, and that the HLA-A11 antigen is expressed in the cells of the subject or patient as the HLA antigen. Similarly, the phrase "HLA antigen of a subject (or patient) is HLA-A33" used herein indicates that a subject or patient has the HLA-A33 antigen gene homozygously or heterozygously as the MHC (Major Histocompatibility Complex) Class I molecule and that the HLA-A33 antigen is expressed as the HLA antigen in the cells of the subject or patient.

As long as the methods and compositions of the present invention are useful in the context of cancer "treatment", the treatment is considered "efficacious" when it achieves clinical advantages, for example, reduction in the size, spreading or metastatic ability of cancer, retardation of cancer progression, alleviation of clinical symptoms of cancer, prolongation of survival period, suppression of postoperative recurrence in a subject. When the treatment is applied prophylactically, "efficacious" means that the treatment retards or prevents cancer formation, or prevents or alleviates clinical symptoms of cancer. Effectiveness is determined in relation to any publicly known method for diagnosing or treating a specific tumor type.

As long as the methods and compositions of the present invention are useful in the context of cancer "prevention (prophylaxis)", the term "prevention (prophylaxis)" herein includes any work that eases the load of disease-associated mortality or morbidity. Prevention (Prophylaxis) can be carried out at the "primary, secondary and tertiary prevention (prophylaxis) levels". Whereas the primary prevention (prophylaxis) avoids the development of a disease, prevention (prophylaxis) at the secondary and tertiary levels encompasses prevention (prophylaxis) of disease progression and appearance of symptoms, as well as workings intended to reduce adverse effects of the existing disease by restoring functions and reducing disease-associated complications. Alternately, prevention (prophylaxis) can include alleviation of severity of a specific disorder, for example, extensive preventive therapy intended to reduce tumor growth and metastasis.

In the context of the present invention, the treatment and/or prevention (prophylaxis) of cancer and/or prevention (prophylaxis) of postoperative recurrence thereof include either of the events such as inhibition of cancer cell proliferation, tumor involution or regression, induction of remission and suppression of cancer development, tumor regression, as well as reduction or inhibition of metastasis, suppression of postoperative recurrence of cancer, and prolongation of survival period. Effective treatment and/or prevention (prophylaxis) of cancer reduce mortality, improve prognosis of an individual with cancer, reduce the blood levels of tumor markers, and alleviate detectable symptoms associated with cancer. For example, alleviation or improvement of symptoms constitutes effective treatment and/or prevention (prophylaxis), and includes a condition in which the symptoms are stable or alleviated by 10%, 20%, 30% or more.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an "antibody" herein is used in the broadest sense and specifically covers intact monoclonal antibodies, polyclonal antibodies, multispecific antibodies (e.g., bispecific antibodies) formed from two or more intact antibodies, and antibody fragments so long as they exhibit the desired biological activity. An "antibody" may be antibodies of all classes (e.g., IgA, IgD, IgE, IgG and IgM).

Unless otherwise specified, the technical terms and scientific terms used herein all have the same meanings as terms commonly understood by one of ordinary skill in the art to which the present invention belongs.

II. Peptides

HLA-A11 and HLA-A33 are alleles commonly seen in Asians (Cao et al., Hum Immunol 2001; 62(9): 1009-30). Thus, an effective method of treating MPHOSPH1-expressing cancers for a great population of Asians can be provided by providing MPHOSPH1-derived CTL-inducing peptides restricted to HLA-A11 or HLA-A33. Thus, the present invention provides MPHOSPH1-derived peptides that are capable of inducing CTLs in an HLA-A11- or HLA-A33-restrictive manner.

The peptides of the present invention are MPHOSPH1-derived peptides that are capable of inducing CTLs in an HLA-A11- or HLA-A33-restrictive manner. Peptides capable of inducing CTLs in an HLA-A11-restrictive manner include peptides having the amino acid sequence selected from among SEQ ID NOs: 5, 12, 27, 52, and 53. Peptides capable of inducing CTLs in an HLA-A33-restrictive manner include peptides having the amino acid sequence selected from among SEQ ID NOs: 118, 119, and 170.

CTLs having a cytotoxic activity specific to these peptides can be established by in vitro stimulation of T cells by dendritic cells (DCs) pulsed with these peptides. The established CTLs show a specific cytotoxic activity against target cells pulsed with each of the peptides.

The MPHOSPH1 gene is overexpressed in cancer cells such as cancer cells in, for example, bladder cancer, breast cancer, cervical cancer, cholangiocellular cancer, chronic myeloid leukemia (CML), colon cancer, gastric cancer, lung cancer, lymphoma, osteosarcoma, prostate cancer, kidney cancer, soft tissue tumor and such, but is not expressed in most normal organs. It is thus an excellent target for immunotherapy. Therefore, the peptides of the present invention can be suitably used for cancer immunotherapy. A preferred peptide is a nonapeptide (a peptide consisting of 9 amino acid residues) or a decapeptide (a peptide consisting of 10 amino acid residues), and it is more preferably a peptide consisting of the amino acid sequence selected from among SEQ ID NOs: 5, 12, 27, 52, 53, 118, 119, and 170. For example, a peptide having the amino acid sequence of SEQ ID NO: 52 is suitable for induction of CTLs that show a specific cytotoxic activity against cells expressing HLA-A11 and MPHOSPH1, and can be suitably used for cancer immunotherapy for HLA-A11-positive patients. Additionally, for example, a peptide having the amino acid sequence of SEQ ID NO: 118 is suitable for induction of CTLs that show a specific cytotoxic activity against cells expressing HLA-A33 and MPHOSPH1, and can be suitably used for cancer immunotherapy for HLA-A33-positive patients. In a more preferred embodiment, the peptide of the present invention is a peptide consisting of the amino acid sequence selected from among SEQ ID NOs: 52 and 118.

For the peptides of the present invention, an additional amino acid residue(s) can be made to adjoin the amino acid sequence of the peptide of the present invention, as long as the resultant peptides retain the CTL-inducing ability of the original peptide. The additional amino acid residue(s) may be composed of any types of amino acid(s), as long as they do not impair the CTL-inducing ability of the original peptide. Therefore, the peptides of the present invention encompass peptides having CTL-inducing ability, comprising the amino acid sequence selected from among SEQ ID NOs: 5, 12, 27, 52, 53, 118, 119, and 170. Such peptides are, for example, less than about 40 amino acids, in many cases less than about 20 amino acids, and usually less than about 15 amino acids. Therefore, if the original peptide is a nonapeptide, the peptide of the present invention encompasses peptides that are 10 amino-acid long or 11-40 amino-acid long, which are produced by adjoining additional amino acid(s) to the peptide. Moreover, if the original peptide is a decapeptide, the peptide of the present invention encompasses peptides that are 11-40 amino-acid long. Such a peptide can be, for example, a peptide that is 11-20 amino-acid long or a peptide that is 11-15 amino-acid long. A preferred example of an additional amino acid residue(s) is an amino acid residue(s) adjacent to the amino acid sequence of the peptide of the present invention in the full-length amino acid sequence of MPHOSPH1 (for example, SEQ ID NO: 186 or 188). Therefore, the peptides of the present invention encompass peptides comprising the amino acid sequence selected from among SEQ ID NOs: 5, 12, 27, 52, 53, 118, 119, and 170, and wherein the peptides are peptide fragments of MPHOSPH1 and have CTL-inducing ability.

In general, modifications of one, two or more amino acids in a certain peptide do not affect the functions of the peptide, or in some cases even enhance the desired functions of the original peptide. In fact, modified peptides (i.e., peptides composed of the amino acid sequence in which one, two or several amino acid residues are modified (i.e., substituted, deleted, inserted, and/or added) compared to the original reference sequence) are known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention can be peptides comprising the amino acid sequence in which one, two or several amino acids are substituted, deleted, inserted and/or added to the amino acid sequence selected from among SEQ ID NOs: 5, 12, 27, 52, 53, 118, 119, and 170 and having CTL-inducing ability.

One skilled in the art can recognize that individual substitutions to an amino acid sequence that alter a single amino acid or a small percentage of amino acids tend to result in the conservation of the properties of the original amino acid side chain(s). Thus, those are frequently referred to as "conservative substitutions" or "conservative modifications"; and modification of a protein by "conservative substitution" or "conservative modification" may result in a modified protein that has similar functions as the original protein. Tables of conservative substitutions presenting functionally similar amino acids are well known in the art. Examples of amino acid side chain characteristics that functionally resemble include, for example, hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V):
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also encompassed in peptides of the present invention. However, peptides of the present invention are not restricted thereto and can include non-conservative modifications, so long as the modified peptide retains the CTL-inducing ability of the original peptide. Furthermore, modified peptides do not exclude CTL inducible peptides derived from polymorphic variants, interspecies homologues, and alleles of MPHOSPH1.

So long as a peptide retains the CTL-inducing ability of an original peptide, one can modify (i.e., substitute, delete, insert and/or add) a small number (for example, 1, 2 or several) or a small percentage of amino acids. Herein, the term "several" means 5 or fewer amino acids, for example, 4 or 3 or fewer. The percentage of amino acids to be modified is preferably 20% or less, more preferably 15% or less, even more preferably 10% or less or 1 to 5%.

When used in the context of immunotherapy, peptides of the present invention should be presented on the surface of a cell or exosome, preferably as a complex with an HLA antigen. Therefore, it is preferable that the peptides of the present invention possess high binding affinity to the HLA antigen. To that end, the peptides can be modified by substitution, deletion, insertion, and/or addition of the amino acid residues to yield a modified peptide having improved binding affinity. Since the regularity of the sequences of peptides displayed by binding to HLA antigens is already known (Falk, et al., Immunogenetics 1994 40 232-41; Chujoh, et al., Tissue Antigens 1998: 52: 501-9; Takiguchi, et al., Tissue Antigens 2000: 55: 296-302.), modifications based on such regularity can be introduced into the peptides of the present invention.

For example, in peptides having binding affinity for HLA Class I, the second amino acid from the N terminus and the C-terminal amino acid are generally anchor residues involved in the binding to HLA Class I (Rammensee H G, et al., Immunogenetics. 1995; 41(4): 178-228.). For example, for HLA-A11, threonine, valine, isoleucine, leucine, phenylalanine, and tyrosine for the second amino acid from the N terminus, and lysine and arginine for the C-terminal amino acid are known as anchor residues with high binding affinity for HLA-A11 (Falk, et al., Immunogenetics 1994, 40: 232-41; Chujoh, et al., Tissue Antigens 1998: 52: 501-9).

Further, in HLA-A11, there is auxiliary anchor residues at positions 3 and 7 from the N terminus; and it is known that leucine, phenylalanine, tyrosine, isoleucine, and alanine are preferred as the third amino acid from the N terminus, and that leucine, isoleucine, tyrosine, valine and phenylalanine are preferred as the seventh amino acid from the N terminus (Falk, et al., Immunogenetics 1994, 40: 232-41; Chujoh, et al., Tissue Antigens 1998: 52: 501-9). Thus, to enhance the HLA-A11-binding affinity, there is a possibility that it is desirable to substitute the second amino acid from the N terminus with threonine, valine, isoleucine, leucine, phenylalanine, or tyrosine, and/or to substitute the C-terminal amino acid with lysine or arginine. Further, there is a possibility that it is also desirable to substitute the third amino acid from the N terminus with leucine, phenylalanine, tyrosine, isoleucine, or alanine, and/or to substitute the seventh amino acid from the N terminus with leucine, isoleucine, tyrosine, valine or phenylalanine.

Thus, peptides with CTL-inducing ability, comprising an amino acid sequence in which, in the amino acid sequence selected from among SEQ ID NOs: 5, 12, 27, 52, and 53, the second amino acid from the N terminus is substituted with threonine, valine, isoleucine, leucine, phenylalanine, or tyrosine; the third amino acid from the N terminus is substituted with leucine, phenylalanine, tyrosine, isoleucine, or alanine; the seventh amino acid from the N terminus is substituted with leucine, isoleucine, tyrosine, valine or phenylalanine; and/or the C-terminal amino acid is substituted with arginine are encompassed by the peptides of the present invention.

In a preferred embodiment, the peptide of the present invention can be a peptide having CTL-inducing ability that consists of an amino acid sequence in which, in the amino acid sequence selected from among SEQ ID NOs: 5, 12, 27, 52, and 53, the second amino acid from the N terminus is substituted with threonine, valine, isoleucine, leucine, phenylalanine, or tyrosine; the third amino acid from the N terminus is substituted with leucine, phenylalanine, tyrosine, isoleucine, or alanine; the seventh amino acid from the N terminus is substituted with leucine, isoleucine, tyrosine, valine or phenylalanine; and/or the C-terminal amino acid is substituted with arginine.

That is, the peptides of the present invention encompass peptides having CTL-inducing ability, which comprise an amino acid sequence having one or more substitutions selected from (a) to (d) below introduced into the amino acid sequence selected from among SEQ ID NOs: 5, 12, 27, 52, and 53:
(a) the second amino acid from the N terminus is substituted with threonine, valine, isoleucine, leucine, phenylalanine, or tyrosine:
(b) the third amino acid from the N terminus is substituted with leucine, phenylalanine, tyrosine, isoleucine, or alanine;
(c) the seventh amino acid from the N terminus is substituted with leucine, isoleucine, tyrosine, valine or phenylalanine; and
(d) the C-terminal amino acid is substituted with arginine.

In a preferred embodiment, the peptide of the present invention may be a peptide having CTL-inducing ability that consists of an amino acid sequence having one or more substitutions selected from (a) to (d) above introduced into the amino acid sequence selected from among SEQ ID NOs: 5, 12, 27, 52, and 53. In the present invention, the preferred number of substitutions is 1, 2, 3 or 4 substitutions selected from (a) to (d) above.

The peptide of the present invention may be a peptide having CTL-inducing ability, which comprises an amino acid sequence in which, in the amino acid sequence selected from among SEQ ID NOs: 5, 12, 27, 52, and 53, the second amino acid from the N terminus is substituted with threonine, valine, isoleucine, leucine, phenylalanine, or tyrosine, and/or the C-terminal amino acid is substituted with lysine or arginine. Preferably, the peptide of the present invention may be a peptide having CTL-inducing ability, which consists of an amino acid sequence in which, in the amino acid sequence selected from among SEQ ID NOs: 5, 12, 27, 52, and 53, the second amino acid from the N terminus is substituted with threonine, valine, isoleucine, leucine, phenylalanine, or tyrosine, and/or the C-terminal amino acid is substituted with arginine. That is, the peptide of the present invention may be a peptide having CTL-inducing ability, which comprises an amino acid sequence having one or more substitutions selected from (a) and (b) below in the amino acid sequence selected from among SEQ ID NOs: 5, 12, 27, 52, and 53:
(a) the second amino acid from the N terminus is substituted with threonine, valine, isoleucine, leucine, phenylalanine, or tyrosine; and
(b) the C-terminal amino acid is substituted with arginine.

In a preferred embodiment, the peptide of the present invention may be a peptide having CTL-inducing ability, which consists of an amino acid sequence having one or more substitutions selected from (a) to (b) above introduced into the amino acid sequence selected from among SEQ ID NOs: 5, 12, 27, 52, and 53. In a more preferred embodiment, the second amino acid from the N terminus is substituted with threonine, valine, isoleucine, or leucine.

In HLA-A33, phenylalanine, tyrosine, alanine, isoleucine, leucine, and valine for the second amino acid from the N terminus, and lysine and arginine for the C-terminal amino acid are known as anchor residues with high binding affinity for HLA-A33 (Falk, et al., Immunogenetics 1994, 40: 232-41; Takiguchi, et al., Tissue Antigens 2000, 55: 296-302). Further, in HLA-A33, the first amino acid residue from the N terminus is also known to function as an anchor residue, and it is known that aspartic acid and glutamic acid is preferred as the first amino acid from the N terminus (Falk, et al., Immunogenetics 1994, 40: 232-41; Takiguchi, et al., Tissue Antigens 2000: 55: 296-302).

Thus, to maintain or enhance the HLA-A33-binding affinity, there is a possibility that it is desirable to substitute the first amino acid from the N terminus with aspartic acid or glutamic acid, the second amino acid from the N terminus with phenylalanine, tyrosine, alanine, isoleucine, leucine, or valine, and/or the C-terminal amino acid with lysine. Therefore, peptides having CTL-inducing ability, which comprise an amino acid sequence in which, in the amino acid sequence selected from among SEQ ID NOs: 118, 119, and 170, the first amino acid from the N terminus is substituted with aspartic acid or glutamic acid, the second amino acid from the N terminus is substituted with phenylalanine, tyrosine, alanine, isoleucine, leucine, or valine, and/or the C-terminal amino acid is substituted with lysine are encompassed by the peptides of the present invention.

In a preferred embodiment, the peptide of the present invention may be a peptide having CTL-inducing ability, which consists of an amino acid sequence in which, in the amino acid sequence selected from among SEQ ID NOs: 118, 119, and 170, the first amino acid from the N terminus is substituted with aspartic acid or glutamic acid, the second amino acid from the N terminus is substituted with phenylalanine, tyrosine, alanine, isoleucine, leucine, or valine, and/or the C-terminal amino acid is substituted with lysine.

That is, the peptides of the present invention encompass a peptide having CTL-inducing ability, which comprises an amino acid sequence having one or more substitutions selected from (a) to (c) below introduced into the amino acid sequence selected from among SEQ ID NOs: 118, 119, and 170:
(a) the first amino acid from the N terminus is substituted with aspartic acid or glutamic acid;
(b) the second amino acid from the N terminus is substituted with phenylalanine, tyrosine, alanine, isoleucine, leucine, or valine; and
(c) the C-terminal amino acid is substituted with lysine.

In a preferred embodiment, the peptide of the present invention may be a peptide having CTL-inducing ability, which consists of an amino acid sequence having one or more substitutions selected from (a) to (c) above introduced into the amino acid sequence selected from among SEQ ID NOs: 118, 119, and 170. In the present invention, the preferred number of substitutions is 1, 2 or 3 substitutions selected from (a) to (c) above.

Furthermore, the peptide of the present invention can be a peptide having CTL-inducing ability, which comprises an amino acid sequence in which, in the amino acid sequence selected from among SEQ ID NOs: 118, 119, and 170, the second amino acid from the N terminus is substituted with phenylalanine, tyrosine, alanine, isoleucine, leucine, or valine, and/or the C-terminal amino acid is substituted with lysine. Preferably, the peptide of the present invention can be a peptide having CTL-inducing ability, which consists of an amino acid sequence in which, in the amino acid sequence selected from among SEQ ID NOs: 118, 119, and 170, the second amino acid from the N terminus is substituted with phenylalanine, tyrosine, alanine, isoleucine, leucine, or valine, and/or the C-terminal amino acid is substituted with lysine. That is, the peptide of the present invention can be a peptide having CTL-inducing ability, which comprises an amino acid sequence having one or more substitutions selected from (a) and (b) below introduced into the amino acid sequence selected from among SEQ ID NOs: 118, 119, and 170:

(a) the second amino acid from the N terminus is substituted with phenylalanine, tyrosine, alanine, isoleucine, leucine, or valine; and (b) the C-terminal amino acid is substituted with lysine.

In a preferred embodiment, the peptide of the present invention may be a peptide having CTL-inducing ability, which consists of an amino acid sequence having one or more substitutions selected from (a) and (b) above introduced into the amino acid sequence selected from among SEQ ID NOs: 118, 119, and 170. In a more preferred embodiment, the second amino acid from the N terminus is substituted with phenylalanine or tyrosine.

Substitution(s) may be introduced into amino acid(s) not only at the anchor site(s), but also at a position(s) of potential T cell receptor (TCR) recognition site(s) of the peptides. Several research studies have demonstrated that a peptide that has amino acid substitutions, such as CAP1, p53$_{(264-272)}$, Her-2/neu$_{(369-377)}$ or gp100$_{(209-217)}$, may have equal to or better activity than that of the original peptide (Zaremba et al. Cancer Res. 1997, 57, 4570-7; T. K. Hoffmann et al. J Immunol. 2002, 168(3): 1338-47; S. O. Dionne et al. Cancer Immunol immunother. 2003, 52: 199-206; and S. O. Dionne et al. Cancer Immunology, Immunotherapy 2004, 53, 307-14).

The present invention also contemplates that one, two or several amino acids can be added to the N terminus and/or C terminus of the peptides of the present invention (for example, peptides consisting of the amino acid sequence selected from among SEQ ID NOs: 5, 12, 27, 52, 53, 118, 119, and 170). More specifically, the present invention provides peptides consisting of amino acid sequences in which one, two or several amino acids are added to either or both of the N terminus and C terminus of the amino acid sequences referred by each of the SEQ ID NOs. Such modified peptides that retain CTL-inducing ability are also included in the present invention. For example, when a peptide in which one, two or several amino acids are added to the N terminus and/or C terminus of a peptide consisting of the amino acid sequence of SEQ ID NO: 52 or 118 is contacted with an APC(s), it is incorporated into the APC(s) and processed to become a peptide consisting of the amino acid sequence of SEQ ID NO: 52 or 118. It can then induce CTLs through presentation on the cell surface of an APC via the antigen presentation pathway. More specifically, peptides of the present invention can be peptides in which one, two or several amino acids are added to either or both of the N terminus and C terminus.

Further, in another embodiment of the present invention, peptides consisting of amino acid sequences comprising one, two or several amino acid substitutions in the amino acid sequences referred by each of the SEQ ID NOs and in which one, two or several amino acids are added to either or both of the N terminus and C terminus of these substituted amino acid sequences are provided.

When the peptides of the present invention comprise amino acid substitution(s), the desired substitution positions can be, for example, one, two, three, or four positions selected from the second position from the N terminus, the third position from the N terminus, the seventh position from the N terminus, and the C terminus in the amino acid sequences referred by SEQ ID NOs: 5, 12, 27, 52, and 53 comprised in the peptides of the present invention. Alternatively, they can be one, two, or three positions selected from the first position from the N terminus, the second position from the N terminus, and the C terminus in the amino acid sequences referred by SEQ ID NOs: 118, 119, and 170.

However, when the amino acid sequence of a peptide is identical to a portion of the amino acid sequence of an endogenous or exogenous protein having a different function, side effects such as autoimmune disorders and/or allergic symptoms against specific substances may be induced. Therefore, it is preferable to perform homology searches using available databases to avoid situations in which the amino acid sequence of the peptide matches the amino acid sequence of another protein. When it becomes clear from the homology searches that no peptide exists with as few as 1 or 2 amino acid differences as compared to the objective peptide, the objective peptide can be modified in order to increase its binding affinity with HLA antigens, and/or increase its CTL-inducing ability without danger of such side effects.

Peptides in which one, two or several amino acids of a peptide of the present invention are modified are predicted to be able to retain CTL-inducing ability of the original peptide; however, it is preferable to verify the CTL-inducing ability of the modified peptides. Herein, the "peptide having CTL-inducing ability (CTL inducibility)" refers to a peptide that induces CTLs through APCs stimulated with the peptide. "CTL induction" includes induction of differentiation into CTLs, induction of CTL activation, induction of CTL proliferation, induction of CTL's cytotoxic activity, induction of CTL-mediated dissolution of target cells, and induction of increase of IFN-gamma production of CTLs.

The CTL-inducing ability can be confirmed by stimulating APCs that express an HLA antigen of interest (for example, B lymphocytes, macrophages, or dendritic cells) with a peptide, and mixing it with CD8-positive T cells; and then measuring IFN-gamma released by CTLs against the target cells. For the APCs, human peripheral blood mononuclear cell-derived dendritic cells can be preferably used. As a reaction system, transgenic animals generated to express an HLA antigen can be used. Alternatively, for example, the target cells may be radio-labelled with $^{51}$Cr or such, and the cytotoxic activity of the peptide-induced CTLs may be calculated from the radioactivity emitted from the target cells. Alternatively, in the presence of peptide-stimulated APCs, it is possible to evaluate the CTL-inducing ability by measuring the IFN-gamma produced and released by CTLs, and visualizing the inhibition zone on the media using anti-IFN-gamma monoclonal antibodies.

In addition to the modifications above, the peptides of the present invention can be linked to other peptides as long as the resultant linked peptide retains the CTL-inducing ability. An example of an appropriate peptide to be linked with the peptides of the present invention includes a CTL-inducing peptide derived from other TAAs. Further, the peptides of the present invention can also be linked with each other. Suitable linkers for use in linking peptides are known in the art, and for example, linkers such as AAY (P. M. Daftarian et al., J Trans Med 2007, 5:26), AAA, NKRK (SEQ ID NO: 189) (R. P. M. Sutmuller et al., J Immunol. 2000, 165:

7308-15), or K (S. Ota et al., Can Res. 62, 1471-6, K. S. Kawamura et al., J Immunol. 2002, 168: 5709-15) can be used. Peptides can be linked in various arrangements (for example, catenulate, repeated, etc.), and one can also link three or more peptides.

The peptides of the present invention can also be linked to other substances as long as the resultant linked peptide retains the CTL-inducing ability. Examples of an appropriate substance to be linked with a peptide of the present invention include, for example, a peptide, a lipid, a sugar or sugar chain, an acetyl group, and a naturally-occurring or synthetic polymer. The peptides of the present invention can be modified by glycosylation, side-chain oxidation, phosphorylation or such, as long as their CTL-inducing ability is not impaired. One can also perform such types of modifications to confer additional functions (for example, targeting function and delivery function) or to stabilize the peptide.

For example, to increase the in vive stability of a peptide, it is known in the art to introduce D-amino acids, amino acid mimetics or non-naturally occurring amino acids, and this concept may also be applied to peptides of the present invention. Peptide stability can be assayed by several methods. For example, stability can be tested by using a peptidase as well as various biological media such as human plasma and serum (see, e.g., Verhoef et al., Eur J Drug Metab Pharmacokin 1986, 11: 291-302).

Further, as stated above, among the modified peptides in which one, two, or several amino acid residues have been substituted, deleted, inserted and/or added, those having the same or higher activity as compared to original peptides can be screened for or selected. Thus, the present invention also provides methods of screening for or selecting modified peptides that have the same or higher activity than that of the original peptide. Specifically, the present invention provides a method of screening for a peptide having CTL-inducing ability, wherein the method comprises the steps of:
(a) generating candidate sequences consisting of an amino acid sequence in which one, two, or several amino acid residues are substituted, deleted, inserted and/or added to the original amino acid sequence consisting of the amino acid sequence selected from among SEQ ID NOs: 5, 12, 27, 52, 53, 118, 119, and 170;
(b) selecting from among the candidate sequences generated in (a), a candidate sequence that does not have a significant homology (sequence identity) with any known human gene product other than MPHOSPH1;
(c) contacting a peptide consisting of the candidate sequence selected in (b) with APCs;
(d) contacting the APCs of (c) with CD8-positive T cells; and
(e) selecting a peptide that has an equal to or higher CTL-inducing ability than that of a peptide consisting of the original amino acid sequence.

Herein, the peptide of the present invention is also described as a "MPHOSPH1 peptide(s)".

III. Preparation of Peptides of the Present Invention

Well known techniques can be used to prepare peptides of the present invention. For example, recombinant DNA technology or chemical synthesis can be used to prepare peptides of the present invention. Peptides of the present invention can be synthesized individually, or as longer polypeptides including two or more peptides. Peptides of the present invention can be isolated from host cells or synthesis reaction products after they are produced in the host cells using recombinant DNA technology or after they are chemically synthesized. That is, peptides of the present invention can be purified or isolated so as not to substantially contain other host-cell proteins and fragments thereof, or any other chemical substances.

The peptides of the present invention may contain modifications, such as glycosylation, side chain oxidation, or phosphorylation provided such modifications do not destroy the biological activity of the original peptide. Other illustrative modifications include incorporation of D-amino acids or other amino acid mimetics that may be used, for example, to increase the serum half life of the peptides.

A peptide of the present invention can be obtained through chemical synthesis based on the selected amino acid sequence. Examples of conventional peptide synthesis methods that can be adapted to the synthesis include the methods described in the documents below:
(i) Peptide Synthesis, Interscience, New York, 1966;
(ii) The Proteins, Vol. 2, Academic Press, New York, 1976;
(iii) "Peptide Synthesis" (in Japanese), Maruzen Co., 1975;
(iv) "Basics and Experiment of Peptide Synthesis" (in Japanese), Maruzen Co., 1985;
(v) "Development of Pharmaceuticals" (in Japanese), Continued Vol. 14 (peptide synthesis), Hirokawa, 1991;
(vi) WO99/67288; and
(vii) Barany G. & Merrifield R. B., Peptides Vol. 2, Solid Phase Peptide Synthesis, Academic Press, New York, 1980, 100-118.

Alternatively, the peptides of the present invention can be obtained by adapting any known genetic engineering methods for producing peptides (e.g., Morrison J, J Bacteriology 1977, 132: 349-51; Clark-Curtiss & Curtiss, Methods in Enzymology (Wu et al.) 1983, 101: 347-62). For example, first, a suitable vector harboring a polynucleotide encoding the peptide of the present invention in an expressible form (e.g., downstream of a regulatory sequence corresponding to a promoter sequence) is prepared and transformed into a suitable host cell. The host cell is then cultured to produce the peptide of the present invention. The peptide of the present invention can also be produced in vitro using an in vitro translation system.

IV. Polynucleotides

The present invention also provides a polynucleotide which encodes any of the peptides of the present invention. These include polynucleotides derived from the naturally occurring MPHOSPH1 gene (e.g., GenBank Accession No. NM_016195 (SEQ ID NO: 185) or GenBank Accession No. NM_001284259 (SEQ ID NO: 187)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described above without altering the encoded polypeptide. Such nucleic acid variations are "silent variations", which are one species of conservatively modified variations. Every nucleic acid sequence herein which encodes a peptide also describes every possible silent variation of the nucleic acid. One of ordinary skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. A DNA is suitably composed of bases such as A, T, C, and G, and T is replaced by U in an RNA.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (e.g., plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J 1984, 3: 801-5. The linkage products of several peptides that can be obtained in this manner can be purified as necessary and administered in this linked stated. In this case, the linked peptides produce antigen-presentable peptides by processing and the CTL-inducing activity of each of the peptides is elicited. Accordingly, when linking peptides, it is preferable that peptides with a same HLA restriction are combined. Alternatively, peptides can be administered as a mixture of individual peptides by cleaving the linkage portion.

V. Exosomes

The present invention further provides intracellular vesicles, referred to as exosomes, that present complexes formed between the peptides of the present invention and HLA antigens on their surface. Exosomes can be prepared, for example, using the methods detailed in JPH11-510507 and WO99/03499, and can be prepared using APCs obtained from patients who are subject to treatment and/or prevention (prophylaxis). The exosomes of the present invention can be inoculated as vaccines, in a fashion similar to the peptides of the present invention.

The type of the HLA antigens included in the above-described complexes must match that of the subject in need of treatment and/or prevention (prophylaxis). For example, HLA-A1 (for example, HLA-A*11:01) and HLA-A33 (for example, HLA-A*33:03) are alleles widely and generally seen in Asian populations, and these HLA antigen types are considered to be suitable for treatment in Asian patients. Typically in clinical practice, it is possible to select an appropriate peptide that has a high level of binding affinity for a specific HLA antigen or that has CTL-inducing ability by antigen presentation mediated by a specific HLA antigen, by studying in advance the HLA antigen type of the patient in need of treatment.

The exosomes of the present invention present on their surface a complex of a peptide of the present invention and HLA-A11 or HLA-A33. When the HLA that forms a complex with a peptide of the present invention is HLA-A11, the peptide of the present invention is preferably a peptide having the amino acid sequence selected from among SEQ ID NOs: 5, 12, 27, 52, and 53 or a modified peptide thereof, and more preferably a peptide consisting of the amino acid sequence selected from among SEQ ID NOs: 5, 12, 27, 52, and 53 or a modified peptide thereof. Further, when the HLA that forms a complex with a peptide of the present invention is HLA-A33, the peptide of the present invention is preferably a peptide having the amino acid sequence selected from among SEQ ID NOs: 118, 119, and 170 or a modified peptide thereof, and more preferably a peptide consisting of the amino acid sequence selected from among SEQ ID NOs: 118, 119, and 170 or a modified peptide thereof.

VI. Antigen-Presenting Cells (APCs)

The present invention further provides APCs that present on their surface complexes formed between HLA antigens and peptides of the present invention. Alternatively, the present invention provides APCs having on their cell surface complexes formed between HLA antigens and peptides of the present invention. The APCs of the present invention can be isolated APCs. When used in the context of cells (APCs, CTLs, etc.), the term "isolated" means that the cells are separated from another type of cells. The APCs of the present invention may be APCs induced from APCs derived from the patient to be subjected to treatment and/or prevention (prophylaxis), and can be administered as a vaccine by themselves or in combination with other drugs including a peptide(s), an exosome(s) or a CTL(s) of the present invention.

The APCs of the present invention are not limited to specific types of cells, and may be cells known to present proteinaceous antigens on their cell surface so as to be recognized by lymphocytes, for example, dendritic cells (DCs), Langerhans cells, macrophages, B cells, and activated T cells. Since DC is a representative APC that has the strongest CTL-inducing activity among APCs, DCs can be preferably used as the APCs of the present invention. In the present invention, the preferable DC is an isolated DC derived from human. Further, the APCs of the present invention can be mixtures of multiple types of cells having an antigen-presenting function and can be mixtures of APCs each of which presents different types of the peptides of the present invention.

For example, APCs of the present invention can be obtained by isolating DCs from peripheral blood mononuclear cells and then stimulating them in vitro, ex vivo, or in vive with the peptides of the present invention. When the peptide of the present invention is administered to a subject, APCs presenting the peptide of the present invention are induced in the body of the subject. Therefore, after the peptides of the present invention are administered to a subject, the APCs of the present invention can be obtained by collecting APCs from the subject. Alternatively, the APCs of the present invention can be obtained by contacting APCs collected from a subject with a peptide of the present invention.

In order to induce an immune response against MPHOSPH1-expressing cancer cells in a subject, the APCs of the present invention can be administered to the subject by themselves or in combination with other drugs including peptide(s), exosome(s) or CTL(s) of the present invention. For example, the ex vivo administration can comprise the following steps of:

(a) collecting APCs from a first subject;
(b) contacting the APCs of step (a) with a peptide; and
(c) administering the APCs of step (b) to a second subject.

The first subject and the second subject may be the same individual, or may be different individuals. When the first subject and the second subject are different individuals, it is preferable that the HLAs of the first subject and the second subject are of the same type. The APC obtained in step (b) above can be a vaccine for cancer treatment and/or prevention (prophylaxis).

The APCs of the present invention obtained by a method such as described above have CTL-inducing ability. The term "CTL-inducing ability (CTL inducibility)" used in the context of an APC(s) refers to the ability of the APC to be able to induce a CTL(s) when placed in contact with a CD8-positive T cell(s). Further, the "CTL-inducing ability (CTL inducibility)" includes the ability of an APC to induce CTL activation, the ability of an APC to induce CTL proliferation, the ability of an APC to facilitate CTL-mediated dissolution of target cells, and the ability of an APC to increase CTL-mediated IFN-gamma production. The CTL(s) induced by the APC of the present invention is a CTL(s) specific to MPHOSPH1 and demonstrates a specific cytotoxic activity against MPHOSPH1-expressing cells.

In addition to the above-described methods, the APCs of the present invention can be prepared by introducing a polynucleotide encoding a peptide of the present invention into APCs in vitro. The polynucleotide to be introduced can be in the form of DNA or RNA. The method of introduction is not particularly limited, and examples thereof include various methods conventionally performed in the art such as lipofection, electroporation and the calcium phosphate method. More specifically, methods described in Cancer Res 1996, 56: 5672-7; J Immunol 1998, 161: 5607-13; J Exp Med 1996, 184: 465-72, and JP2000-509281 can be used. By introducing a polynucleotide encoding a peptide of the present invention into an APC, the polynucleotide is transcribed and translated in the cell, and then the produced peptide is processed by MHC Class I and proceeds through a presentation pathway to present the peptide of the present invention on the cell surface of the APC.

In a preferred embodiment, the APC of the present invention presents on its cell surface a complex formed between a peptide of the present invention and HLA-A11 (more preferably HLA-A*11:01) or HLA-A33 (more preferably HLA-A*33:03). When the HLA that forms a complex with a peptide of the present invention is HLA-A11, the peptide of the present invention is preferably a peptide having the amino acid sequence selected from among SEQ ID NOs: 5, 12, 27, 52, and 53 or a modified peptide thereof, and more preferably a peptide consisting of the amino acid sequence selected from among SEQ ID NOs: 5, 12, 27, 52, and 53. When the HLA that forms a complex with a peptide of the present invention is HLA-A33, the peptide of the present invention is preferably a peptide having the amino acid sequence selected from among SEQ ID NOs: 118, 119, and 170 or a modified peptide thereof, and more preferably a peptide consisting of the amino acid sequence selected from among SEQ ID NOs: 118, 119, and 170.

The APC(s) of the present invention is preferably an APC(s) induced by a method comprising a step described (a) or (b) below:

(a) contacting an APC(s) expressing at least one HLA selected from among HLA-A11 (more preferably HLA-A*11:01) and HLA-A33 (more preferably HLA-A*33:03) with a peptide of the present invention; or
(b) introducing a polynucleotide encoding a peptide of the present invention into an APC(s) expressing at least one HLA selected from among HLA-A11 (more preferably HLA-A*11:01) and HLA-A33 (more preferably HLA-A*33:03).

The peptide of the present invention to be contacted with the HLA-A1-expressing APC(s) is preferably a peptide having the amino acid sequence selected from among SEQ ID NOs: 5, 12, 27, 52, and 53 or a modified peptide thereof, and more preferably a peptide consisting of the amino acid sequence selected from among SEQ ID NOs: 5, 12, 27, 52, and 53.

The peptide of the present invention to be contacted with the HLA-A33-expressing APC(s) is preferably a peptide having the amino acid sequence selected from among SEQ ID NOs: 118, 119, and 170 or a modified peptide thereof, and more preferably a peptide consisting of the amino acid sequence selected from among SEQ ID NOs: 118, 119, and 170.

The present invention provides use of a peptide of the present invention for the manufacture of a pharmaceutical composition that induces an APC(s) having CTL-inducing ability. In addition, the present invention provides a method or process of manufacturing a pharmaceutical composition that induces an APC(s) having CTL-inducing ability. Further, the present invention provides a peptide of the present invention for inducing an APC(s) having CTL-inducing ability.

VII. Cytotoxic T Lymphocytes (CTLs)

The CTL induced by a peptide of the present invention can be used as a vaccine in a similar manner to the peptide of the present invention for enhancing an immune response targeting MPHOSPH1-expressing cancer cells in vivo. Thus, the present invention provides CTLs that are induced or activated by a peptide of the present invention. The CTLs of the present invention are CTLs that target a peptide of the present invention, and are capable of binding to a complex of a peptide of the present invention and an HLA antigen. Binding of a CTL to the complex is mediated via a T cell receptor (TCR) present on the cell surface of the CTL. The CTLs of the present invention can be isolated CTLs. The preferable CTLs are isolated CTLs of human origin. The CTLs of the present invention can be mixtures of CTLs each of which targets different types of peptides of the present invention.

The CTLs of the present invention can be obtained by (1) administering a peptide of the present invention to a subject, (2) stimulating APCs and CD8-positive T cells, or peripheral blood mononuclear cells (PBMCs) derived from a subject with a peptide of the present invention in vitro, (3) contacting in vitro CD8-positive T cells or PBMCs with APCs or exosomes that present on their surface a complex of an HLA antigen and a peptide of the present invention, or (4) introducing into CD8-positive T cells a vector comprising a polynucleotide encoding each subunit of a T cell receptor (TCR) capable of binding to a peptide of the present invention presented on cell surface via an HLA antigen. The exosomes and APCs used in the method of (2) or (3) above can be prepared by methods described in the "V. Exosomes" and "VI. Antigen-presenting cells (APCs)" sections, respectively, and the details of the method of (4) above will be described in the "VIII. T cell receptor (TCR)" section.

The CTLs of the present invention can be administered by themselves to patients who are subject to treatment and/or prevention (prophylaxis), or in combination with other drugs including peptide(s), APC(s) or exosome(s) of the present invention for the purpose of regulating effects. Further, the CTLs of the present invention can be CTLs induced from CD8-positive T cells derived from the patients who are subject to administration of the CTLs. The CTLs of the present invention act specifically on target cells that present the peptides of the present invention, for example, the same peptides used to induce the CTLs of the present invention. The target cells may be cells that endogenously express MPHOSPH1, such as cancer cells, or cells transfected with the MPHOSPH1 gene. Cells that present a peptide of the present invention on their cell surface due to stimulation by the peptide can become a target of attack by the CTLs of the present invention. The cells targeted by the CTLs of the present invention are preferably cells that are positive for at least one of HLA-A11 (more preferably HLA-A*11:01) and HLA-A33 (more preferably HLA-A*33:03).

In a preferred embodiment, the CTLs of the present invention target specifically cells that express both MPHOSPH1 and at least one HLA selected from among HLA-A11 (more preferably HLA-A*11:01) and HLA-A33 (more preferably HLA-A33:03). In the present invention, the cells targeted by the CTLs can be cells that have any of the alleles of HLA-A11 and HLA-A33 homozygously or heterozygously.

Herein, that the CTL "targets" cells refers to CTL recognition of cells that present on their cell surface a complex of HLA and a peptide of the present invention and demonstration of a cytotoxic activity against the cells. Further, "specifically target" refers to that the CTLs demonstrate a cytotoxic activity against those cells, but do not show a damaging activity to other cells. The expression "recognize cells" used in the context of CTLs refers to binding to a complex of HLA and a peptide of the present invention presented on cell surface via its TCR, and demonstrating a specific cytotoxic activity against the cell. Therefore, the CTLs of the present invention are preferably CTLs that can bind via TCR to a complex formed between a peptide of the present invention and HLA-A11 (more preferably HLA-A*11:01) or HLA-A33 (more preferably HLA-A*33:03) presented on cell surface.

Furthermore, the CTLs of the present invention are preferably CTLs induced by a method comprising a step described in (a) or (b) below:
(a) contacting in vitro CD8-positive T cells with APCs or exosomes that present on their surface a complex of a peptide of the present invention and HLA-A11 (more preferably HLA-A*11:01) or HLA-A33 (more preferably HLA-A*33:03); or
(b) introducing into CD8-positive T cells a polynucleotide encoding each subunit of a TCR capable of binding to a peptide of the present invention presented on cell surface by HLA-A*11 (more preferably HLA-A11:01) or HLA-A33 (more preferably HLA-A*33:03). The CTLs induced by this method are cells having TCRs that specifically recognize the complex of the peptide and HLA antigen used for the induction. Accordingly, they are cells having a structural difference from other CTLs that have different reaction specificity due to the difference in the structure of the TCR.

VIII. T Cell Receptors (TCRs)

The present invention also provides compositions comprising a polynucleotide encoding each subunit of a TCR capable of binding to a peptide of the present invention presented on cell surface by an HLA antigen, and methods of using the same. The polynucleotide confers CD8-positive T cells with specificity against MPHOSPH1-expressing cancer cells through expression on the surface of CD8-positive T cells of a TCR capable of binding to a peptide of the present invention presented on the surface of target cells by an HLA antigen. Polynucleotides encoding an alpha chain(s) and a beta chain(s) can be identified as the TCR subunit of the CTL induced by a peptide of the present invention by using known methods in the art (WO2007/032255 and Morgan et al., J Immunol, 171, 3288 (2003)). For example, PCR methods are preferred for TCR analysis. Without being limited thereto, PCR primers for analysis may be, for example, a primer set(s) for amplification by combining the 5' side primer and the 3' side primer(s) below: 5' side primer:

```
5'-R Primer
                              (SEQ ID NO: 181)
(5'-gtctaccaggcattcgcttcat-3')

3' side primers:
TCR-alpha-chain C-region-specific
3-TRa-C Primer
                              (SEQ ID NO: 182)
(5'-tcagctggaccacagccgcagcgt-3')

TCR-beta-chain C1-region-specific
3-TRb-C1 Primer
                              (SEQ ID NO: 183)
(5'-tcagaaatcctttctcttgac-3')
or TCR-beta-chain C2-region-specific
3-TR-beta-C2 Primer
                              (SEQ ID NO: 184)
(5'-ctagcctctggaatcctttctctt-3')
```

The TCRs formed by introducing the identified polynucleotides into CD8-positive T cells can bind with high binding affinity to the target cells that present a peptide of the present invention, and mediates efficient killing of the target cells presenting a peptide of the present invention in vivo and in vitro.

A polynucleotide encoding each TCR subunit can be incorporated into an appropriate vector, for example, retrovirus vector. These vectors are well known in the art. The polynucleotide or a vector comprising thereof in an expressible form can be introduced into a CD8-positive T cell, for example, a CD8-positive T cell derived from a patient. The present invention provides off-the-shelf compositions that allow rapid and easy production of modified T cells that have superior cancer cell-killing properties by rapid modification of the patient's own T cells (or T cells derived from another subject).

Herein, a specific TCR is a TCR that can confer a specific cytotoxic activity against target cells by specifically recognizing a complex of a peptide of the present invention and an HLA antigen presented on the surface of the target cell when the TCR is present on the surface of a CD8-positive T cell. Specific recognition of the above-described complex can be confirmed by any known method, and preferable examples thereof include HLA multimer staining analysis using HLA molecules and peptides of the present invention and ELISPOT assay methods. Specific TCR-mediated recognition of target cell by T cell introduced with the above-described polynucleotide and signal transduction in the cell can be confirmed by carrying out an ELISPOT assay. When the above-described TCR is present on the surface of a CD8-positive T cell, whether the TCR can confer a target cell-specific cytotoxic activity against the CD8-positive T cell can also be confirmed by known methods. Preferable methods include, for example, measuring the cytotoxic activity against target cells by a chrome release assay method or such.

The present invention provides, in the context of HLA-A11, CTLs prepared by transforming CD8-positive T cells with a polynucleotide encoding each subunit of TCR that binds to, for example, a complex formed by a peptide having the amino acid sequence selected from among SEQ ID NOs: 5, 12, 27, 52, and 53 and an HLA-A11 antigen.

The present invention provides, in the context of HLA-A33, CTLs prepared by transforming CD8-positive T cells with a polynucleotide encoding each subunit of TCR that binds to, for example, a complex formed by a peptide having the amino acid sequence selected from among SEQ ID NOs: 118, 119, and 170 and an HLA-A33 antigen.

The transformed CTLs are capable of homing (translocation of lymphocytes from the blood to lymphatic tissues) in vivo and may be propagated by a well-known in vitro culturing method (for example, Kawakami et al., J Immunol., 1989, 142: 3452-61). The CTLs of the present invention can be used to form an immunogenic composition useful for disease treatment or prevention (prophylaxis) in a patient in need of treatment or prevention (prophylaxis) (the contents are incorporated herein for reference WO2006/031221).

IX. Pharmaceutical Compositions

The present invention further provides compositions or pharmaceutical compositions, comprising at least one active ingredient selected from below:
(a) a peptide of the present invention;
(b) a polynucleotide encoding a peptide of the present invention in an expressible form;
(c) an APC of the present invention;
(d) an exosome of the present invention; and
(e) a CTL of the present invention.

The pharmaceutical compositions of the present invention can comprise as needed a carrier(s), an excipient(s) or such commonly used in pharmaceuticals without particular limitations, in addition to the active ingredient(s) described above. An example of a carrier that can be used in a pharmaceutical composition of the present invention includes sterilized water, physiological saline, phosphate buffer, culture fluid and such. Therefore, the present invention also provides pharmaceutical compositions, comprising at least one active ingredient selected from (a) to (e) below and a pharmaceutically acceptable carrier:
(a) a peptide of the present invention;
(b) a polynucleotide encoding a peptide of the present invention in an expressible form;
(c) an APC of the present invention;
(d) an exosome of the present invention; and
(e) a CTL of the present invention.

Further, the pharmaceutical compositions of the present invention can comprise, as needed, stabilizers, suspensions, preservatives, surfactants, solubilizing agents, pH adjusters, aggregation inhibitors and such.

The MPHOSPH1 expression significantly up-regulates in cancer cells compared with normal tissues. Thus, a peptide of the present invention or a polynucleotide encoding the peptide can be used to treat and/or prevent cancer, and/or prevent postoperative recurrence thereof. Therefore, the present invention provides pharmaceutical compositions for treating and/or preventing cancer, and/or preventing postoperative recurrence thereof, comprising one or more types of peptides or polynucleotides of the present invention as an active ingredient. Alternatively, the peptides of the present invention can be made to be presented on the surface of exosomes or APCs for use as pharmaceutical compositions. In addition, CTLs of the present invention targeting any one of the peptides of the present invention can also be used as an active ingredient of the pharmaceutical compositions of the present invention. The pharmaceutical compositions of the present invention may comprise a therapeutically effective amount or a pharmaceutically effective amount of the above-described active ingredient.

The pharmaceutical compositions of the present invention may also be used as a vaccine. In the context of the present invention, the term "vaccine" (also called "immunogenic composition") refers to a composition that has a function of inducing an immune response that leads to antitumor action when inoculated into an animal. Thus, a pharmaceutical composition of the present invention can be used to induce an immune response that leads to antitumor action in a subject. The immune response induced by a peptide, a polynucleotide, an APC, a CTL and a pharmaceutical composition of the present invention is not particularly limited as long as it is an immune response that leads to antitumor action, and examples include induction of cancer cell-specific CTLs and induction of cancer cell-specific cytotoxic activity.

The pharmaceutical compositions of the present invention can be used to treat and/or prevent cancer, and/or prevent postoperative recurrence thereof in human subjects or patients. The pharmaceutical compositions of the present invention can be used preferably to a subject positive for at least one HLA selected from among HLA-A11 and HLA-A33. Further, the pharmaceutical compositions of the present invention can be used preferably to treat and/or prevent cancers expressing MPHOSPH1 and at least one HLA selected from among HLA-A1 and HLA-A33, and/or prevent postoperative recurrence thereof.

In another embodiment, the present invention provides use of an active ingredient selected from below in the manufacture of a pharmaceutical composition for treating or preventing cancer:
(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

Alternatively, the present invention further provides an active ingredient selected from below for use in treating or preventing cancer:
(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

Alternatively, the present invention further provides a method or process for manufacturing a pharmaceutical composition for treating or preventing cancer, wherein the method or process comprises a step of formulating at least one active ingredient selected from below with a pharmaceutically or physiologically acceptable carrier:

(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

In another embodiment, the present invention further provides a method or process for manufacturing a pharmaceutical composition for treating or preventing cancer, wherein the method or process comprises a step of mixing an active ingredient selected from below with a pharmaceutically or physiologically acceptable carrier:

(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

In another embodiment, the present invention further provides a method for treating or preventing cancer, which comprises a step of administering to a subject at least one active ingredient selected from below:

(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

In the present invention, peptides having the amino acid sequence selected from among SEQ ID NOs: 5, 12, 27, 52, and 53 are identified as HLA-A11-restricted epitope peptides that can induce a potent and specific immune response. Therefore, pharmaceutical compositions of the present invention comprising at least one of the peptides having the amino acid sequence selected from among SEQ ID NOs: 5, 12, 27, 52, and 53 are suitable particularly for administration to a subject having HLA-A11 (for example, HLA-A*11:01) as an HLA antigen. The same applies to pharmaceutical compositions comprising a polynucleotide encoding any of these peptides (i.e., polynucleotides of the present invention), an APC or exosome that presents these peptides (i.e., APCs or exosomes of the present invention), or a CTL targeting these peptides (i.e., CTLs of the present invention). That is, pharmaceutical compositions comprising an active ingredient in association with a peptide having the amino acid sequence selected from among SEQ ID NOs: 5, 12, 27, 52, and 53 are suitable for administration to subjects having HLA-A11 (i.e., HLA-A11-positive subjects). In a more preferred embodiment, the pharmaceutical composition of the present invention is a pharmaceutical composition that comprises a peptide having the amino acid sequence of SEQ ID NO: 52.

Similarly, in the present invention, peptides having the amino acid sequence selected from among SEQ ID NOs: 118, 119, and 170 are identified as HLA-A33-restricted epitope peptides that can induce a potent and specific immune response. Therefore, pharmaceutical compositions of the present invention comprising at least one of the peptides having the amino acid sequence selected from among SEQ ID NOs: 118, 119, and 170 are suitable particularly for administration to a subject having HLA-A33 (for example, HLA-A*33:03) as an HLA antigen. The same applies to pharmaceutical compositions comprising a polynucleotide encoding any of these peptides (i.e., polynucleotides of the present invention), an APC or exosome that presents these peptides (i.e., APCs or exosomes of the present invention), or a CTL targeting these peptides (i.e., CTLs of the present invention). That is, pharmaceutical compositions comprising an active ingredient in association with a peptide having the amino acid sequence selected from among SEQ ID NOs: 118, 119, and 170 are suitable for administration to subjects having HLA-A33 (i.e., HLA-A33-positive subjects). In a more preferred embodiment, the pharmaceutical composition of the present invention is a pharmaceutical composition that comprises a peptide having the amino acid sequence of SEQ ID NO: 118.

Cancers to be treated and/or prevented by pharmaceutical compositions of the present invention are not particularly limited as long as they are cancers that express MPHOSPH1, and include various types of cancers, for example, bladder cancer, breast cancer, cervical cancer, cholangiocellular cancer, chronic myeloid leukemia (CML), colon cancer, gastric cancer, lung cancer, lymphoma, osteosarcoma, prostate cancer, kidney cancer, soft tissue tumor and such. Moreover, the pharmaceutical compositions of the present invention are preferably used on subjects that homozygously or heterozygously have an HLA allele selected from among HLA-A11 and HLA-A33.

In addition to the active ingredients described above, the pharmaceutical compositions of the present invention can comprise the other peptides that have the ability to induce CTLs against cancer cells (for example, the other TAA-derived CTL-inducing peptides), the other polynucleotides encoding the other peptides, the other cells that present the other peptides, or such.

The pharmaceutical compositions of the present invention may also optionally comprise the other therapeutic substances as an active ingredient, as long as they do not inhibit the anti-tumor effects of the above-described active ingredients such as peptides of the present invention. For example, the pharmaceutical compositions of the present invention may optionally comprise anti-inflammatory compositions, analgesics, chemotherapeutics and the like. In addition to including the other therapeutic substances to a pharmaceutical composition of the present invention itself, one can also administer the pharmaceutical composition of the present invention sequentially or concurrently with one or more other pharmaceutical compositions. The dose of the pharmaceutical composition of the present invention and the other pharmaceutical compositions depend on, for example, the type of pharmaceutical composition used and the disease being treated, as well as the scheduling and routes of administration.

It should be understood that in consideration of the formulation type, the pharmaceutical composition of the present invention may include other components conventional in the art, in addition to the ingredients specifically mentioned herein.

The present invention also provides articles of manufacture or kits that comprise a pharmaceutical composition of the present invention. The articles of manufacture or kits of the present invention can include a container that houses the pharmaceutical composition of the present invention. An example of an appropriate container includes a bottle, a vial or a test tube, but is not limited thereto. The container may be formed of various materials such as glass or plastic. A label may be attached to the container, and the disease or disease state to which the pharmaceutical composition of the present invention should be used may be described in the label. The label may also indicate directions for administration and such.

The articles of manufacture or kits of the present invention may further comprise a second container that houses pharmaceutically acceptable diluents optionally, in addition to the container that houses the pharmaceutical composition of the present invention. The articles of manufacture or kits of the present invention may further comprise the other materials desirable from a commercial standpoint and the user's perspective, such as the other buffers, diluents, filters, injection needles, syringes, and package inserts with instructions for use.

As needed, the pharmaceutical composition of the present invention can be provided in a pack or dispenser device that can contain one or more units of dosage forms containing active ingredients. The pack can include, for example, a metallic foil or a plastic foil such as a blister pack. Instructions for administration can be attached to the pack or dispenser device.

(1) Pharmaceutical Compositions Comprising Peptide(s) as an Active Ingredient

The pharmaceutical composition comprising a peptide of the present invention can be formulated by conventional formulation methods as needed. The pharmaceutical compositions of the present invention may comprise as needed in addition to the peptide of the present invention, carriers, excipients and such commonly used in pharmaceuticals without particular limitations. Examples of carriers that can be used in pharmaceutical compositions of the present invention include sterilized water (for example, water for injection), physiological saline, phosphate buffer, phosphate buffered saline, Tris buffered saline, 0.3% glycine, culture fluid, and such. Further, the pharmaceutical compositions of the present invention may comprise as needed stabilizers, suspensions, preservatives, surfactants, solubilizing agents, pH adjusters, aggregation inhibitors, and such. The pharmaceutical compositions of the present invention can induce specific immunity against MPHOSPH1-expressing cancer cells, and thus can be applied for the purpose of cancer treatment or prevention (prophylaxis).

For example, the pharmaceutical compositions of the present invention can be prepared by dissolving in pharmaceutically or physiologically acceptable water-soluble carriers such as sterilized water (for example, water for injection), physiological saline, phosphate buffer, phosphate buffered saline, and Tris buffered saline and adding, as needed, stabilizers, suspensions, preservatives, surfactants, solubilizing agents, pH adjusters, aggregation inhibitors and such, and then sterilizing the peptide solution. The method of sterilizing a peptide solution is not particularly limited, and is preferably carried out by filtration sterilization. Filtration sterilization can be performed using, for example, a filtration sterilization filter of 0.22 micro-m or less in pore diameter. The filtration-sterilized peptide solution can be administered to a subject, for example, as an injection, without being limited thereto.

The pharmaceutical compositions of the present invention may be prepared as a freeze-dried formulation by freeze-drying the above-described peptide solution. The freeze-dried formulation can be prepared by filling the peptide solution prepared as described above into an appropriate container such as an ampule, a vial or a plastic container, followed by freeze drying and encapsulation into the container with a wash-sterilized rubber plug or such after pressure recovery. The freeze-dried formulation can be administered to a subject after it is re-dissolved in pharmaceutically or physiologically acceptable water-soluble carriers such as sterilized water (for example, water for injection), physiological saline, phosphate buffer, phosphate buffered saline, Tris buffered saline and such before administration. Preferred examples of pharmaceutical compositions of the present invention include injections of such a filtration-sterilized peptide solution, and freeze-dried formulations that result from freeze-drying the peptide solution. The present invention further encompasses kits comprising such a freeze-dried formulation and re-dissolving solution. The present invention also encompasses kits comprising a container that houses the freeze-dried formulation, which is a pharmaceutical composition of the present invention, and a container that houses a re-dissolving solution thereof.

The pharmaceutical compositions of the present invention can comprise a combination of two or more types of the peptides of the present invention. The combination of peptides can take a cocktail form of mixed peptides, or can be conjugated with each other using standard techniques. For example, peptides can be chemically linked or expressed as single fusion polypeptide sequences. By administering a peptide of the present invention, the peptide is presented on APCs by an HLA antigen at a high density, and then subsequently CTLs that react specifically to a complex formed between the presented peptide and the HLA antigen are induced. Alternatively, APCs (for example, DCs) are removed from a subject, and subsequently stimulated with peptides of the present invention to obtain APCs that present any of the peptides of the present invention on their cell surface. These APCs are re-administered to a subject to induce CTLs in the subject, and as a result, the aggressiveness towards MPHOSPH1-expressing cancer cells can be increased.

The pharmaceutical compositions of the present invention may also comprise an adjuvant known for effectively establishing cellular immunity. An adjuvant refers to a compound that enhances the immune response against an antigen that has immunological activity when administered together (or successively) with the antigen. Known adjuvants described in literatures, for example, Clin Microbiol Rev 1994, 7: 277-89, can be used. Examples of a suitable adjuvant include aluminum salts (aluminum phosphate, aluminum hydroxide, aluminum oxyhydroxide and such), alum, cholera toxin, *Salmonella* toxin, Incomplete Freund's adjuvant (IFA), Complete Freund's adjuvant (CFA), ISCOMatrix, GM-CSF and other immunostimulatory cytokines, oligodeoxynucleotide containing the CpG motif (CpG7909 and such), oil-in-water emulsions, Saponin or its derivatives (QS21 and such), lipopolysaccharide such as Lipid A or its derivatives (MPL, RC529, GLA, E6020 and such), lipopeptides, lactoferrin, flagellin, double-stranded RNA or its derivatives (poli IC and such), bacterial DNA, imidazoquinolines (Imiquimod, R848 and such), C-type lectin ligand (trehalose-6,6'-dibehenate (TDB) and such), CD1d ligand (alpha-galactosylceramide and such), squalene emulsions (MF59, AS03, AF03 and such), PLGA, and such, without being limited thereto. The adjuvant may be contained in another container separate from the pharmaceutical composition comprising a peptide of the present invention in the kits comprising the pharmaceutical composition of the present invention. In this case, the adjuvant and the pharmaceutical composition may be administered to a subject in succession, or mixed together immediately before administration to a subject. Such kits comprising a pharmaceutical composition comprising a peptide of the present invention and an adjuvant are also provided by the present invention. When the pharmaceutical composition of the present invention is a freeze-dried formulation, the kit can further comprise a re-dissolving solution. Further, the present invention provides kits comprising a container that houses a pharmaceutical composition of the present invention and a container that stores an adjuvant. The kit can further comprise as needed a container that stores the re-dissolving solution.

When an oil adjuvant is used as an adjuvant, the pharmaceutical composition of the present invention may be prepared as an emulsion. Emulsions can be prepared, for example, by mixing and stirring the peptide solution prepared as described above and an oil adjuvant. The peptide solution may be one that has been re-dissolved after freeze-drying. The emulsion may be either of the W/O-type emulsion and O/W-type emulsion, and the W/O-type emulsion is preferred for obtaining a high immune response-enhancing effect. IFA can be preferably used as an oil adjuvant, without being limited thereto. Preparation of an emulsion can be carried out immediately before administration to a subject, and in this case, the pharmaceutical composition of the present invention may be provided as a kit comprising the peptide solution of the present invention and an oil adjuvant. When the pharmaceutical composition of the present invention is a freeze-dried formulation, the kit can further comprise a re-dissolving solution.

Further, the pharmaceutical composition of the present invention may be a liposome formulation within which a peptide of the present invention is encapsulated, a granular formulation in which a peptide is bound to beads with several micrometers in diameter, or a formulation in which a lipid is bound to a peptide.

In another embodiment of the present invention, the peptide of the present invention may also be administered in the form of a pharmaceutically acceptable salt. Preferred examples of salts include salts with alkali metals (lithium, potassium, sodium and such), salts with alkaline-earth metals (calcium, magnesium and such), salts with other metals (copper, iron, zinc, manganese and such), salts with organic bases, salts with amines, salts with organic acids (acetic acid, formic acid, propionic acid, fumaric acid, maleic acid, succinic acid, tartaric acid, citric acid, malic acid, oxalic acid, benzoic acid, methanesulfonic acid and such), and salts with inorganic acids (hydrochloric acid, phosphoric acid, hydrobromic acid, sulfuric acid, nitric acid and such). The phrase "pharmaceutically acceptable salt" used herein refers to a salt that retains the pharmacological and pharmaceutical efficacy and property of the compound. Therefore, pharmaceutical compositions comprising a pharmaceutically acceptable salt of a peptide of the present invention are also encompassed by the present invention. Further, the "peptide of the present invention" also encompasses, in addition to the free peptide, pharmaceutically acceptable salts thereof.

In some embodiments, the pharmaceutical compositions of the present invention may further include a component which primes CTLs. Lipids have been identified as substances capable of priming CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinyl-seryl-serine (P3CSS) can be used to prime CTLs when covalently attached to an appropriate peptide (see, e.g., Deres et al., Nature 1989, 342: 561-4).

Examples of suitable methods for administering the peptides or pharmaceutical compositions of the present invention include oral, epidermal, subcutaneous, intramuscular, intraosseous, peritoneal, and intravenous injections, as well as systemic administration or local administration to the vicinity of the targeted sites, but are not limited thereto. A preferred administration method includes subcutaneous injection to the vicinity of lymph nodes such as the armpit or groin. More specifically, for example, subcutaneous administration is preferred when the pharmaceutical composition of the present invention comprises a peptide or exosome as an active ingredient. Alternatively, compositions having APCs or CTLs as an active ingredient can be administered by intravenous injection or such. The administration can be performed by single administration or boosted by multiple administrations.

The peptides of the present invention can be administered to a subject in a therapeutically or pharmaceutically effective amount for treating cancer or in a therapeutically or pharmaceutically effective amount for inducing immunity (more specifically CTLs) against MPHOSPH1-expressing cancer cells. The dose of the peptides of the present invention can be appropriately adjusted according to the disease to be treated, the patient's age and weight, the method of administration and such. For each of the peptides of the present invention, the dose is usually 0.001 mg-1000 mg, for example, 0.01 mg-100 mg, for example, 0.1 mg-30 mg, for example, 0.1 mg-10 mg, for example, 0.5 mg-5 mg. The dosing interval can be once every several days to several months, and for example, the dosing can be done in a once-per-week interval. A skilled artisan can appropriately select a suitable dose (dosage).

In a preferred embodiment, the pharmaceutical compositions of the present invention comprise a therapeutically effective amount of a peptide of the present invention and a pharmaceutically or physiologically acceptable carrier. In another embodiment, the pharmaceutical compositions of the present invention comprise a therapeutically effective amount of a peptide of the present invention, a pharmaceutically or physiologically acceptable carrier, and an adjuvant. The pharmaceutical compositions of the present invention can comprise 0.001 mg-1000 mg, preferably 0.01 mg-100 mg, more preferably 0.1 mg-30 mg, even more preferably 0.1 mg-10 mg, for example, 0.5 mg-5 mg of a peptide of the present invention. When a pharmaceutical composition of the present invention is an injection, it can comprise a peptide of the present invention at a concentration of 0.001 mg/ml-1000 mg/ml, preferably 0.01 mg/ml-100 mg/ml, more preferably 0.1 mg/ml-30 mg/ml, even more preferably 0.1 mg/ml-10 mg/ml, for example, 0.5 mg/ml-5 mg/ml. In this case, for example, 0.1 to 5 ml, preferably 0.5 ml to 2 ml of the pharmaceutical composition of the present invention can be administered to a subject by injection.

Further, the present invention provides methods of treating and/or preventing cancer and/or preventing postoperative recurrence thereof, which comprise administering to a subject a therapeutically effective amount of a peptide of the present invention or a pharmaceutical composition of the present invention. As described above, the peptides of the present invention can be administered to a subject in a single dose of usually 0.001 mg-1000 mg, for example, 0.01 mg-100 mg, for example, 0.1 mg-30 mg, for example, 0.1 mg-10 mg, or for example, 0.5 mg-5 mg. In a preferred embodiment, the peptides of the present invention are administered to a subject together with an adjuvant. Further, the dosing interval can be once every several days to several months, preferably once every several days to every month, for example, once every week or once every two weeks.

(2) Pharmaceutical Compositions Containing Polynucleotides as the Active Ingredient The pharmaceutical compositions of the present invention can also contain polynucleotides encoding the peptides of the present invention in an expressible form. Herein, the phrase "in an expressible form" means that the polynucleotide, when introduced into a cell, will be expressed as a peptide of the present invention. In an exemplified embodiment, the sequence of the polynucleotide of the present invention includes regulatory elements necessary for expression of the peptide of the present invention. The polynucleotide(s) of the present invention can be equipped with a sequence necessary to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859, 5,589,466, 5,804,566, 5,739,118, 5,736,524, 5,679,647; and WO98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. For example, as a vector to express the peptide of the present invention, vaccinia virus can be used. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization, e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide of the present invention into a patient can be either direct, in which case the patient can be directly exposed to a vector harboring the polynucleotide of the present invention, or indirect, in which case, cells are first transformed with the vector harboring the polynucleotide of the present invention in vitro, then the cells are transplanted into the patient. These two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215. Methods commonly known in the art of recombinant DNA technology which can also be used for the present invention are described in Ausubel et al., Current Protocols in Molecular Biology, John Wiley & Sons, N Y, 1993; and Krieger, Gene Transfer and Expression, A Laboratory Manual, Stockton Press, N Y, 1990.

Similar to peptide administration, administration of polynucleotides may be performed by oral, intradermal, subcutaneous, intravenous, intramuscular, intraosseous and/or peritoneal injection, and such. Administration of polynucleotides can be a systemic administration or a local administration to the vicinity of the targeted sites. The administration can be performed by single administration or boosted by multiple administrations. The polynucleotides of the present invention can be administered to a subject in a therapeutically or pharmaceutically effective dose for inducing immunity (more specifically CTLs) against MPHOSPH1-expressing cancer cells, or in a therapeutically or pharmaceutically effective dose for treating cancer. The dose of a polynucleotide in a suitable carrier or the dose of a polynucleotide in cells transformed with a polynucleotide encoding a peptide of the present invention can be appropriately adjusted according to the disease to be treated, the patient's age and weight, the method of administration and such, and this may be usually 0.001 mg-1000 mg, for example, 0.01 mg-100 mg, for example, 0.1 mg-30 mg, for example, 0.1 mg-10 mg, or for example, 0.5 mg-5 mg. The dosing interval can be once every several days to several months, and for example, the dosing can be done in a once-per-week interval. A skilled artisan can appropriately select a suitable dose (dosage).

X. Methods of Using Peptides, Exosomes, APCs and CTLs

The peptides and polynucleotides of the present invention can be used to induce APCs and CTLs. CTLs can also be induced using the exosomes and APCs of the present invention. The peptides, polynucleotides, exosomes, and APCs of the present invention can be used in combination with any other compound(s) as long as their CTL-inducing ability is not inhibited. Therefore, CTLs of the present invention can be induced using a pharmaceutical composition comprising any of the peptides, polynucleotides, APCs and exosomes of the present invention. Further, APCs of the present invention can be induced using a pharmaceutical composition comprising a peptide or polynucleotide of the present invention.

(1) Methods of Inducing APCs

The present invention provides methods of inducing APCs having CTL-inducing ability, using a peptide(s) or polynucleotide(s) of the present invention.

The methods of the present invention comprise a step of contacting an APC with a peptide of the present invention in vitro, ex vivo, or in vivo. For example, a method of contacting APCs with the peptide ex vivo may comprise the steps below:

(a) collecting APCs from a subject; and (b) contacting the APCs of step (a) with a peptide of the present invention.

The above-described APCs are not limited to a particular type of cell, and DCs, Langerhans cells, macrophages, B cells, and activated T cells which are known to present a proteinaceous antigen on their cell surface to be recognized by lymphocytes can be used. DCs have the most potent CTL-inducing ability among APCs, and thus it is preferable to use DCs. Any peptides of the present invention can be used by themselves or in combination with other peptides of the present invention. Further, peptides of the present invention can be used in combination with other CTL-inducing peptides (for example, other TAA-derived CTL-inducing peptides).

Meanwhile, when a peptide of the present invention is administered to a subject. APCs are contacted with the peptide in vivo, and as a result, APCs having a high CTL-inducing ability are induced in the body of the subject. Therefore, the methods of the present invention may comprise a step of administering a peptide of the present invention to a subject. Similarly, when a polynucleotide of the present invention is administered to a subject in an expressible form, a peptide of the present invention is expressed in vivo, the expressed peptide is contacted with APCs in vivo, and as a result APCs having a high CTL-inducing ability are induced in the body of the subject. Therefore, the present invention may also comprise a step of administering a polynucleotide of the present invention to a subject.

In order to induce APCs having CTL-inducing ability, the present invention may comprise a step of introducing a polynucleotide of the present invention into APCs. For example, the method may comprise the steps below:
 (a) collecting APCs from a subject; and
 (b) introducing a polynucleotide encoding a peptide of the present invention into the APCs of step (a).

Step (b) can be performed as described in the above "VI. Antigen-presenting cells (APCs)" section.

Thus, in one embodiment, the present invention provides a method of inducing APCs having CTL-inducing ability, which comprises the step (a) or (b) below:
 (a) contacting APCs with a peptide of the present invention; and
 (b) introducing a polynucleotide encoding a peptide of the present invention into APCs.

Furthermore, the present invention provides a method of preparing APCs having CTL-inducing ability, which comprises the step (a) or (b) below:
 (a) contacting APCs with a peptide of the present invention; or
 (b) introducing a polynucleotide encoding a peptide of the present invention into APCs.

The above-described methods can be performed in vitro, ex vivo, or in vivo, and it is preferable to perform them in vitro or ex vivo. APCs used in the above-described methods may be derived from a subject scheduled for administration of the induced APCs, or they may be derived from a different subject. When APCs derived from a subject (donor) different from the subject scheduled for administration are used, the subject of administration and the donor must have the identical HLA type.

In the methods of the present invention, when a peptide having the amino acid sequence selected from among SEQ ID NOs: 5, 12, 27, 52, and 53 or a modified peptide thereof is used as a peptide of the present invention, the HLA type is preferably HLA-A11 (more preferably HLA-A*11:01) in both the subject of administration and the donor. Alternatively, APCs used in the above-described methods are preferably APCs that express HLA-A11 (more preferably HLA-A*11:01).

Similarly, when a peptide comprising the amino acid sequence selected from among SEQ ID NOs: 118, 119, and 170 or a modified peptide thereof is used as a peptide of the present invention, the HLA is preferably HLA-A33 (more preferably HLA-A*33:03) in both the subject of administration and the donor. Alternatively, APCs used in the above-described methods are preferably APCs that express HLA-A33 (more preferably HLA-A*33:03). The APCs can be prepared using known methods from PBMCs after PBMCs are separated from blood collected from a donor by a specific gravity centrifugal method or such.

In another embodiment, the present invention also provides pharmaceutical compositions that comprise a peptide of the present invention or a polynucleotide encoding the peptide for inducing an APC(s) having CTL-inducing ability.

Alternatively, the present invention further provides use of a peptide of the present invention or a polynucleotide encoding the peptide in the manufacture of a pharmaceutical composition for inducing an APC(s) having CTL-inducing ability.

Alternatively, the present invention further provides peptides of the present invention or polynucleotides encoding the peptides for use in the induction of an APC(s) having CTL-inducing ability.

Alternatively, the present invention further provides methods or processes of manufacturing a pharmaceutical composition for inducing an APC(s), wherein the method or process comprises a step of formulating a peptide of the present invention or a polynucleotide encoding the peptide with a pharmaceutically or physiologically acceptable carrier.

In another embodiment, the present invention further provides methods or processes of manufacturing a pharmaceutical composition for inducing an APC(s) having CTL-inducing ability, wherein the method or process comprises a step of mixing a peptide of the present invention or a polynucleotide encoding the peptide with a pharmaceutically or physiologically acceptable carrier.

APCs induced by the methods of the present invention can induce CTLs specific to MPHOSPH1 (i.e., CTLs of the present invention).

(2) Methods of Inducing CTLs

The present invention also provides methods of inducing CTLs using peptides, polynucleotides, exosomes or APCs of the present invention. The present invention further provides methods of inducing CTLs using one or more polynucleotides encoding a polypeptide(s) that can form a T cell receptor (TCR) (i.e., TCR subunit) capable of recognizing a complex of a peptide of present invention and an HLA antigen. Preferably, the methods of inducing CTLs comprise at least one steps selected from below:
 (a) contacting CD8-positive T cells with antigen-presenting cells that present on their surface a complex of an HLA antigen and a peptide of present invention;
 (b) contacting CD8-positive T cells with exosomes that present on its surface a complex of an HLA antigen and a peptide of present invention; and
 (c) introducing into CD8-positive T cells one or more polynucleotides encoding a polypeptide(s) that can form a TCR capable of recognizing a complex of a peptide of present invention and an HLA antigen.

When a peptide(s), a polynucleotide(s), an exosome(s) or an APC(s) of the present invention is administered to a subject, CTLs are induced in the body of the subject and the strength of the immune response targeting MPHOSPH1-expressing cancer cells is enhanced. Therefore, the methods of the present invention may comprise a step of administering a peptide(s), a polynucleotide(s), an APC(s) or an exosome(s) of the present invention to a subject.

Alternatively, CTLs can be induced by using them in vitro or ex vivo. For example, the methods of the present invention may include the following steps:
(a) collecting APCs from a subject;
(b) contacting the APCs of step (a) with a peptide of the present invention; and
(c) co-culturing the APCs of step (b) with CD8-positive T cells.

The induced CTLs may be returned to the subject afterwards.

The APCs to be co-cultured with the CD8-positive T cells in step (c) above can also be prepared by introducing into APCs a polynucleotide encoding a peptide of the present invention as described above in the "VI. Antigen-presenting cells (APCs)" section. However, the APCs to be used in the methods of the present invention are not limited thereto, and any APCs that present on their surface a complex of an HLA antigen and a peptide of the present invention can be used.

In the methods of the present invention, instead of such APCs, exosomes that present on their surface a complex of an HLA antigen and a peptide of the present invention can also be used. That is, the methods of the present invention can comprise a step of co-culturing with exosomes that present on their surface a complex of an HLA antigen and a peptide of the present invention. Such exosomes can be prepared by the above-described methods in the "V. Exosomes" section.

Further, CTLs can also be induced by introducing into a CD8-positive T cell a vector comprising a polynucleotide encoding each subunit of a TCR capable of binding to a peptide of the present invention presented by an HLA antigen on the cell surface. Such transformation can be carried out as described above in the "VIII. T cell receptors (TCRs)" section.

Accordingly, in one embodiment, the present invention provides methods of inducing CTLs, comprising a step selected from below:
(a) co-culturing CD8-positive T cells with APCs that present on their surface a complex of an HLA antigen and a peptide of present invention;
(b) co-culturing CD8-positive T cells with exosomes that present on their surface a complex of an HLA antigen and a peptide of present invention; and
(c) introducing into CD8-positive T cells, a vector comprising a polynucleotide encoding each subunit of a TCR capable of binding to a peptide of the present invention presented by an HLA antigen on a cell surface.

The above-described methods can be performed in vitro, ex vivo, or in vivo, and it is preferable to perform them in vitro or ex vivo. APCs or exosomes and CD8-positive T cells used in the above-described methods may be derived from a subject scheduled for administration of the induced CTLs, or they may be derived from a different subject. When APCs or exosomes and CD8-positive T cells derived from a subject (donor) different from the subject scheduled for administration are used, the subject of administration and the donor must have the identical HLA type. For example, when a peptide having the amino acid sequence selected from among SEQ ID NOs: 5, 12, 27, 52, and 53 or a modified peptide thereof is used as peptides of the present invention, the HLA type in both the subject of administration and the donor is preferably HLA-A11 (more preferably HLA-A*11:01). Alternatively, APCs or exosomes used in the above-described methods are preferably APCs or exosomes that present on their surface a complex of HLA-A11 (more preferably HLA-A*11:01) and a peptide of the present invention (a peptide having the amino acid sequence selected from among SEQ ID NOs: 5, 12, 27, 52, and 53 or a modified peptide thereof). In this case, the induced CTLs show a specific cytotoxic activity against cells that present a complex of HLA-A11 and a peptide of the present invention (for example, MPHOSPH1-expressing HLA-A11-positive cells).

Alternatively, for example, when a peptide having the amino acid sequence selected from among SEQ ID NOs: 118, 119, and 170 or a modified peptide thereof is used as peptides of the present invention, the HLA in both the subject of administration and the donor is preferably HLA-A33 (more preferably HLA-A*33:03). Alternatively, APCs or exosomes used in the above-described methods are preferably APCs or exosomes that present on their surface a complex of HLA-A33 (more preferably HLA-A*33:03) and a peptide of the present invention (a peptide having the amino acid sequence selected from among SEQ ID NOs: 118, 119, and 170 or a modified peptide thereof). In this case, the induced CTLs show a specific cytotoxic activity against cells that present a complex of HLA-A33 and a peptide of the present invention (for example, MPHOSPH1-expressing HLA-A33-positive cells).

In another embodiment, the present invention also provides compositions or pharmaceutical compositions for inducing CTLs, comprising at least one active ingredient selected from below:
(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

In another embodiment, the present invention also provides use of an active ingredient selected from below in the manufacture of compositions or pharmaceutical compositions for inducing CTLs:
(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

Alternatively, the present invention further provides an active ingredient selected from below for use in inducing CTLs:
(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

Alternatively, the present invention further provides a method or process for manufacturing a composition or pharmaceutical composition for inducing CTLs, which is a method or process that comprises a step of formulating an active ingredient selected from below with a pharmaceutically or physiologically acceptable carrier:
(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

In another embodiment, the present invention further provides a method or process for manufacturing a composition or pharmaceutical composition for inducing CTLs, which is a method or process that comprises a step of mixing an active ingredient selected from below with a pharmaceutically or physiologically acceptable carrier:
(a) a peptide of the present invention:
(b) a polynucleotide encoding a peptide of the present invention in an expressible form;

(c) an APC that presents on its surface a peptide of the present invention; and
(d) an exosome that presents on its surface a peptide of the present invention.

XI. Methods of Inducing an Immune Response

The present invention further provides methods of inducing an immune response against MPHOSPH1-expressing cancers. Applicable cancers include bladder cancer, breast cancer, cervical cancer, cholangiocellular cancer, chronic myeloid leukemia (CML), colon cancer, gastric cancer, lung cancer, lymphoma, osteosarcoma, prostate cancer, kidney, soft tissue tumor and such, but are not limited thereto. It is preferable that the cancer expresses at least one HLA selected from among HLA-A11 and HLA-A33.

The present invention further provides methods of inducing an immune response against MPHOSPH1-expressing cancer cells. MPHOSPH1 is recognized to be overexpressed in various types of cancers described above. Thus, when an immune response against MPHOSPH1-expressing cancer cells is induced, proliferation of the cancer cells is inhibited as a result. Accordingly, the present invention further provides methods of inhibiting proliferation of MPHOSPH1-expressing cancer cells. The methods of the present invention are suitable, in particular, for inhibiting proliferation of cancer cells expressing MPHOSPH1 and at least one HLA selected from among HLA-A11 and HLA-A33.

The methods of the present invention may comprise a step of administering a composition comprising any of the peptides of the present invention or a polynucleotide(s) encoding the peptide(s). The methods of the present invention also contemplate administration of APCs or exosomes presenting any of the peptides of the present invention. The details can be referred to the "IX. Pharmaceutical compositions" section, particularly portions describing regarding use of the pharmaceutical compositions of the present invention as vaccines. In addition, exosomes and APCs that can be used in the methods of the present invention for inducing an immune response are described in detail in "V. Exosomes", "VI. Antigen-presenting cells (APCs)" and in Items (1) and (2) of "X. Methods of using peptides, exosomes. APCs and CTLs" described above.

In another embodiment, the present invention provides pharmaceutical compositions or vaccines for inducing an immune response against MPHOSPH1-expressing cancers, wherein the pharmaceutical composition or vaccine comprises an active ingredient selected from below:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention also provides pharmaceutical compositions or vaccines for inducing an immune response against MPHOSPH1-expressing cancer cells, wherein the pharmaceutical composition or vaccine comprises an active ingredient selected from below:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention further provides pharmaceutical compositions or vaccines for inhibiting proliferation of MPHOSPH1-expressing cancer cells, wherein the pharmaceutical composition or vaccine comprises an active ingredient selected from below:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

In another embodiment, the present invention provides use of an active ingredient selected from below in the manufacture of pharmaceutical compositions or vaccines for inducing an immune response against MPHOSPH1-expressing cancers:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention also provides use of an active ingredient selected from below in the manufacture of pharmaceutical compositions or vaccines for inducing an immune response against MPHOSPH1-expressing cancer cells:
(a) a peptide of the present invention:
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention further provides use of an active ingredient selected from below in the manufacture of pharmaceutical compositions or vaccines for inhibiting proliferation of MPHOSPH1-expressing cancer cells:
(a) a peptide of the present invention:
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

The present invention further provides methods or processes for manufacturing pharmaceutical compositions that induce an immune response against MPHOSPH1-expressing cancers, which is a method that may comprise a step of mixing or formulating a peptide of the present invention with a pharmaceutically acceptable carrier.

Alternatively, the present invention provides methods for inhibiting proliferation of MPHOSPH1-expressing cancer cells or methods of inducing an immune response against cancers, which comprises a step of administering to a subject vaccines or pharmaceutical compositions comprising an active ingredient selected from below:

(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

In the context of the present invention, MPHOSPH1-expressing cancers can be treated by administering a peptide, a polynucleotide, an APC, an exosome and/or a CTL of the present invention. Alternatively, an immune response against MPHOSPH1-expressing cancers can be induced by administering a peptide, a polynucleotide, an APC, an exosome and/or a CTL of the present invention. Examples of such cancers include bladder cancer, breast cancer, cervical cancer, cholangiocellular cancer, chronic myeloid leukemia (CML), colon cancer, gastric cancer, lung cancer, lymphoma, osteosarcoma, prostate cancer, kidney cancer, soft tissue tumor and such, but are not limited thereto. Further, an immune response against MPHOSPH1-expressing cancer cells can be induced by administering a peptide, a polynucleotide, an APC, an exosome and/or a CTL of the present invention. Therefore, before administering a vaccine or pharmaceutical composition comprising an active ingredient described above, it is preferable to confirm whether the level of MPHOSPH1 expression at a diseased site in the subject to be treated is augmented or not.

Thus, in one embodiment, the present invention provides a method of treating a MPHOSPH1-expressing cancer in a patient in need of the cancer treatment, wherein the method comprises the steps below:
(i) measuring the level of MPHOSPH1 expression in a biological sample collected from the diseased site of a subject with cancer;
(ii) identifying a subject with MPHOSPH1-expressing cancer based on the MPHOSPH1 expression level measured in (i); and
(iii) administering to a subject with a cancer overexpressing MPHOSPH1 as compared with a normal control at least one ingredient selected from the group consisting of (a) to (e) above.

Alternatively, the present invention further provides vaccines and pharmaceutical compositions comprising at least one active ingredient selected from the group consisting of (a) to (e) above for administration to a subject with MPHOSPH1-expressing cancer. The present invention further provides a method of identifying or selecting a subject to be treated with at least one active ingredient selected from the group consisting of (a) to (e) above, wherein the method comprises the steps below:
(i) measuring the level of MPHOSPH1 expression in a biological sample collected from the diseased site of a subject with cancer;
(ii) identifying a subject with MPHOSPH1-expressing cancer based on the MPHOSPH1 expression level measured in (i); and
(iii) identifying or selecting the subject identified in (ii) as a subject who may be treated with at least one active ingredient selected from the group consisting of (a) to (e) above.

Biological samples collected from a subject for measuring the MPHOSPH1 expression level in the above-described methods are not particularly limited, and for example, tissue samples containing cancer cells collected by biopsy or such can be preferably used. The MPHOSPH1 expression level in a biological sample can be measured by known methods, and for example, methods that detect transcription products of the MPHOSPH1 gene by probes or PCR methods (for example, cDNA microarray method, Northern blot method, RT-PCR method or such), methods that detect translation products of the MPHOSPH1 gene by antibodies or such (for example, Western blot method, immunostaining method or such), and such can be used. Further, biological samples may be blood samples, and in this case, the blood level of an antibody against MPHOSPH1 is measured, and the MPHOSPH1 expression level at a diseased site may be assessed based on the blood level. The blood level of an antibody against MPHOSPH1 can be measured using known methods, and for example, enzyme immunoassay (EIA), enzyme-linked immunosorbent assay (ELISA), radioimmunoassay (RIA) and such using the MPHOSPH1 protein or a peptide of the present invention as an antigen can be used.

Normally, in tissues and cells that do not express MPHOSPH1, there is almost no detection of MPHOSPH1 transcription products and translation products. Thus, when a transcription product or a translation product of MPHOSPH1 is detected in cancer cells or a tissue sample containing cancer cells collected from a subject, one can determine that the subject's cancer expresses MPHOSPH11. In blood samples of a subject that does not have MPHOSPH1-expressing cancer, there is almost no detection of antibodies against MPHOSPH1 or fragments thereof. Thus, when antibodies against MPHOSPH1 or fragments thereof are detected in a blood sample collected from a subject, one can determine that the subject's cancer expresses MPHOSPH1.

Whether a subject's cancer expresses MPHOSPH1 or not may also be determined by comparison with the measurement results of the same type of biological material collected from a non-cancerous site of the subject or the same type of biological material collected from a subject who does not have cancer (normal control sample). That is, in comparison with the level of the target of measurement in a normal control sample (normal control level), when the level in the biological sample of the test subject is elevated, the subject's cancer is assessed to be expressing MPHOSPH1. For example, when the amount of the target of measurement detected is increased by at least 10% or higher in comparison with the normal control level, the subject's cancer may be assessed to be expressing MPHOSPH1. It is desirable that the amount of the target of measurement detected is increased by preferably 25% or higher, and more preferably 50% or higher than the normal control level. Further, the amount of a transcription product or a translation product of MPHOSPH1 detected may be evaluated by normalizing against the detected amount of a known housekeeping gene such as beta-Actin, glyceraldehyde-3-phosphate dehydrogenase, or ribosomal protein P1.

In a preferred embodiment, it is preferable to confirm the HLA type of the subject before administering at least one active ingredient selected from the group consisting of (a) to (e) above. For example, for the subjects to be administered with an active ingredient in association with a peptide having the amino acid sequence selected from among SEQ ID NOs: 5, 12, 27, 52, and 53, it is preferable to select HLA-A11-positive subjects. For the subjects to be administered with an active ingredient in association with a peptide having the amino acid sequence selected from among SEQ ID NOs: 118, 119, and 170, it is preferable to select HLA-A33-positive subjects.

The present invention further provides complexes of a peptide of the present invention and HLA. The complexes of the present invention described above may be monomers or multimers. When a complex of the present invention is a multimer, the number of polymerization is not particularly limited, and it can be a multimer of any number of polymerization. Examples include a tetramer, pentamer, hexamer and such, but are not limited thereto. The multimers of the present invention also encompass dextramers (WO2002/072631) and streptamers (Knabel M et al., Nat Med. 2002 June; 8(6): 631-7.). Complexes of a peptide of the present invention and HLA can be prepared according to known methods (for example, Altman J D et al., Science. 1996, 274(5284): 94-6; WO2002/072631; WO2009/003492; Knabel M et al., Nat Med. 2002 June; 8(6): 631-7, and such).

The complexes of the present invention, for example, can be used in the quantification of CTLs specific to a peptide of the present invention. For example, a blood sample is collected from a subject administered with a pharmaceutical composition of the present invention, and CD4-negative cells are prepared after separation of PBMCs and contacted with a fluorescent dye-conjugated complex of the present invention. Then, the percentage of CTLs specific to a peptide of the present invention can be measured by flow cytometry analysis. For example, immune response-inducing effects by a pharmaceutical composition of the present invention can be monitored by measuring the specific CTLs against a peptide of the present invention before, during and/or after administration of the pharmaceutical composition of the present invention.

XII. Antibodies

The present invention further provides antibodies that bind to the peptide of the present invention. Preferable antibodies bind specifically to a peptide of the present invention, but do not bind (or weakly bind) to one that is not the peptide of the present invention. In another embodiment, such an antibody may include an antibody that recognizes a peptide in the context of HLA molecules, i.e., an antibody that binds to a peptide-MHC complex. The binding specificity of an antibody can be confirmed by inhibition assay. That is, if the binding between an antibody to be analyzed and a full-length MPHOSPH1 polypeptide is inhibited in the presence of a peptide of the present invention, this antibody is shown to specifically bind to the peptide of the present invention. Antibodies against peptides of the present invention can be used in assays of disease diagnosis and prognosis, as well as subject selection for administration of the pharmaceutical compositions of the present invention and monitoring of the pharmaceutical compositions of the present invention.

The present invention also provides various immunological assays for detecting and/or quantifying peptides of the present invention or fragments thereof. Such immunological assays include radioimmunoassay, immunochromatography, enzyme-linked immunosorbent assay (ELISA), enzyme-linked immunofluorescence assay (ELIFA) and such, without being limited thereto, and are performed within the scope of the various immunological assay formats well known in the art.

The antibodies of the present invention can be used in immunological imaging methods that can detect MPHOSPH1-expressing diseases, and examples thereof include radioactive scintigraphic imaging using a labelled antibody of the present invention, without being limited thereto. Such assay methods are used clinically in the detection, monitoring, and prognosis of MPHOSPH1-expressing cancers; and examples of such cancer include bladder cancer, breast cancer, cervical cancer, cholangiocellular cancer, chronic myeloid leukemia (CML), colon cancer, gastric cancer, lung cancer, lymphoma, osteosarcoma, prostate cancer, kidney cancer, soft tissue tumor and such, without being limited thereto.

The antibodies of the present invention can be used in any arbitrary form such as monoclonal antibodies or polyclonal antibodies, and may further include anti-sera obtained by immunizing an animal such as a rabbit with a peptide of the present invention, all classes of polyclonal antibodies and monoclonal antibodies, human antibodies, as well as chimeric antibodies and humanized antibodies generated through gene recombination.

The peptide of the present invention or a fragment thereof used as an antigen for obtaining antibodies can be obtained by chemical synthesis or genetic engineering techniques based on the amino acid sequences disclosed herein.

The peptide used as an immunizing antigen may be a peptide of the present invention or a fragment of a peptide of the present invention. Further, the peptide may be bound to or conjugated with a carrier for increasing immunogenicity. Keyhole limpet hemocyanin (KLH) is well-known as a carrier. Methods for binding KLH to a peptide are also well known in the art.

Any mammal can be immunized with an antigen described above, and it is preferable to consider the compatibility with the parent cell used in cell fusion when generating a monoclonal antibody. Generally, animals of the order Rodentia, Lagomorpha or Primate can be used. Animals of the order Rodentia include, for example, mice, rats and hamsters. Animals of the order Lagomorpha include, for example, rabbits. Animals of the order Primate include, for example, Catarrhini monkeys (old world monkeys) such as cynomolgus monkey (*Macaca fascicularis*), rhesus monkeys, hamadryas, and chimpanzee.

Methods of immunizing animals with an antigen are known in the art. Intraperitoneal injection and subcutaneous injection of an antigen are standard methods for immunizing mammals. More specifically, an antigen is diluted and suspended in an appropriate amount of phosphate buffered saline (PBS), physiological saline, or such. As needed, an antigen suspension solution can be administered to mammals after being mixed with an appropriate amount of a standard adjuvant such as Freund's complete adjuvant and emulsified. Then, it is preferable to administer the antigen mixed with an appropriate amount of a Freund's incomplete adjuvant several times every 4 to 21 days. A suitable carrier may be used for immunization. After the above immunization, the serum can be examined by standard method with respect to increase in the quantity of the desired antibody.

Polyclonal antibodies against a peptide of the present invention can be prepared by collecting blood from mammals that have been confirmed with an increase in the serum level of the desired antibody after immunization, and separating the serum from blood by any conventional method. A polyclonal antibody may be a polyclonal antibody-containing serum, or a polyclonal antibody-containing fraction may be isolated from the serum. Immunoglobulin G or M can be prepared from fractions that recognize only a peptide of the present invention by, for example, using an affinity column conjugated with the peptide of the present invention, and then further purifying the fractions using a protein A or protein G column.

In order to prepare monoclonal antibodies, upon confirming an increase in the serum level of the desired antibody after immunization, immune cells are collected from the mammals and subjected to cell fusion. Immune cells used for cell fusion may be preferably obtained from the spleen. For the other parent cells fused with the above immune cells, for example, a mammalian myeloma cell, and more preferably a myeloma cell that has acquired a property for drug selection of fusion cells can be used.

The above immune cells can be fused with myeloma cells by following known methods, for example, the method of Milstein et al. (Galfre and Milstein, Methods Enzymol, 1981, 73: 3-46).

Hybridomas obtained by cell fusion can be selected by culturing them in a standard selection medium such as the HAT medium (a medium containing hypoxanthine, aminopterin and thymidine). Cell culturing is typically continued in the HAT medium for a sufficient period of time (for example, several days to several weeks) to allow death of all other cells (non-fused cells) besides the desired hybridomas. Then, hybridoma cells producing the desired antibody can be screened and cloned by performing a standard limiting dilution.

In addition to the above methods of immunizing a non-human animal with an antigen for hybridoma preparation, human lymphocytes such as EB virus-infected lymphocytes can be immunized in vitro with a peptide, cells expressing the peptide, or lysates thereof. Then, the immunized lymphocytes can be fused with immortalized human-derived myeloma cells such as U266 to obtain hybridomas producing a desired human antibody capable of binding to the peptide (JPS63-17688).

Next, the obtained hybridoma is transplanted into the abdominal cavity of a mouse, and the ascites is extracted. The obtained monoclonal antibody can be purified by, for example, ammonium sulfate precipitation, protein A or protein G column, DEAE ion-exchange chromatography, or affinity column conjugated with the peptide of the present invention.

Alternatively, antibody-producing immune cells such as the immunized lymphocytes can be immortalized by a cancer gene and used for the preparation of monoclonal antibodies.

The monoclonal antibodies obtained as such can also be prepared by recombination using genetic engineering techniques (see, e.g., Borrebaeck and Larrick, Therapeutic Monoclonal Antibodies published in United Kingdom by MacMillan Publishers LTD (1990)). For example, an antibody-encoding DNA can be cloned from immune cells such as antibody-producing hybridoma or immunized lymphocytes and inserted into a suitable vector, and then this is introduced into host cells to prepare a recombinant antibody. The present invention also provides recombinant antibodies prepared as described above.

Further, the antibodies of the present invention may be antibody fragments or modified antibodies, as long as they bind to the peptides of the present invention. For example, it is desirable that the antibody fragment contains an antigen-binding site(s) of the antibodies. Specifically, the antibody fragments may be Fab, F(ab')$_2$, Fv, or a single chain Fv (scFv) in which Fv fragments derived from an H chain and an L chain are linked with a suitable linker (Huston et al., Proc Natl Acad Sci USA, 1988, 85: 5879-83). More specifically, antibody fragments may be generated by treating an antibody with an enzyme such as papain or pepsin. Alternatively, a gene encoding an antibody fragment may be constructed, inserted into an expression vector, and expressed in an appropriate host cell (see, e.g., Co et al., J Immunol, 1994, 152: 2968-76; Better and Horwitz, Methods Enzymol, 1989, 178: 476-96; Pluckthun and Skerra, Methods Enzymol, 1989, 178: 497-515; Lamoyi, Methods Enzymol, 1986, 121: 652-63; Rousseaux et al., Methods Enzymol, 1986, 121: 663-9; Bird and Walker, Trends Biotechnol, 1991, 9: 132-7).

Antibodies may be modified by conjugation with various molecules such as polyethyleneglycol (PEG). The present invention provides such modified antibodies. Modified antibodies can be obtained by chemically modifying the antibodies. These modification methods are conventional in the art.

Alternatively, the antibodies of the present invention can be obtained as chimeric antibodies of a non-human antibody-derived variable region and a human antibody-derived constant region, or as humanized antibodies comprising a non-human antibody-derived complementarity determining region (CDR) and a human antibody-derived framework region (FR) and constant region. Such antibodies can be prepared according to known techniques. Humanization can be carried out by substituting a human antibody sequence(s) with a corresponding non-human antibody CDR sequence(s) (see, e.g., Verhoeyen et al., Science, 1998, 239: 1534-6). Thus, such humanized antibodies are chimeric antibodies in which the substantially less than an intact human variable domain has been substituted with a corresponding sequence from a non-human species.

Intact human antibodies comprising a human variable region in addition to the human framework and constant regions can also be used. Such antibodies can be generated using various techniques known in the art. For example, in vitro methods include use of recombinant libraries of human antibody fragments presented on bacteriophages (for example, Hoogenboom & Winter, J. Mol. Biol., 1991, 227: 381). Similarly, human antibodies can also be generated by introducing human immunoglobulin gene loci into transgenic animals, for example, mice, in which the endogenous immunoglobulin genes have been partially or completely inactivated. This approach is described in, for example, U.S. Pat. Nos. 6,150,584, 5,545,807, 5,545,806, 5,569,825, 5,625,126, 5,633,425 and 5,661,016.

Antibodies obtained as described above may be purified to homogeneity. For example, antibody separation and purification can be performed according to separation methods and purification methods used for general proteins. For example, an antibody can be separated and isolated by appropriately selecting and combining use of column chromatographies such as affinity chromatography, filter, ultrafiltration, salting-out, dialysis, SDS-polyacrylamide gel electrophoresis and isoelectric focusing electrophoresis (Antibodies: A Laboratory Manual. Ed Harlow and David Lane, Cold Spring Harbor Laboratory (1988)), but are not limited thereto. Protein A column and protein G column can be used as the affinity column. Exemplary protein A columns to be used include, for example, Hyper D. POROS and Sepharose F.F. (Pharmacia).

Besides affinity chromatography, exemplary chromatography includes, for example, ion-exchange chromatography, hydrophobic chromatography, gel filtration, reversed-phase chromatography, adsorption chromatography and such (Strategies for Protein Purification and Characterization: A Laboratory Course Manual. Ed Daniel R. Marshak et al., Cold Spring Harbor Laboratory Press (1996)). The chromatography procedures can be carried out by liquid-phase chromatography such as HPLC and FPLC.

The antigen-binding activity of an antibody of the present invention can be measured, for example, by using absorbance measurement, enzyme-linked immunosorbent assay (ELISA), enzyme immunoassay (EIA), radioimmunoassay (RIA), and/or immunofluorescence (IF). In the case of ELISA, an antibody of the present invention is immobilized onto a plate, a peptide of the present invention is applied to the plate, and then a sample containing the desired antibody, such as culture supernatant of antibody-producing cells or purified antibodies, is applied. Next, a secondary antibody that recognizes the primary antibody and is labelled with an enzyme such as alkaline phosphatase is applied and the plate is incubated. Then, after washing, an enzyme substrate such as p-nitrophenyl phosphate is applied to the plate, and the antigen-binding activity of the sample is evaluated by measuring absorbance. To assess the binding activity of an antibody, peptide fragments such as C-terminal or N-terminal fragments may be used as an antigen. BIAcore (Pharmacia) may be used to evaluate the activity of an antibody of the present invention.

It is possible to detect or measure a peptide of the present invention using the above methods, by exposing an antibody of the present invention to a sample assumed to contain the peptide of the present invention, and detecting or measuring an immune complex formed between the antibody and the peptide.

For example, an antibody of the present invention can be used to detect a peptide of the present invention present in the blood sample (for example, serum sample) of a subject. Alternatively, an antibody of the present invention present in the blood sample (for example, serum sample) of a subject can also be detected using a peptide of the present invention. The result of measuring a peptide of the present invention or an antibody of the present invention in the blood sample of a subject can be utilized to the subject selection for administration of the pharmaceutical compositions of the present invention or monitoring of the efficacy of the pharmaceutical compositions of the present invention. In addition, it has been reported that patients having an antibody against a peptide administered as vaccine may have high responsiveness to the vaccine. Therefore, the peptide of the present invention can also be utilized as an immunoassay antigen for selecting, among cancer patients, a patient expected to show high responsiveness to a vaccine comprising the peptide using an antibody against the peptide as an index.

XIII. Vectors and Host Cells

The present invention provides vectors comprising a polynucleotide encoding a peptide of the present invention and host cells introduced with the vectors. A vector of the present invention may be used to keep a polynucleotide of the present invention in a host cell, to express a peptide of the present invention in a host cell, or to administer a polynucleotide of the present invention for gene therapy.

When *E. coli* is a host cell and a vector is amplified and produced in a large amount in *E. coli* (for example, JM109, DH5-alpha, HB101 or XL1-Blue), the vector needs to have a "replication origin" for amplification in *E. coli* and a marker gene for selection of transformed *E. coli* (for example, a drug resistance gene selected by a drug such as ampicillin, tetracycline, kanamycin, chloramphenicol). For example, the M13-series vectors, pUC-series vectors, pBR322, pBluescript, pCR-Script and such can be used. In addition, pGEM-T, pDIRECT and pT7 can be used for cloning as well as the above vectors. When a vector is used in the production of a peptide of the present invention, an expression vector can be used. For example, an expression vector for expression in *E. coli* needs to have the above features for amplification in *E. coli*. When *E. coli* such as JM09, DH5-alpha, HB101 or XL1-Blue are used as a host cell, the vector needs to have a promoter, for example, lacZ promoter (Ward et al., Nature, 1989, 341: 544-6; FASEB J, 1989, 6: 2422-7), araB promoter (Better et al., Science, 1988, 240: 1041-3), T7 promoter or the like, that can efficiently express the desired gene in *E. coli*. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may contain a signal sequence for peptide secretion. An exemplary signal sequence that directs the peptide to be secreted to the periplasm of the *E. coli* is the pelB signal sequence (Lei et al., J Bacteriol, 1987, 169: 4379). Means for introducing the vectors into the target host cells include, for example, the calcium chloride method and the electroporation method.

In addition to *E. coli*, for example, expression vectors derived from mammals (for example, pcDNA3 (Invitrogen) and pEGF-BOS (Nucleic Acids Res, 1990, 18(17): 5322), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vectors derived from yeast (e.g., "Pichia Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells such as CHO, COS or NIH3T3 cells, the vector needs to carry a promoter necessary for expression in such cells, for example, the SV40 promoter (Mulligan et al., Nature, 1979, 277: 108), the MMLV-LTR promoter, the EF1-alpha promoter (Mizushima et al., Nucleic Acids Res, 1990, 18: 5322), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

The embodiments of the present invention are exemplified below based on the above explanation; however, the present invention is not limited to these embodiments.

[1] A peptide of less than 15 amino acids having cytotoxic T cell (CTL)-inducing ability, which comprises the amino acid sequence selected from the group of:
  (a) the amino acid sequence selected from the group consisting of SEQ ID NOs: 5, 12, 27, 52, 53, 118, 119, and 170; and
  (b) the amino acid sequence in which one, two or several amino acids are substituted, deleted, inserted and/or added to the amino acid sequence selected from the group consisting of SEQ ID NOs: 5, 12, 27, 52, 53, 118, 119, and 170.

[2] The peptide of [1], which is selected from the group consisting of (i) to (ii) below:
  (i) a peptide comprising the amino acid sequence comprising one or more substitution(s) selected from (a) to (d) below introduced into the amino acid sequence selected from the group consisting of SEQ ID NOs: 5, 12, 27, 52, and 53:
    (a) the second amino acid from the N terminus is substituted with an amino acid selected from the group consisting of threonine, valine, isoleucine, leucine, phenylalanine and tyrosine;
(b) the third amino acid from the N terminus is substituted with an amino acid selected from the group consisting of leucine, phenylalanine, tyrosine, isoleucine and alanine;
(c) the seventh amino acid from the N terminus is substituted with an amino acid selected from the group consisting of leucine, isoleucine, tyrosine, valine and phenylalanine; and
(d) the C-terminal amino acid is substituted with arginine; and
(ii) a peptide comprising the amino acid sequence comprising one or more substitution(s) selected from (a) to (c) below introduced into the amino acid sequence selected from the group consisting of SEQ ID NOs: 118, 119, and 170:
(a) the first amino acid from the N terminus is substituted with an amino acid selected from the group consisting of aspartic acid and glutamic acid;
(b) the second amino acid from the N terminus is substituted with an amino acid selected from the group consisting of phenylalanine, tyrosine, alanine, isoleucine, leucine, and valine; and
(c) the C-terminal amino acid is substituted with lysine.

[3] The peptide of [1], which consists of the amino acid sequence selected from the group consisting of SEQ ID NOs: 5, 12, 27, 52, 53, 118, 119, and 170.

[4] A polynucleotide, which encodes the peptide of any one of [1] to [3].

[5] A composition comprising a pharmaceutically acceptable carrier and at least one ingredient selected from the group consisting of (a) to (e) below:
(a) one or more types of peptides of any one of [1] to [3];
(b) one or more types of polynucleotides encoding the peptide(s) of any one of [1] to [3] in an expressible form;
(c) an antigen-presenting cell (APC) that presents on its cell surface a complex of the peptide of any one of [1] to [3] and an HLA antigen;
(d) an exosome that presents on its cell surface a complex of the peptide of any one of [1] to [3] and an HLA antigen; and
(e) a CTL that targets the peptide of any one of [1] to [3].

[6] The composition of [5], which is a composition for inducing a CTL(s), wherein the ingredient is at least one ingredient selected from the group consisting of (a) to (d) below:
(a) one or more types of peptides of any one of [1] to [3];
(b) one or more types of polynucleotides encoding the peptide(s) of any one of [1] to [3] in an expressible form;
(c) an antigen-presenting cell (APC) that presents on its cell surface a complex of the peptide of any one of [1] to [3] and an HLA antigen; and
(d) an exosome that presents on its cell surface a complex of the peptide of any one of [1] to 131 and an HLA antigen.

[7] The composition of [5], which is a pharmaceutical composition.

[8] The composition of [7], which is pharmaceutical composition for one or more uses selected from the group consisting of (i) cancer treatment. (ii) cancer prevention (prophylaxis) and (iii) prevention (prophylaxis) of postoperative cancer recurrence.

[9] The composition of [7], which is for inducing an immune response against cancer.

[10] The composition of [8] or [9], wherein the cancer is selected from the group consisting of bladder cancer, breast cancer, cervical cancer, cholangiocellular cancer, chronic myeloid leukemia (CML), colon cancer, gastric cancer, lung cancer, lymphoma, osteosarcoma, prostate cancer, kidney cancer, and soft tissue tumor.

[11] The composition of any one of [5] to [10], which is formulated for administration to a subject positive for at least one HLA selected from the group consisting of HLA-A11 and HLA-A33.

[12] A method of inducing an APC(s) having CTL-inducing ability, which comprises a step selected from the group consisting of the following:
(a) contacting an APC(s) with the peptide of any one of [1] to [3] in vitro, ex vivo or in vivo; and
(b) introducing a polynucleotide encoding the peptide of any one of [1] to [3] into an APC(s).

[13] A method of inducing a CTL(s), which comprises a step selected from the group consisting of (a) to (c) below:
(a) co-culturing a CD8-positive T cell(s) with an APC(s) that presents on its surface a complex of an HLA antigen and the peptide of any one of [1] to [3];
(b) co-culturing a CD8-positive T cell(s) with an exosome (s) that presents on its surface a complex of an HLA antigen and the peptide of any one of [1] to [3]; and
(c) introducing into a CD8-positive T cell(s) a polynucleotide encoding each subunit of a T cell receptor (TCR) capable of binding to the peptide of any one of [1] to [3] presented by an HLA antigen on a cell surface.

[14] An APC that presents on its surface a complex of an HLA antigen and the peptide of any one of [1] to [3].

[15] The APC of [14], which is induced by the method of [12].

[16] A CTL that targets the peptide of any one of [1] to [3].

[17] The CTL of [16], which is induced by the method of [13].

[18] A method of inducing an immune response against cancer, which comprises administering to a subject at least one ingredient selected from the group consisting of (a) to (e) below:
(a) one or more types of peptides of any one of [1] to [3];
(b) one or more types of polynucleotides encoding the peptide(s) of any one of [1] to [3] in an expressible form;
(c) an antigen-presenting cell (APC) that presents on its cell surface a complex of the peptide of any one of [1] to [3] and an HLA antigen;
(d) an exosome that presents on its cell surface a complex of the peptide of any one of [1] to [3] and an HLA antigen; and
(e) a CTL that targets the peptide of any one of [1] to [3].

[19] A method of treating and/or preventing cancer, and/or preventing postoperative recurrence thereof, which comprises administering to a subject at least one ingredient selected from the group consisting of (a) to (e) below:
(a) one or more types of peptides of any one of [1] to [3];
(b) one or more types of polynucleotides encoding the peptide(s) of any one of [1] to [3] in an expressible form;
(c) an antigen-presenting cell (APC) that presents on its cell surface a complex of the peptide of any one of [1] to [3] and an HLA antigen;

(d) an exosome that presents on its cell surface a complex of the peptide of any one of [1] to [3] and an HLA antigen; and (e) a CTL that targets the peptide of any one of [1] to [3].

[20] An antibody that binds to the peptide of any one of [1] to [3].

[21] A method of screening for a peptide having CTL-inducing ability, which comprises the steps of:

(a) generating candidate sequences consisting of an amino acid sequence in which one, two or several amino acid residues are substituted, deleted, inserted and/or added to an original amino acid sequence consisting of the amino acid sequence selected from the group consisting of SEQ ID NOs: 5, 12, 27, 52, 53, 118, 119, and 170;

(b) selecting from among the candidate sequences generated in (a), a candidate sequence that does not have significant homology (sequence identity) with any known human gene product other than MPHOSPH1;

(c) contacting an APC(s) with a peptide consisting of the candidate sequence selected in (b);

(d) contacting the APC(s) of (c) with a CD8-positive T cell(s); and (e) selecting a peptide having an equal to or higher CTL-inducing ability than that of a peptide consisting of the original amino acid sequence.

[22] Use of at least one active ingredient selected from the group consisting of (a) to (e) below in the manufacture of a composition for inducing an immune response against cancer:

(a) one or more types of peptides of any one of [1] to [3]

(b) one or more types of polynucleotides encoding the peptide(s) of any one of [1] to [3] in an expressible form;

(c) an antigen-presenting cell (APC) that presents on its cell surface a complex of the peptide of any one of [1] to [3] and an HLA antigen;

(d) an exosome that presents on its cell surface a complex of the peptide of any one of [1] to [3] and an HLA antigen; and (e) a CTL that targets the peptide of any one of [1] to [3].

[23] Use of at least one ingredient selected from the group consisting of (a) to (e) below in the manufacture of a pharmaceutical composition for treating and/or preventing cancer, and/or preventing postoperative recurrence thereof:

(a) one or more types of peptides of any one of [1] to [3];

(b) one or more types of polynucleotides encoding the peptide(s) of any one of [1] to [3] in an expressible form;

(c) an antigen-presenting cell (APC) that presents on its cell surface a complex of the peptide of any one of [1] to [3] and an HLA antigen;

(d) an exosome that presents on its cell surface a complex of the peptide of any one of [1] to [3] and an HLA antigen; and (e) a CTL that targets the peptide of any one of [1] to [3].

[24] Use of at least one ingredient selected from the group consisting of (a) to (e) below for inducing an immune response against cancer:

(a) one or more types of peptides of any one of [1] to [3];

(b) one or more types of polynucleotides encoding the peptide(s) of any one of [1] to [3] in an expressible form;

(c) an antigen-presenting cell (APC) that presents on its cell surface a complex of the peptide of any one of [1] to [3] and an HLA antigen;

(d) an exosome that presents on its cell surface a complex of the peptide of any one of [1] to [3] and an HLA antigen; and (e) a CTL that targets the peptide of any one of [1] to [3].

[25] Use of at least one ingredient selected from the group consisting of (a) to (e) below for treating and/or preventing cancer and/or preventing postoperative recurrence thereof:

(a) one or more types of peptides of any one of [1] to [3];

(b) one or more types of polynucleotides encoding the peptide(s) of any one of [1] to [3] in an expressible form;

(c) an antigen-presenting cell (APC) that presents on its cell surface a complex of the peptide of any one of [1] to [3] and an HLA antigen;

(d) an exosome that presents on its cell surface a complex of the peptide of any one of [1] to [3] and an HLA antigen; and (e) a CTL that targets the peptide of any one of [1] to [3].

[26] A method of inducing cytotoxic activity against an MPHOSPH1-expressing cell(s), which comprises a step of administering to a subject at least one ingredient selected from the group consisting of (a) to (e) below:

(a) one or more types of peptides of any one of [1] to [3];

(b) one or more types of polynucleotides encoding the peptide(s) of any one of [1] to [3] in an expressible form;

(c) an antigen-presenting cell (APC) that presents on its cell surface a complex of the peptide of any one of [1] to [3] and an HLA antigen;

(d) an exosome that presents on its cell surface a complex of the peptide of any one of [1] to [3] and an HLA antigen; and (e) a CTL that targets the peptide of any one of [1] to [3].

[27] A freeze-dried formulation comprising one or more types of peptides of any one of [1] to [3].

[28] A pharmaceutical composition, which is prepared by a method that comprises dissolving one or more types of peptides of any one of [1] to [3] in a water-soluble carrier, and performing filtration sterilization.

[29] A filtration-sterilized aqueous solution, which is an aqueous solution that comprises one or more types of peptides of any one of [1] to [3] and a water-soluble carrier.

[30] An emulsion comprising one or more types of peptides of any one of [1] to [3], a water-soluble carrier and an oil adjuvant.

[31] A kit comprising a container that houses the pharmaceutical composition of any one of [5] to [11] and a container that houses an adjuvant.

[32] A kit comprising a container that stores a freeze-dried formulation comprising the peptide of any one of [1] to [3], a container that stores an adjuvant, and a container that stores a re-dissolving solution for the freeze-dried formulation.

The present invention is explained herein in detail with reference to its specific embodiments. However, it should be understood that the above explanation is in fact an illustrative and explanatory explanation, and is intended to explain the present invention and preferred embodiments thereof. Through routine experimentation, one skilled in the art will readily recognize that various changes and modifications can be made therein without departing from the spirit and scope of the present invention. Thus, the present invention is not confined to the above explanation, but is intended to be defined by the appended claims and equivalents thereto.

Hereinbelow, the present invention is described in more detail with reference to the Examples. Nevertheless, while the following materials, method and Examples may serve to assist one of ordinary skill in making and using certain embodiments of the present invention, there are only intended to illustrate aspects of the present invention and thus in no way to limit the scope of the present invention. One of ordinary skill in the art can use methods and materials similar or equivalent to those described herein in the practice or testing of the present invention.

All prior art documents cited herein are incorporated by reference in the present specification.

EXAMPLES

Example 1

Materials and Methods
Cell Lines

C1R cells, an HLA-A- and HLA-B-negative human B lymphoblastoid cell line, and COS7 cells, an African green monkey kidney cell line, were purchased from ATCC.
Generation of Target Cells with Steady HLA-A*11:01 Expression C1R cells (C1R-A11) that steadily express HLA-A*11:01 were used as cells that stimulate CTLs. A cDNA encoding the HLA-A*11:01 gene was amplified by PCR and incorporated into an expression vector. C1R cells into which the HLA-A*11:01 gene expression vector was introduced were cultured under drug selection for two weeks in medium containing G418 (Invitrogen). The G418-resistant C1R cell suspension was diluted, seeded in a 96-well plate, and further selectively cultured for 30 days in a G418-containing medium. The HLA-A*11:01 expression in C1R cells was verified by flow cytometric analysis.
Selection of MPHOSPH1-Derived Peptides MPHOSPH1-derived 9mer and 10mer peptides that are expected to bind to the HLA-A*11:01 molecule were determined using the binding prediction server "NetMHC 3.2" (www.cbs.dtu.dk/services/NetMHC-3.2/) (Buus et al., Tissue Antigens. 2003, 62(5): 378-84; Nielsen et al., Protein Sci. 2003, 12(5): 1007-17; Bioinformatics. 2004, 20(9): 1388-97).
Peptide Synthesis The peptides were synthesized by American Peptide Company (Sunnyvale, Calif.) according to a standard solid-phase synthesis method, and purified by reversed phase high-performance liquid chromatography (HPLC). The quality of the peptides (purity of 90% or higher) was guaranteed by HPLC and mass spectrometry. The peptides were dissolved with dimethylsulfoxide (final concentration: 20 mg/ml) and stored at −80 degrees C.
In Vitro CTL Induction Monocyte-derived dendritic cells (DCs) were used as the antigen-presenting cell to induce a specific cytotoxic T lymphocyte (CTL) response against peptides presented on human leukocyte antigens (HLAs). As already reported in literatures, DCs were generated in vitro (Nakahara S et al., Cancer Res 2003, 63(14): 4112-8). Specifically, peripheral-blood mononuclear cells (PBMCs) collected from healthy volunteers (HLA-A*11:01-positive) with the Ficoll-Paque plus solution (Pharmacia) were seeded in plastic tissue culture dishes (Corning) to let the monocytes in the PBMCs adhere to the dishes. This was cultured in the presence of 1000 IU/ml granulocyte macrophage colony-stimulating factor (R&D System) and 1000 IU/ml interleukin (IL)-4 (R&D System) for seven days. An AIM-V medium (Invitrogen) containing 5% inactivated AB-type serum (ABS) was used as the medium. DCs that were induced to differentiate from monocytes using the cytokines were pulsed with 20 micro-g/ml of each synthesized peptide (37 degrees C., three hours). Peptide pulsing was carried out in an AIM-V medium containing 3 micro-g/ml beta 2-microglobulin. These peptide-pulsed DCs were inactivated by X-ray irradiation (20 Gy), mixed in a 1:20 ratio with autologous CD8 positive T cells obtained by positive selection using the CD8 Positive Isolation Kit (Invitrogen) ($1.5 \times 10^4$ DCs and $3 \times 10^5$ CD8 positive T cells), and cultured in a 48-well plate (Corning). Each well contained 0.5 ml of the 5% ABS/AIM-V medium, and IL-7 (R&D System) was added thereto (final concentration: 10 ng/ml). Two days after the start of the culture, IL-2 (Novartis) was added (final concentration: 20 IU/ml). On day 7 and day 14 of culture, the CD8 positive T cells were further stimulated with peptide-pulsed DCs. The DCs were prepared at the time of use by the same method as above. After day 21 (after three DC stimulations), IFN-gamma production against the peptide-pulsed C1R-A11 was confirmed using human interferon (IFN)-gamma enzyme-linked immunospot (ELISPOT) assay (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).
CTL Propagation Procedure CTLs were propagated using methods similar to those reported by Riddell et al. (Walter E A et al., N Engl J Med 1995, 333(16): 1038-44; Riddell S R et al., Nat Med 1996, 2(2): 216-23). The CTLs were cultured in 25 ml 5% ABS/AIM-V medium together with two types of Mitomycin C-treated human B lymphoblastoid cell lines ($5 \times 10^6$ cells/25 ml medium each) and an anti-CD3 antibody (final concentration: 40 ng/ml). On the day after beginning of the culturing, IL-2 (final concentration: 120 IU/ml) was added to the culture. On days 5, 8 and 11, the medium was changed to a 5% ABS/AIM-V medium containing IL-2 (final concentration: 30 IU/ml) (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).
Establishment of CTL Clones After induction of CTLs in vitro, the CTLs were seeded onto 96 round-bottomed microtiter plates (Nalge Nunc International) at 1 cell/well or 10 cells/well. The CTLs were cultured with two types of Mitomycin C-treated human B lymphoblastoid cell lines ($1 \times 10^4$ cells/well each) in a total of 150 micro-l/well 5% ABS/AIM-V medium with an anti-CD3 antibody (final concentration: 30 ng/ml) and IL-2 (final concentration: 125 IU/ml). Ten days later, 50 micro-l5% ABS/AIM-V medium containing 500 IU/ml IL-2 was added to the culture. On day 14 or after. CTLs that showed peptide-specific IFN-gamma production in an ELISPOT assay were propagated using the same method as described above (Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).
Confirmation of IFN-Gamma Production To confirm the peptide-specific IFN-gamma production of CTLs induced with a peptide, an IFN-gamma ELISPOT assay and an IFN-gamma ELISA were performed. Peptide-pulsed C1R-A11 ($1 \times 10^4$ cells/well) was prepared as the target cell. The IFN-gamma ELISPOT assay and IFN-gamma ELISA were performed according to the assay kit manufacturer's manual.

Preparation of Target Cells Forcibly Expressing MPHOSPH1 and HLA-A*11:01

A cDNA encoding the MPHOSPH1 or HLA-A*11:01 gene was amplified by PCR. The PCR-amplified product was each incorporated into an expression vector. Either or both of the MPHOSPH1 gene-expressing vector and the HLA-A*11:01 gene-expressing vector were introduced into COS7, which is a cell line negative for HLA, using Lipofectamine 2000 (Invitrogen) following the manufacturer's recommended protocol. On the day after gene introduction, COS7 cells were detached and harvested using versene (Invitrogen), and used as the target cell for confirmation of IFN-gamma production ($5 \times 10^4$ cells/well).

Results

Prediction of MPHOSPH1-Derived HLA-A*11:01-Binding Peptides

Tables 1a and 1b show MPHOSPH1-derived 9mer peptides and 10mer peptides that have been predicted to bind to HLA-A*11:01 by "NetMHC 3.2" in the descending order of binding affinity. A total of 117 peptides that potentially have an HLA-A*11:01-binding ability was used as epitope peptide candidates.

TABLE 1a

HLA-A*11:01-binding 9mer peptides derived from MPHOSPH1

| Start position | Amino acid sequence | Kd (nM) | SEQ ID NO |
|---|---|---|---|
| 109 | MAQKFSFSK | 8 | 1 |
| 1112 | LTQGVTCYK | 9 | 2 |
| 1426 | KMMLITQAK | 11 | 3 |
| 739 | TINEFQNLK | 12 | 4 |
| 762 | TSSLIINNK | 13 | 5 |
| 186 | RLYTKMNLK | 15 | 6 |
| 1547 | TSFEISRNK | 15 | 7 |
| 350 | RSHSIFTVK | 18 | 8 |
| 104 | KSSGQMAQK | 18 | 9 |
| 940 | SQIKLMHTK | 18 | 10 |
| 903 | AIAELHVQK | 19 | 11 |
| 1227 | SSARTQNLK | 19 | 12 |
| 747 | KSHMENTFK | 24 | 13 |
| 182 | SLQERLYTK | 24 | 14 |
| 1495 | ALISSNVQK | 25 | 15 |
| 640 | AIFKDLVGK | 26 | 16 |
| 935 | ITNNVSQIK | 30 | 17 |
| 404 | NTSLLTLGK | 32 | 18 |
| 1702 | SILQSKAKK | 39 | 19 |
| 565 | KAFISHEEK | 40 | 20 |
| 1657 | KVAIRPSSK | 43 | 21 |
| 1192 | LTNNLQDMK | 58 | 22 |

TABLE 1a-continued

HLA-A*11:01-binding 9mer peptides derived from MPHOSPH1

| Start position | Amino acid sequence | Kd (nM) | SEQ ID NO |
|---|---|---|---|
| 1678 | GVNLATKKK | 63 | 23 |
| 1719 | KLSNVEASK | 65 | 24 |
| 814 | SSAITEDQK | 71 | 25 |
| 1134 | KVECSHSAK | 76 | 26 |
| 96 | CILGRLSEK | 86 | 27 |
| 1658 | VAIRPSSKK | 86 | 28 |
| 216 | KSALLRQIK | 87 | 29 |
| 290 | VSSKFQKRK | 132 | 30 |
| 1522 | TQIMDIKPK | 136 | 31 |
| 1711 | IIETMSSSK | 138 | 32 |
| 441 | QSFFNGKGK | 148 | 33 |
| 1277 | RIKINELEK | 179 | 34 |
| 503 | SLDSNSNSK | 197 | 35 |
| 1486 | VAALEIQLK | 200 | 36 |
| 1531 | RISSADPDK | 201 | 37 |
| 1048 | LQAEVKGYK | 266 | 38 |
| 1753 | GQVILMDQK | 273 | 39 |
| 1463 | ILTAQLTEK | 275 | 40 |
| 1279 | KINELEKKK | 297 | 41 |
| 1098 | QIQHVVEGK | 300 | 42 |
| 1607 | TVKIPKARK | 336 | 43 |
| 1116 | VTCYKAKIK | 390 | 44 |
| 776 | TVEVPKDSK | 398 | 45 |
| 213 | IASKSALLR | 404 | 46 |
| 784 | KSKICSERK | 427 | 47 |
| 1663 | SSKKTYSLR | 428 | 48 |
| 1676 | IIGVNLATK | 449 | 49 |
| 439 | YFQSFFNGK | 480 | 50 |
| 1322 | RACKDLNVK | 483 | 51 |

Start position indicates the number of amino acid residue from the N terminus of MPHOSPH1.
The dissociation constant [Kd (nM)] is derived from "NetMHC3.2".

TABLE 1b

HLA-A*11:01-binding 10mer peptides derived from MPHOSPH1

| Start position | Amino acid sequence | Kd (nM) | SEQ ID NO |
|---|---|---|---|
| 1546 | STSFEISRNK | 8 | 52 |
| 1675 | SIIGVNLATK | 13 | 53 |
| 1226 | ASSARTQNLK | 14 | 54 |
| 1603 | TTPVTVKIPK | 15 | 55 |
| 934 | SITNNVSQIK | 18 | 56 |
| 149 | FTYGLTNSGK | 19 | 57 |
| 1710 | MIIETMSSSK | 23 | 58 |
| 117 | KVFGPATTQK | 35 | 59 |
| 108 | QMAQKFSFSK | 35 | 60 |
| 502 | VSLDSNSNSK | 43 | 61 |
| 1725 | ASKENVSQPK | 44 | 62 |
| 1494 | KALISSNVQK | 52 | 63 |
| 1657 | KVAIRPSSKK | 59 | 64 |
| 813 | VSSAITEDQK | 61 | 65 |
| 133 | IMQPVKDLLK | 64 | 66 |
| 761 | DTSSLIINNK | 64 | 67 |
| 181 | DSLQERLYTK | 72 | 68 |
| 814 | SSAITEDQKK | 72 | 69 |
| 1485 | LVAALEIQLK | 73 | 70 |
| 287 | FVPVSSKFQK | 79 | 71 |
| 939 | VSQIKLMHTK | 86 | 72 |
| 639 | LAIFKDLVGK | 97 | 73 |
| 902 | IAIAELHVQK | 100 | 74 |
| 64 | RIRPFTQSEK | 111 | 75 |
| 47 | NTEANSFESK | 114 | 76 |
| 738 | DTINEFQNLK | 117 | 77 |
| 1754 | QVILMDQKMK | 119 | 78 |
| 507 | NSNSKILNVK | 140 | 79 |
| 83 | ILDSQTVVLK | 141 | 80 |
| 1768 | QIIKRRLRTK | 147 | 81 |
| 1111 | ELTQGVTCYK | 150 | 82 |
| 1462 | EILTAQLTEK | 157 | 83 |
| 1644 | ISDDRNSSVK | 184 | 84 |
| 1585 | IQFTPLQPNK | 185 | 85 |
| 1447 | YAEDRERFFK | 192 | 86 |
| 850 | FLLTIENELK | 195 | 87 |
| 988 | LLGNDYLVSK | 196 | 88 |
| 245 | NISEFEESIK | 207 | 90 |
| 1097 | VQIQHVVEGK | 210 | 91 |
| 575 | KLLDLIEDLK | 217 | 92 |
| 1468 | LTEKDSDLQK | 217 | 93 |
| 708 | LIQELETSNK | 231 | 94 |
| 1153 | IILKLERNLK | 234 | 95 |
| 1277 | RIKINELEKK | 236 | 96 |
| 413 | CINVLKNSEK | 244 | 97 |
| 15 | YVFSADPIAR | 249 | 98 |
| 1366 | ATELEKWKEK | 265 | 99 |
| 1316 | AIQQYERACK | 279 | 100 |
| 440 | FQSFFNGKGK | 282 | 101 |
| 686 | KTKGELIKTK | 284 | 102 |
| 1115 | GVTCYKAKIK | 289 | 103 |
| 377 | SLCDLAGSER | 303 | 104 |
| 576 | LLDLIEDLKK | 325 | 105 |
| 718 | KIITQNQRIK | 337 | 106 |
| 177 | NVLFDSLQER | 339 | 107 |
| 1606 | VTVKIPKARK | 351 | 108 |
| 273 | VSFPEIYNEY | 358 | 109 |
| 298 | KMLRLSQDVK | 371 | 110 |
| 322 | DSKEAYRLLK | 376 | 111 |
| 1047 | KLQAEVKGYK | 389 | 112 |
| 875 | FQQELSLSEK | 396 | 113 |
| 1251 | KLTDAKKQIK | 441 | 114 |
| 1676 | IIGVNLATKK | 449 | 115 |
| 1191 | QLTNNLQDMK | 465 | 116 |
| 469 | VLKFSAIAQK | 466 | 117 |

Start position indicates the number of amino acid residue from the N terminus of MPHOSPH1.
The dissociation constant [Kd (nM)] is derived from "NetMHC3.2".

Figure 1:
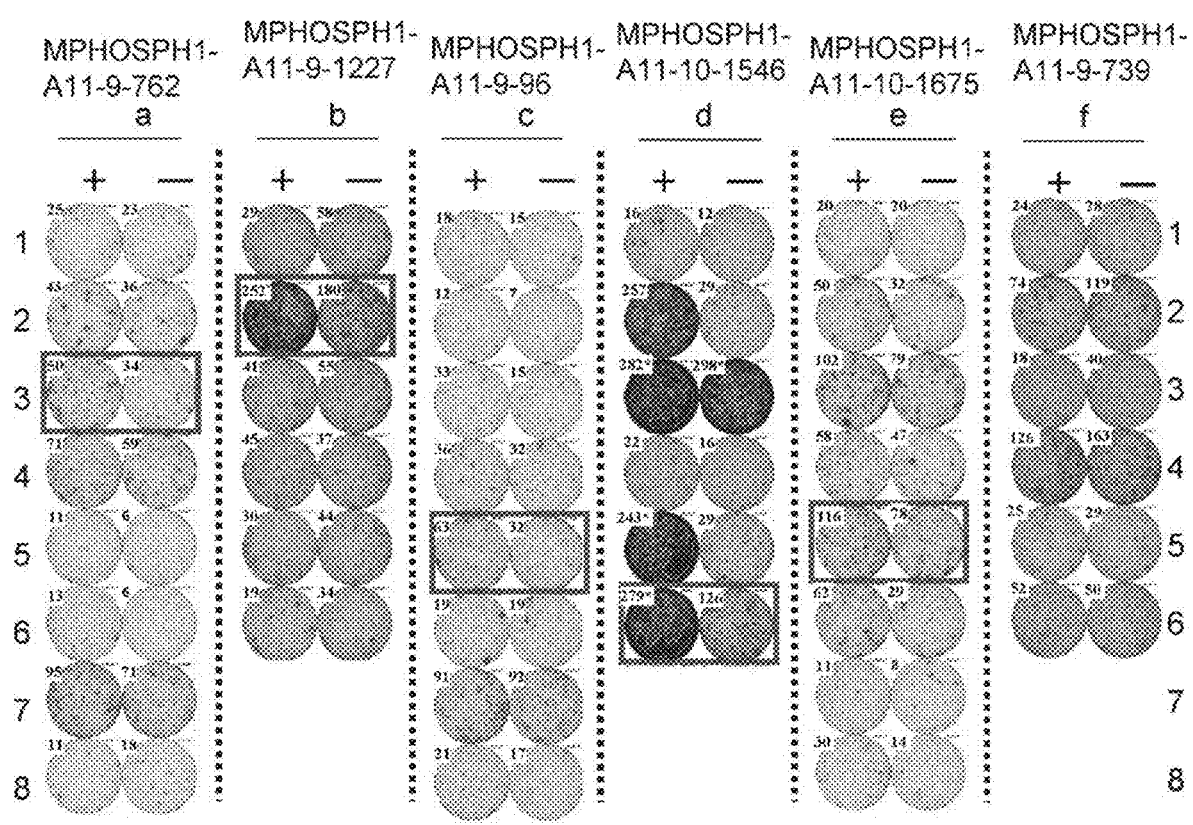
FIG. 1 consists of photos (a) to (f) showing results of an interferon (IFN)-gamma enzyme-linked immunospot (ELISPOT) assay performed using cells induced with peptides derived from MPHOSPH1. In the figure, "+" shows IFN-gamma production against target cells pulsed with a peptide of interest; and "−" shows IFN-gamma production against target cells that have not been pulsed with any peptide (negative controls). It can be seen by comparison with the negative controls that peptide-specific IFN-gamma was observed in Well #3 with MPHOSPH1-A11-9-762 (SEQ ID NO: 5) (a), Well #2 with MPHOSPH1-A11-9-1227 (SEQ ID NO: 12) (b), Well #5 with MPHOSPH1-A11-9-96 (SEQ ID NO: 27) (c), Well #6 with MPHOSPH1-A11-10-1546 (SEQ ID NO: 52) (d), and Well #5 with MPHOSPH1-A11-10-1675 (SEQ ID NO: 53) (e). Cells that showed a reaction, boxed in the photos, were proliferated to establish a CTL line. Meanwhile, MPHOSPH1-A11-9-739 (SEQ ID NO: 4) (f) is shown as an example of typical negative data in which peptide-specific IFN-gamma production was not observed.

Induction of CTLs by the Predicted MPHOSPH1-Derived HLA-A*11:01-Restricted Peptides MPHOSPH1-derived peptide-specific CTLs were induced according to the protocol described in "Materials and methods". The peptide-specific IFN-gamma production was confirmed by an ELISPOT assay (FIG. 1). Peptide-specific IFN-gamma production was observed in Well #3 with MPHOSPH1-A11-9-762 (SEQ ID NO: 5) (a), Well #2 with MPHOSPH1-A11-9-1227 (SEQ ID NO: 12) (b), Well #5 with MPHOSPH1-A11-9-96 (SEQ ID NO: 27) (c), Well #6 with MPHOSPH1-A11-10-1546 (SEQ ID NO: 52) (d), and Well #5 with MPHOSPH1-A11-10-1675 (SEQ ID NO: 53) (e). Meanwhile, specific IFN-gamma production against other peptides shown in Tables 1a and 1b was not observed. For example, specific IFN-gamma production was not observed against MPHOSPH1-A11-9-739 (SEQ ID NO: 4) (f). As a result, although all the peptides had the potential of binding to HLA-A*11:01, five peptides were selected as peptides having CTL-inducing ability.

Figure 2:
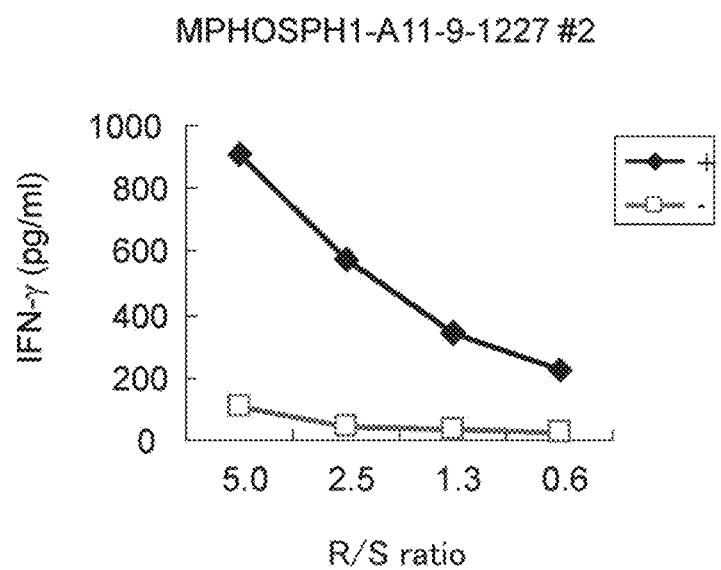
FIG. 2 consists of line graphs (a) to (b) showing results of measuring IFN-gamma produced by a CTL line stimulated with MPHOSPH1-A11-9-1227 (SEQ ID NO: 12) (a) or MPHOSPH1-A11-10-1546 (SEQ ID NO: 52) (b), using IFN-gamma enzyme-linked immunosorbent assay (ELISA). These results show that CTL lines that produce IFN-gamma in a peptide-specific manner were established after induction with each of the peptides. In the figure, "+" shows IFN-gamma production of the CTL line against target cells pulsed with a peptide of interest; and "−" shows IFN-gamma production of the CTL line against target cells that have not been pulsed with any peptide. The RS ratio indicates the ratio of the cell number of CTL line (Responder cells) and the cell number of target cells that stimulate them (Stimulator cells).
Figure 2:
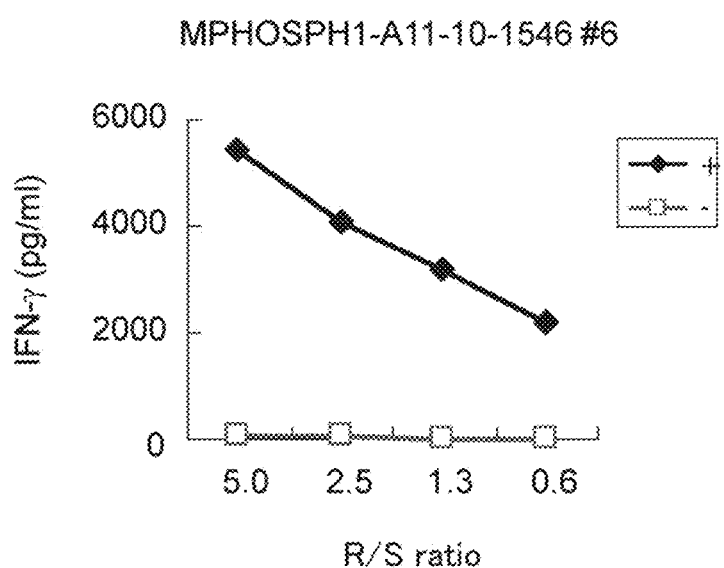
Figure 3:
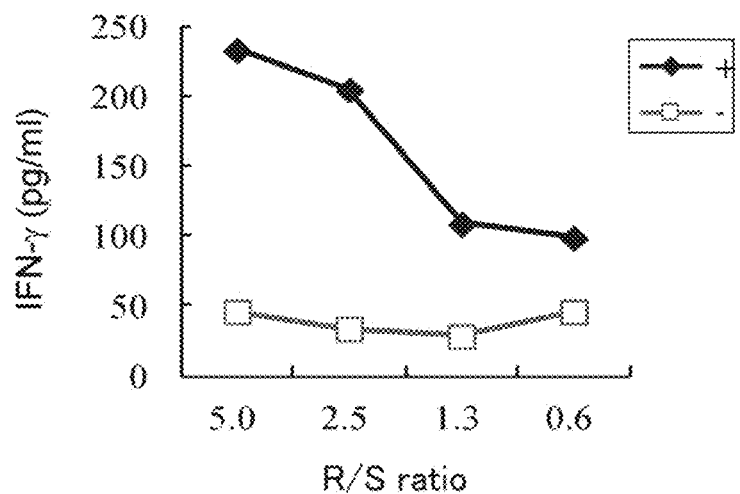
FIG. 3 consists of a series of line graphs (a) to (b) showing IFN-gamma production in a CTL clone established by the limiting dilution method following induction with MPHOSPH1-A11-9-1227 (SEQ ID NO: 12) (a) or MPHOSPH1-A11-10-1546 (SEQ ID NO: 52) (b). These results show the peptide-specific IFN-gamma production of the CTL clones. In the figure, "+" shows IFN-gamma production of the CTL clones against target cells pulsed with the peptide of interest; and "−" shows IFN-gamma production of the CTL clones against target cells that have not been pulsed with any peptide. The R/S ratio indicates the ratio of the cell number of CTL clone (Responder cells) and the cell number of target cells that stimulate them (Stimulator cells).
Figure 3:
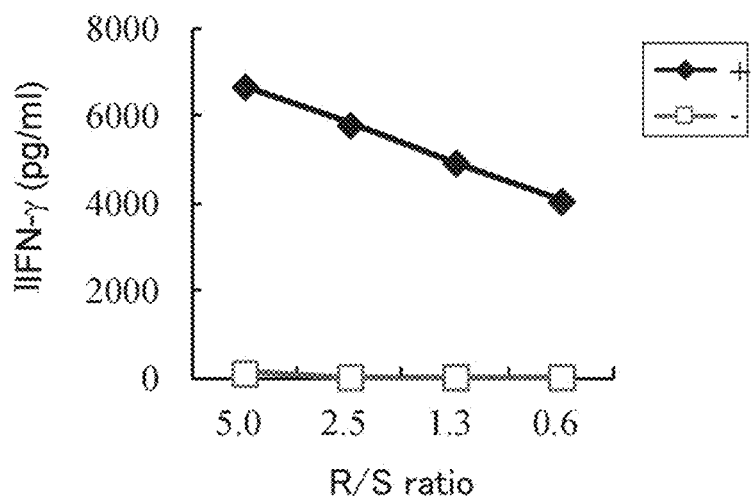

Establishment of CTL Lines and Clones Specific to HLA-A*11:01-Restricted MPHOSPH1-Derived Peptides CTL lines were established by propagating cells in Well #2 with MPHOSPH1-A11-9-1227 (SEQ ID NO: 12) (a) and Well #6 with MPHOSPH1-A11-10-1546 (SEQ ID NO: 52) (b) in the IFN-gamma ELISPOT assay. As a result of measuring IFN-gamma by ELISA, IFN-gamma production by the CTL lines against target cells (C1R-A11) pulsed with MPHOSPH1-A11-9-1227 (SEQ ID NO: 12) (a) or MPHOSPH1-A11-10-1546 (SEQ ID NO: 52) (b) was observed (FIG. 2). Further, CTL clones were established by the limiting dilution method as described in the "Materials and methods" section above. As a result of measuring IFN-gamma by ELISA, CTL clones stimulated with MPHOSPH1-A11-9-1227 (SEQ ID NO: 12) (a) or MPHOSPH1-A11-10-1546 (SEQ ID NO: 52) (b) each showed a peptide-specific IFN-gamma production (FIG. 3).

IFN-Gamma Production Against Target Cells Expressing MPHOSPH1 and HLA-A*11:01

Figure 4:
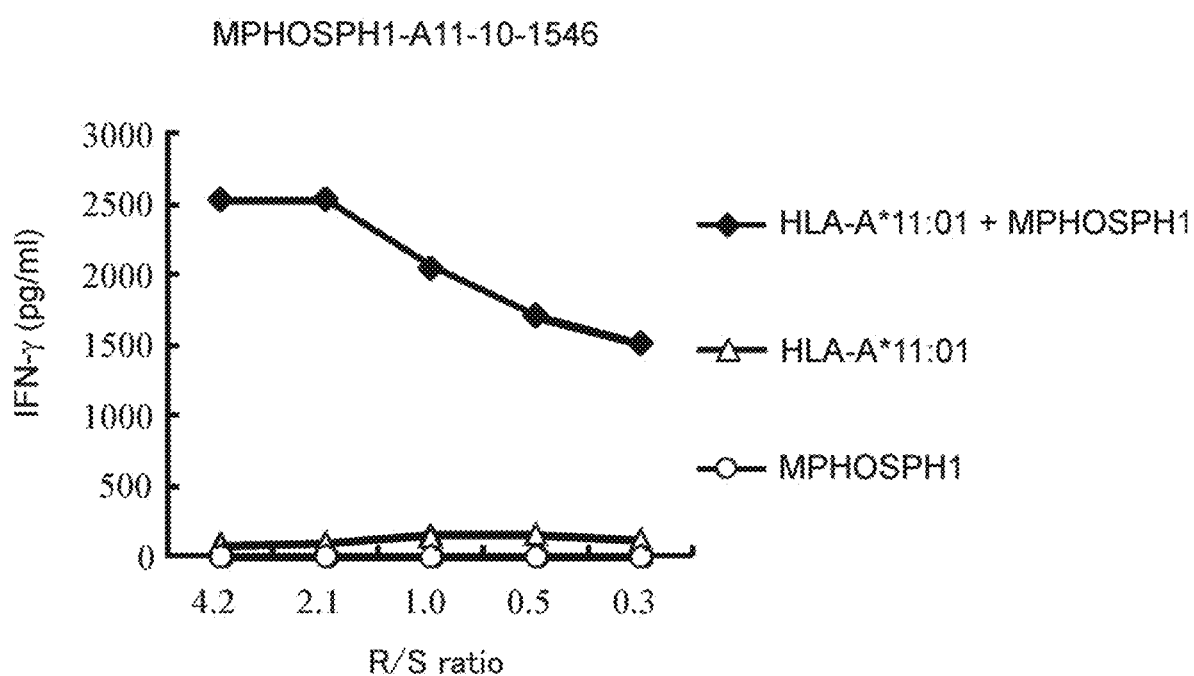
FIG. 4 is a line graph showing IFN-gamma production of CTL clones against target cells expressing both MPHOSPH1 and HLA-A*11:01. Target cells introduced with either HLA-A*11:01 or the full-length MPHOSPH1 gene were used as the negative control. The CTL clone established by induction using MPHOSPH1-A11-10-1546 (SEQ ID NO: 52) showed IFN-gamma production against COS7 cells introduced with both the MPHOSPH1 and HLA-A*11:01 genes (black diamond). On the other hand, a significant IFN-gamma production was not shown against COS7 cells introduced with either one of HLA-A*11:01 (triangle) and MPHOSPH1 (white circle).

IFN-gamma production of the MPHOSPH1-A11-10-1546 (SEQ ID NO: 52)-specific CTL clone against target cells expressing MPHOSPH1 and HLA-A*11:01 was investigated. COS7 cells expressing both MPHOSPH1 and HLA-A*11:01 were prepared as the target cell. COS7 cells expressing either one of MPHOSPH1 and HLA-A*11:01 were prepared as the negative control cell. The MPHOSPH1-A11-10-1546 (SEQ ID NO: 52)-specific CTL clone showed IFN-gamma production against COS7 cells expressing both MPHOSPH1 and HLA-A*11:01 (FIG. 4). On the other hand, a significant IFN-gamma production was not observed against the negative control cells. This clearly proves that MPHOSPH1-A11-10-1546 (SEQ ID NO: 52) is a peptide generated by antigen processing, and is presented on the cell surface with the HLA-A*11:01 molecule and recognized by CTLs. This result suggests that MPHOSPH1-A11-10-1546 (SEQ ID NO: 52) may be useful as a cancer vaccine for patients in whom MPHOSPH1 expression is enhanced in cancer cells.

Homology Analysis of Antigen Peptides

It has been confirmed that MPHOSPH1-A11-9-762 (SEQ ID NO: 5), MPHOSPH1-A11-9-1227 (SEQ ID NO: 12), MPHOSPH1-A11-9-96 (SEQ ID NO: 27), MPHOSPH1-A11-10-1546 (SEQ ID NO: 52), and MPHOSPH1-A11-10-1675 (SEQ ID NO: 53) may induce CTLs showing peptide-specific IFN-gamma production. Thus, to confirm that the MPHOSPH1-A11-9-762 (SEQ ID NO: 5), MPHOSPH1-A11-9-1227 (SEQ ID NO: 12), MPHOSPH1-A11-9-96 (SEQ ID NO: 27), MPHOSPH1-A11-10-1546 (SEQ ID NO: 52), and MPHOSPH1-A11-10-1675 (SEQ ID NO: 53) sequences are only derived from MPHOSPH1, homology analysis of the peptide sequences was performed using the BLAST algorithm (blast.ncbi.nlm.nih.gov/Blast.cgi). As a result, the MPHOSPH1-A11-9-762 (SEQ ID NO: 5), MPHOSPH1-A111-9-1227 (SEQ ID NO: 12), MPHOSPH1-A11-9-96 (SEQ ID NO: 27), MPHOSPH1-A11-10-1546 (SEQ ID NO: 52), and MPHOSPH1-A11-10-1675 (SEQ ID NO: 53) sequences were only found in MPHOSPH1. Therefore, to the knowledge of the present inventors, these peptides are specific to MPHOSPH1, so that there is almost no possibility that these peptides would elicit an unintended immune reaction against molecules other than MPHOSPH1 that are already known to sensitize the human immune system. In conclusion, novel MPHOSPH1-derived HLA-A11:01-restricted epitope peptides were identified. It was demonstrated that the MPHOSPH1-derived epitope peptides are applicable for cancer immunotherapy.

Example 2

Materials and Methods

Cell Lines

C1R cells, an HLA-A- and HLA-B-negative human B lymphoblastoid cell line, and COS7 cells, an African green monkey kidney cell line, were purchased from ATCC.

Generation of Target Cells with Steady HLA-A*33:03 Expression

C1R cells (C1R-A33) that steadily express HLA-A*33:03 were used as cells that stimulate CTLs. A cDNA encoding the HLA-A*33:03 gene was amplified by PCR and incorporated into an expression vector. C1R cells into which the HLA-A*33:03 gene expression vector was introduced were cultured under drug selection for two weeks in medium containing G418 (Invitrogen). The G418-resistant C1R cell suspension was diluted, seeded in a 96-well plate, and further selectively cultured for 30 days in a G418-containing medium. The HLA-A*33:03 expression in C1R cells was verified by flow cytometric analysis.

Selection of MPHOSPH1-Derived Peptides

MPHOSPH1-derived 9mer and 10mer peptides that are expected to bind to the HLA-A*33:03 molecule were determined using the binding prediction server "NetMHC pan2.4" (www.cbs.dtu.dk/services/NetMHCpan-2.4/) (Nielsen et al., PLoS One. 2007; 29; 2(8): e796; Hoof et al., Immunogenetics. 2009; 61(1): 1-13).

Peptide Synthesis

The peptides were synthesized by American Peptide Company (Sunnyvale, Calif.) according to a standard solid-phase synthesis method, and purified by reversed phase high-performance liquid chromatography (HPLC). The quality of the peptides (purity of 90% or higher) was guaranteed by HPLC and mass spectrometry. The peptides were dissolved in dimethylsulfoxide (final concentration: 20 mg/ml) and stored at −80 degrees C.

In Vitro CTL Induction

Monocyte-derived dendritic cells (DCs) were used as the antigen-presenting cell to induce a specific cytotoxic T lymphocyte (CTL) response against peptides presented on human leukocyte antigens (HLAs). As already reported in literatures, DCs were generated in vitro (Nakahara S et al., Cancer Res 2003, 63(14): 4112-8). Specifically, peripheral-blood mononuclear cells (PBMCs) collected from healthy volunteers (HLA-A*33:03-positive) with the Ficoll-Paque plus solution (Pharmacia) were seeded in plastic tissue culture dishes (Corning) to let the monocytes in the PBMCs adhere to the dishes. This was cultured in the presence of 1000 IU/ml granulocyte macrophage colony-stimulating factor (R&D System) and 1000 IU/ml interleukin (IL)-4 (R&D System) for seven days. An AIM-V medium (Invitrogen) containing 5% inactivated AB-type serum (ABS) was used as the medium. DCs that were induced to differentiate from monocytes using the cytokines were pulsed with 20 micro-g/ml of each synthesized peptide (37 degrees C., three hours). Peptide pulsing was carried out in an AIM-V medium containing 3 micro-g/ml beta 2-microglobulin. These peptide-pulsed DCs were inactivated by X-ray irradiation (20 Gy), mixed in a 1:20 ratio with autologous CD8 positive T cells obtained by positive selection using the CD8 Positive Isolation Kit (Invitrogen) (1.5×10$^4$ DCs and 3×10$^5$ CD8 positive T cells), and cultured in a 48-well plate (Corning). Each well contained 0.5 ml of the 5% ABS/AIM-V medium, and IL-7 (R&D System) was added there (final concentration: 10 ng/ml). Two days after the start of the culture, IL-2 (Novartis) was added (final concentration: 20 IU/ml). On day 7 and day 14 of culture, the CD8 positive T cells were further stimulated with peptide-pulsed DCs. The DCs were prepared at the time of use by the same method as above. After day 21 (after three DC stimulations), IFN-gamma production against the peptide-pulsed C1R-A33 was confirmed using human interferon (IFN)-gamma enzyme-linked immunospot (ELISPOT) assay (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

CTL Propagation Procedure

CTLs were propagated using methods similar to those reported by Riddell et al. (Walter E A et al., N Engl J Med 1995, 333(16): 1038-44; Riddell S R et al., Nat Med 1996, 2(2): 216-23). The CTLs were cultured in 25 ml 5% ABS/AIM-V medium together with two types of Mitomycin C-treated human B lymphoblastoid cell lines (5×10$^6$ cells/25 ml medium each) and an anti-CD3 antibody (final concentration: 40 ng/ml). On the day after beginning of the culturing, IL-2 (final concentration: 120 IU/ml) was added to the culture. On days 5, 8 and 11, the medium was changed to a 5% ABS/AIM-V medium containing IL-2 (final concentration: 30 IU/ml) (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

Establishment of CTL Clones

After induction of CTLs in vitro, the CTLs were seeded onto 96 round-bottomed microtiter plates (Nalge Nunc International) at 1 cell/well or 10 cells/well. The CTLs were cultured with two types of Mitomycin C-treated human B lymphoblastoid cell lines (1×10$^4$ cells/well each) in a total of 150 micro-l/well 5% ABS/AIM-V medium with an anti-CD3 antibody (final concentration: 30 ng/ml) and IL-2 (final concentration: 125 IU/ml). Ten days later, 50 micro-l 5% ABS/AIM-V medium containing 500 IU/ml IL-2 was added to the culture. On day 14 or after, CTLs that showed peptide-specific IFN-gamma production in an ELISPOT assay were propagated using the same method as described above (Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

Confirmation of IFN-Gamma Production

To confirm the peptide-specific IFN-gamma production of CTLs induced with a peptide, an IFN-gamma ELISPOT assay and an IFN-gamma ELISA were performed. Peptide-pulsed C1R-A33 (1×10$^4$ cells/well) was prepared as the target cell. The IFN-gamma ELISPOT assay and IFN-gamma ELISA assay were performed according to the assay kit manufacturer's manual.

Preparation of Target Cells Forcibly Expressing MPHOSPH1 and HLA-A*33:03

A cDNA encoding the MPHOSPH1 or HLA-A*33:03 gene was amplified by PCR. The PCR-amplified product was each incorporated into an expression vector. Either or both of the MPHOSPH1 gene-expressing vector and the HLA-A*33:03 gene-expressing vector were introduced into COS7, which is a cell line negative for HLA, using Lipofectamine 2000 (Invitrogen). On the day after gene introduction, COS7 cells were detached and harvested using versene (Invitrogen), and used as the target cell for confirmation of IFN-gamma production (5×10$^4$ cells/well).

Results

Prediction of MPHOSPH1-Derived HLA-A*33:03-Binding Peptides

Tables 2a and 2b show MPHOSPH1-derived 9mer peptides and 10mer peptides that have been predicted to bind to HLA-A*33:03 by "NetMHC pan2.4" in the descending order of binding affinity. A total of 78 peptides that potentially have an HLA-A*33:03-binding ability was used as epitope peptide candidates.

TABLE 2a

HLA-A*33:03-binding 9mer peptides derived from MPHOSPH1

| Start position | Amino acid sequence | Kd (nM) | SEQ ID NO |
|---|---|---|---|
| 608 | EFTQYWAQR | 17.06 | 118 |
| 1474 | DLQKWREER | 25.07 | 119 |
| 1523 | QIMDIKPKR | 35.56 | 120 |
| 1663 | SSKKTYSLR | 41.91 | 48 |
| 509 | NSKILNVKR | 71.91 | 121 |
| 1767 | HQIIKRRLR | 82.02 | 122 |
| 629 | EILEENAER | 85.51 | 123 |
| 1606 | VTVKIPKAR | 101.85 | 124 |
| 293 | KFQKRKMLR | 108.81 | 125 |
| 1151 | ESIILKLER | 113.20 | 126 |
| 424 | KFQQHVPFR | 119.23 | 127 |
| 4 | NFNQEGVPR | 119.92 | 128 |
| 305 | DVKGYSFIK | 145.68 | 129 |
| 1112 | LTQGVTCYK | 163.64 | 2 |
| 1198 | DMKHLLQLK | 165.44 | 130 |
| 962 | SNIDLLNLR | 190.24 | 131 |
| 16 | VFSADPIAR | 191.67 | 132 |
| 109 | MAQKFSFSK | 194.66 | 1 |
| 739 | TINEFQNLK | 206.27 | 4 |
| 1443 | EMKKYAEDR | 208.73 | 133 |
| 439 | YFQSFFNGK | 228.11 | 50 |
| 1730 | VSQPKRAKR | 229.27 | 134 |
| 1001 | EYRIQEPNR | 239.25 | 135 |
| 995 | VSKQVKEYR | 251.90 | 136 |
| 178 | VLFDSLQER | 270.86 | 137 |
| 830 | NIAEIEDIR | 320.33 | 138 |
| 1545 | LSTSFEISR | 331.38 | 139 |

TABLE 2a-continued

HLA-A*33:03-binding 9mer peptides derived from MPHOSPH1

| Start position | Amino acid sequence | Kd (nM) | SEQ ID NO |
|---|---|---|---|
| 191 | MNLKPHRSR | 337.04 | 140 |
| 1262 | VQKEVSVMR | 434.39 | 141 |
| 285 | DLFVPVSSK | 456.68 | 142 |
| 1356 | EAKLEEVER | 509.15 | 143 |
| 282 | YIYDLFVPV | 545.45 | 144 |
| 1378 | DLETKNNQR | 597.27 | 145 |
| 566 | AFISHEEKR | 647.83 | 146 |
| 274 | SFFEIYNEY | 699.38 | 147 |
| 289 | PVSSKFQKR | 723.20 | 148 |
| 1633 | NATPRTNLK | 726.27 | 149 |
| 644 | DLVGKCDTR | 831.89 | 150 |
| 1629 | ENKKNATPR | 874.58 | 151 |
| 182 | SLQERLYTK | 888.77 | 14 |
| 364 | DSEMSRVIR | 927.06 | 152 |

Start position indicates the number of amino acid residue from the N terminus of MPHOSPH1.
The dissociation constant [Kd (nM)] is derived from "NetMHCpan 2.4".

TABLE 2b

HLA-A*33:03-binding 10mer peptides derived from MPHOSPH1

| Start position | Amino acid sequence | Kd (nM) | SEQ ID NO |
|---|---|---|---|
| 15 | YVFSADPIAR | 28.76 | 98 |
| 619 | DFKETLLQER | 29.78 | 153 |
| 341 | FTKLNNASSR | 35.36 | 154 |
| 782 | DSKSKICSER | 39.22 | 155 |
| 188 | YTKMNLKPHR | 47.68 | 156 |
| 212 | EIASKSALLR | 58.27 | 157 |
| 438 | HYFQSFFNGK | 75.94 | 158 |
| 319 | QVSDSKEAYR | 87.99 | 159 |
| 1729 | NVSQPKRAKR | 88.94 | 160 |
| 944 | LMHTKIDELR | 102.01 | 161 |
| 1607 | TVKIPKARKR | 121.80 | 162 |
| 177 | NVLFDSLQER | 123.79 | 107 |
| 738 | DTINEFQNLK | 137.06 | 77 |
| 994 | LVSKQVKEYR | 144.15 | 163 |
| 387 | TMKTQNEGER | 154.63 | 164 |
| 761 | DTSSLIINNK | 169.23 | 67 |
| 924 | LSNEIETATR | 191.09 | 165 |
| 1639 | NLKFPISDDR | 216.60 | 166 |
| 149 | FTYGLTNSGK | 268.53 | 57 |
| 377 | SLCDLAGSER | 319.11 | 104 |
| 629 | EILEENAERR | 327.56 | 167 |
| 190 | KMNLKPHRSR | 335.96 | 168 |
| 1261 | QVQKEVSVMR | 360.40 | 169 |
| 57 | DYLQVCLRIR | 517.46 | 170 |
| 1098 | QIQHVVEGKR | 527.36 | 171 |
| 582 | DLKKKLINEK | 542.54 | 172 |
| 108 | QMAQKFSFSK | 543.93 | 60 |
| 961 | ISNIDLLNLR | 584.25 | 173 |
| 508 | SNSKILNVKR | 611.66 | 174 |
| 181 | DSLQERLYTK | 633.51 | 68 |
| 3 | SNFNQEGVPR | 636.03 | 175 |
| 194 | KPHRSREYLR | 678.04 | 176 |
| 1268 | VMRDEDKLLR | 736.18 | 177 |
| 1522 | TQIMDIKPKR | 810.10 | 178 |
| 322 | DSKEAYRLLK | 833.84 | 111 |
| 607 | QEFTQYWAQR | 939.95 | 179 |
| 565 | KAFISHEEKR | 943.45 | 180 |

Start position indicates the number of amino acid residue from the N terminus of MPHOSPH1.
The dissociation constant [Kd (nM)] is derived from "NetMHCpan 2.4".

Figure 5:
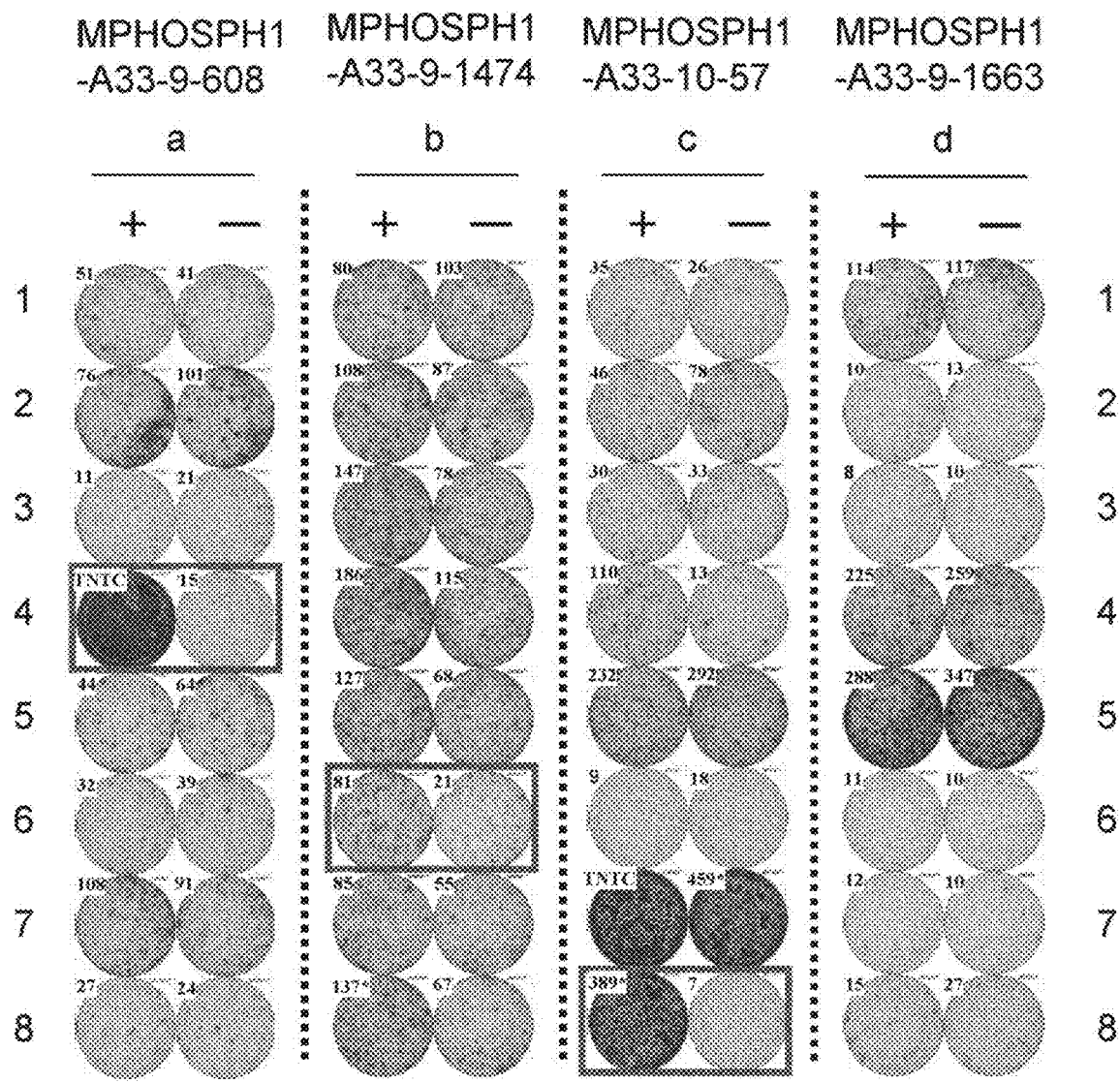
FIG. 5 consists of photos (a) to (d) showing results of an IFN-gamma ELISPOT assay performed using cells induced with peptides derived from MPHOSPH1. In the figure. "+" shows IFN-gamma production against target cells pulsed with the peptide of interest; and "−" shows IFN-gamma production against target cells that have not been pulsed with any peptide (negative controls).

Induction of CTLs by the Predicted MPHOSPH1-Derived HLA-A*33:03-Restricted Peptides MPHOSPH1-derived peptide-specific CTLs were induced according to the protocol described in "Materials and methods". The peptide-specific IFN-gamma production was confirmed by an ELISPOT assay (FIG. 5). Peptide-specific IFN-gamma production was observed in Well #4 with MPHOSPH1-A33-9-608 (SEQ ID NO: 118) (a), Well #6 with MPHOSPH1-A33-9-1474 (SEQ ID NO: 119) (b), and Well #8 with MPHOSPH1-A33-10-57 (SEQ ID NO: 170) (c). Meanwhile, specific IFN-gamma production against other peptides shown in Tables 2a and 2b was not observed. For example, specific IFN-gamma production was not observed against MPHOSPH1-A33-9-1663 (SEQ ID NO: 48) (d). As a result, although all the peptides had the potential of binding to HLA-A*33:03, three peptides were selected as peptides having CTL-inducing ability.

Establishment of CTL Lines and Clones Specific to HLA-A*33:03-Restricted MPHOSPH1-Derived Peptides CTL lines were established by propagating cells in Well #4 with MPHOSPH1-A33-9-608 (SEQ ID NO: 118) (a) and Well #8 with MPHOSPH1-A33-10-57 (SEQ ID NO: 170) (b) in the IFN-gamma ELISPOT assay. As a result of measuring IFN-gamma by ELISA, IFN-gamma production by the CTL lines against target cells (C1R-A33) pulsed with MPHOSPH1-A33-9-608 (SEQ ID NO: 118) (a) or MPHOSPH1-A33-10-57 (SEQ ID NO: 170) (b) was observed (FIG. 6). Further, CTL clones were established by the limiting dilution method as described in the "Materials and methods" section above. As a result of measuring IFN-gamma by ELISA, CTL clones stimulated with MPHOSPH1-A33-9-608 (SEQ ID NO: 118) (a) or MPHOSPH1-A33-10-57 (SEQ ID NO: 170) (b) each showed a peptide-specific IFN-gamma production (FIG. 7).

IFN-Gamma Production Against Target Cells Expressing MPHOSPH1 and HLA-A*33:03

IFN-gamma production of the MPHOSPH1-A33-9-608 (SEQ ID NO: 118)-specific CTL clone against target cells expressing MPHOSPH1 and HLA-A*33:03 was investigated. COS7 cells expressing both MPHOSPH1 and HLA-A*33:03 were prepared as the target cell. COS7 cells expressing either one of MPHOSPH1 and HLA-A*33:03 were prepared as the negative control cell. The MPHOSPH1-A33-9-608 (SEQ ID NO: 118)-specific CTL clone showed IFN-gamma production against COS7 cells expressing both MPHOSPH1 and HLA-A*33:03 (FIG. 8). On the other hand, a significant IFN-gamma production was not observed against the negative control cells. This clearly proves that MPHOSPH1-A33-9-608 (SEQ ID NO: 118) is a peptide generated by antigen processing, and is presented on the cell surface with the HLA-A*33:03 molecule and recognized by CTLs. This result suggests that MPHOSPH1-A33-9-608 (SEQ ID NO: 118) may be useful as a cancer vaccine for patients in whom MPHOSPH1 expression is enhanced in cancer cells.

Homology Analysis of Antigen Peptides

It has been confirmed that MPHOSPH1-A33-9-608 (SEQ ID NO: 118), MPHOSPH1-A33-9-1474 (SEQ ID NO: 119), and MPHOSPH1-A33-10-57 (SEQ ID NO: 170) may induce CTLs showing peptide-specific IFN-gamma production. Thus, to confirm that the MPHOSPH1-A33-9-608 (SEQ ID NO: 118), MPHOSPH1-A33-9-1474 (SEQ ID NO: 119), and MPHOSPH1-A33-10-57 (SEQ ID NO: 170) sequences are only derived from MPHOSPH1, homology analysis of the peptide sequences was performed using the BLAST algorithm (blast.ncbi.nlm.nih.gov/Blast.cgi). As a result, the MPHOSPH1-A33-9-608 (SEQ ID NO: 118), MPHOSPH1-A33-9-1474 (SEQ ID NO: 119), and MPHOSPH1-A33-10-57 (SEQ ID NO: 170) sequences were only found in MPHOSPH1. Therefore, to the knowledge of the present inventors, these peptides are specific to MPHOSPH1, so that there is almost no possibility that these peptides would elicit an unintended immune response against molecules other than MPHOSPH1 that are already known to sensitize the human immune system. In conclusion, novel MPHOSPH1-derived HLA-A33:03-restricted epitope peptides were identified. It was demonstrated that the MPHOSPH1-derived epitope peptides are applicable for cancer immunotherapy.

Example 3

Preparation of Emulsion Formulations

A peptide was dissolved in an injection solvent or sterile physiological saline to become 1.0 mg/ml to 10.0 mg/ml, and collected into a syringe. This was connected via a connector to a syringe filled with an IFA in an amount equivalent to an injection solvent or sterile physiological saline, and mixed by alternately pushing the syringe plungers of the two connected syringes. After several minutes of mixing, completion of the emulsion was assessed by the drop test method. The drop test method can be performed by dropping one drop of the mixed sample on water. The emulsion is assessed as completed when the sample dropped on water does not immediately diffuse in water; and the emulsion is assessed as incompleted when the sample dropped on water diffuses right away in water. When the emulsion is assessed as incompleted, further mixing is carried out to complete the emulsion. The completed emulsion can be administered to a cancer patient by subcutaneous injection. The cancer patient subject to administration can be selected from patients affected by bladder cancer, breast cancer, cervical cancer, cholangiocellular cancer, chronic myeloid leukemia (CML), colon cancer, gastric cancer, lung cancer, lymphoma, osteosarcoma, prostate cancer, kidney cancer, soft tissue tumor or such.

Preparation of Freeze-Dried Formulations

A peptide was dissolved in an injection solvent to become 1.0 mg/ml to 10.0 mg/ml, and sterilized by filtration. This was filled into a sterilized vial, and half-capped with a sterilized rubber plug. After this vial was freeze-dried, it was completely capped and seamed with an aluminum cap to produce a freeze-dried formulation. When in use, an injection solvent or sterile physiological saline was injected into the vial to re-dissolve the freeze-dried powder. The re-dissolved solution in the vial was collected using a syringe, and the syringe was connected via a connector with a syringe filled with an IFA in an amount equivalent to the collected re-dissolved solution. The re-dissolved solution and IFA were mixed by alternately pushing the syringe plungers of the two connected syringes. After several minutes of mixing, completion of the emulsion was assessed by the drop test method. The completed emulsion can be administered to a cancer patient by subcutaneous injection. The cancer patient subject to administration can be selected from patients affected by bladder cancer, breast cancer, cervical cancer, cholangiocellular cancer, chronic myeloid leukemia (CML), colon cancer, gastric cancer, lung cancer, lymphoma, osteosarcoma, prostate cancer, kidney cancer, soft tissue tumor or such.

INDUSTRIAL APPLICABILITY

The present invention provides MPHOSPH1-derived novel HLA-A11-restricted and HLA-A33-restricted epitope peptides that induce a potent and specific anti-tumor immune response and thus have applicability for a wide range of cancer types. The peptides, compositions, APCs, and CTLs in the present invention can be used as a peptide vaccine for cancer expressing MPHOSPH1, for example, bladder cancer, breast cancer, cervical cancer, cholangiocellular cancer, chronic myeloid leukemia (CML), colon cancer, gastric cancer, lung cancer, lymphoma, osteosarcoma, prostate cancer, kidney cancer, and soft tissue tumor.

While the present invention is herein described in detail and with respect to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

The invention claimed is:

1. An isolated peptide having cytotoxic T cell (CTL)-inducing ability and selected from the group consisting of:
   (i) a peptide consisting of an amino acid sequence selected from the group consisting of SEQ ID NOs: 5, 12, 27, 52, and 53 into which one or two substitution(s) selected from the group consisting of (a) to (d) below is introduced:
      (a) the second amino acid from the N terminus is substituted with an amino acid selected from the group consisting of threonine, valine, isoleucine, leucine, phenylalanine and tyrosine;
      (b) the third amino acid from the N terminus is substituted with an amino acid selected from the group consisting of leucine, phenylalanine, tyrosine, isoleucine and alanine;
      (c) the seventh amino acid from the N terminus is substituted with an amino acid selected from the group consisting of leucine, isoleucine, tyrosine, valine and phenylalanine; and
      (d) the C-terminal amino acid is substituted with an amino acid selected from the group consisting of lysine and arginine; and
   (ii) a peptide consisting of an amino acid sequence selected from the group consisting of SEQ ID NOs: 118, 119, and 170 into which one or two substitution(s) selected from the group consisting of (a) to (c) below is introduced:
      (a) the first amino acid from the N terminus is substituted with an amino acid selected from the group consisting of aspartic acid and glutamic acid;
      (b) the second amino acid from the N terminus is substituted with an amino acid selected from the group consisting of phenylalanine, tyrosine, alanine, isoleucine, leucine, and valine; and
      (c) the C-terminal amino acid is substituted with an amino acid selected from the group consisting of arginine and lysine.

2. An isolated polynucleotide, which encodes the peptide of claim 1.

3. A composition comprising a pharmaceutically acceptable carrier and at least one ingredient selected from the group consisting of (A) to (B) below:
   (A) one or more types of peptides having cytotoxic T cell (CTL)-inducing ability and selected from the group below:
      (i) a peptide consisting of an amino acid sequence selected from the group consisting of SEQ ID NOs: 5, 12, 27, 52, 53, 118, 119, and 170; and
      (ii) a peptide consisting of an amino acid sequence selected from the group consisting of (1) to (2) below:
         (1) a peptide consisting of an amino acid sequence selected from the group consisting of SEQ ID NOs: 5, 12, 27, 52, and 53 into which one or two substitution(s) selected from the group consisting of (a) to (d) below is introduced:
            (a) the second amino acid from the N terminus is substituted with an amino acid selected from the group consisting of threonine, valine, isoleucine, leucine, phenylalanine and tyrosine;
            (b) the third amino acid from the N terminus is substituted with an amino acid selected from the group consisting of leucine, phenylalanine, tyrosine, isoleucine and alanine;
            (c) the seventh amino acid from the N terminus is substituted with an amino acid selected from the group consisting of leucine, isoleucine, tyrosine, valine and phenylalanine; and
            (d) the C-terminal amino acid is substituted with an amino acid selected from the group consisting of lysine and arginine; and
         (2) a peptide consisting of an amino acid sequence selected from the group consisting of SEQ ID NOs: 118, 119, and 170 into which one or two substitution(s) selected from the group consisting of (a) to (c) below is introduced:
  (a) the first amino acid from the N terminus is substituted with an amino acid selected from the group consisting of aspartic acid and glutamic acid;
  (b) the second amino acid from the N terminus is substituted with an amino acid selected from the group consisting of phenylalanine, tyrosine, alanine, isoleucine, leucine, and valine; and
  (c) the C-terminal amino acid is substituted with an amino acid selected from the group consisting of arginine and lysine; and
(B) one or more types of polynucleotides encoding the peptide(s) of (A) in an expressible form;
in combination with an adjuvant in an amount to enhance an immune response.

4. The composition of claim 3, which is a pharmaceutical composition.

5. The composition of claim 4, for the treatment bladder cancer.

6. The composition of claim 4, which is for inducing an immune response against bladder cancer.

7. The composition of claim 3, which is formulated for administration to a subject positive for at least one HLA selected from the group consisting of HLA-A11 and HLA-A33.

8. A composition for inducing a CTL(s) comprising at least one ingredient selected from the group consisting of (A) to (B) below:
(A) one or more types of peptides having cytotoxic T cell (CTL)-inducing ability and selected from the group below:
  (i) a peptide consisting of an amino acid sequence selected from the group consisting of SEQ ID NOs: 5, 12, 27, 52, 53, 118, 119, and 170; and
  (ii) a peptide consisting of an amino acid sequence selected from the group consisting of (1) to (2) below:
    (1) a peptide consisting of an amino acid sequence selected from the group consisting of SEQ ID NOs: 5, 12, 27, 52, and 53 into which one or two substitution(s) selected from the group consisting of (a) to (d) below is introduced:
      (a) the second amino acid from the N terminus is substituted with an amino acid selected from the group consisting of threonine, valine, isoleucine, leucine, phenylalanine and tyrosine;
      (b) the third amino acid from the N terminus is substituted with an amino acid selected from the group consisting of leucine, phenylalanine, tyrosine, isoleucine and alanine;
      (c) the seventh amino acid from the N terminus is substituted with an amino acid selected from the group consisting of leucine, isoleucine, tyrosine, valine and phenylalanine; and
      (d) the C-terminal amino acid is substituted with an amino acid selected from the group consisting of lysine and arginine; and
    (2) a peptide consisting of an amino acid sequence selected from the group consisting of SEQ ID NOs: 118, 119, and 170 into which one or two substitution(s) selected from the group consisting of (a) to (c) below is introduced:
      (a) the first amino acid from the N terminus is substituted with an amino acid selected from the group consisting of aspartic acid and glutamic acid;
      (b) the second amino acid from the N terminus is substituted with an amino acid selected from the group consisting of phenylalanine, tyrosine, alanine, isoleucine, leucine, and valine; and
      (c) the C-terminal amino acid is substituted with an amino acid selected from the group consisting of arginine and lysine; and
(B) one or more types of polynucleotides encoding the peptide(s) of (A) in an expressible form;
in combination with an adjuvant in an amount to enhance an immune response.

9. A method of inducing an APC(s) to present on its surface a peptide having CTL-inducing ability, the method comprising contacting an APC(s) with the peptide, wherein the peptide comprises an amino acid sequence selected from the group below:
  (i) a peptide consisting of an amino acid sequence selected from the group consisting of SEQ ID NOs: 5, 12, 27, 52, 53, 118, 119, and 170; and
  (ii) a peptide consisting of an amino acid sequence selected from the group consisting of (1) to (2) below:
    (1) a peptide consisting of an amino acid sequence selected from the group consisting of SEQ ID NOs: 5, 12, 27, 52, and 53 into which one or two substitution(s) selected from the group consisting of (a) to (d) below is introduced:
      (a) the second amino acid from the N terminus is substituted with an amino acid selected from the group consisting of threonine, valine, isoleucine, leucine, phenylalanine and tyrosine;
      (b) the third amino acid from the N terminus is substituted with an amino acid selected from the group consisting of leucine, phenylalanine, tyrosine, isoleucine and alanine;
      (c) the seventh amino acid from the N terminus is substituted with an amino acid selected from the group consisting of leucine, isoleucine, tyrosine, valine and phenylalanine; and
      (d) the C-terminal amino acid is substituted with an amino acid selected from the group consisting of lysine and arginine; and
    (2) a peptide consisting of an amino acid sequence selected from the group consisting of SEQ ID NOs: 118, 119, and 170 into which one or two substitution(s) selected from the group consisting of (a) to (c) below is introduced:
      (a) the first amino acid from the N terminus is substituted with an amino acid selected from the group consisting of aspartic acid and glutamic acid;
      (b) the second amino acid from the N terminus is substituted with an amino acid selected from the group consisting of phenylalanine, tyrosine, alanine, isoleucine, leucine, and valine; and
      (c) the C-terminal amino acid is substituted with an amino acid selected from the group consisting of arginine and lysine;

wherein, the contacting is in vitro, ex vivo, or in vivo; thereby inducing the APC(s) to present on its surface the CTL-inducing peptide.

10. A method of inducing a CTL(s), the method comprising co-culturing a CD8-positive T cell(s) with an APC(s) that presents on its surface a complex of an HLA antigen and a peptide having cytotoxic T cell (CTL)-inducing ability, wherein the peptide is selected from the group below:
   (i) a peptide consisting of an amino acid sequence selected from the group consisting of SEQ ID NOs: 5, 12, 27, 52, 53, 118, 119, and 170; and
   (ii) a peptide consisting of an amino acid sequence selected from the group consisting of (1) to (2) below:
      (1) a peptide consisting of an amino acid sequence selected from the group consisting of SEQ ID NOs: 5, 12, 27, 52, and 53 into which one or two substitution(s) selected from the group consisting of (a) to (d) below is introduced:
         (a) the second amino acid from the N terminus is substituted with an amino acid selected from the group consisting of threonine, valine, isoleucine, leucine, phenylalanine and tyrosine;
         (b) the third amino acid from the N terminus is substituted with an amino acid selected from the group consisting of leucine, phenylalanine, tyrosine, isoleucine and alanine;
         (c) the seventh amino acid from the N terminus is substituted with an amino acid selected from the group consisting of leucine, isoleucine, tyrosine, valine and phenylalanine; and
         (d) the C-terminal amino acid is substituted with an amino acid selected from the group consisting of lysine and arginine; and
      (2) a peptide consisting of an amino acid sequence selected from the group consisting of SEQ ID NOs: 118, 119, and 170 into which one or two substitution(s) selected from the group consisting of (a) to (c) below is introduced:
         (a) the first amino acid from the N terminus is substituted with an amino acid selected from the group consisting of aspartic acid and glutamic acid;
         (b) the second amino acid from the N terminus is substituted with an amino acid selected from the group consisting of phenylalanine, tyrosine, alanine, isoleucine, leucine, and valine; and
         (c) the C-terminal amino acid is substituted with an amino acid selected from the group consisting of arginine and lysine.

11. A method of inducing an immune response against bladder cancer, the method comprising administering to a subject one or more types of peptides having cytotoxic T cell (CTL)-inducing ability, wherein each of the one or more types of peptides is selected from the group below:
   (i) a peptide consisting of an amino acid sequence selected from the group consisting of SEQ ID NOs: 5, 12, 27, 52, 53, 118, 119, and 170; and
   (ii) a peptide consisting of an amino acid sequence selected from the group consisting of (1) to (2) below:
      (1) a peptide consisting of an amino acid sequence selected from the group consisting of SEQ ID NOs: 5, 12, 27, 52, and 53 into which one or two substitution(s) selected from the group consisting of (a) to (d) below is introduced:
         (a) the second amino acid from the N terminus is substituted with an amino acid selected from the group consisting of threonine, valine, isoleucine, leucine, phenylalanine and tyrosine;
         (b) the third amino acid from the N terminus is substituted with an amino acid selected from the group consisting of leucine, phenylalanine, tyrosine, isoleucine and alanine;
         (c) the seventh amino acid from the N terminus is substituted with an amino acid selected from the group consisting of leucine, isoleucine, tyrosine, valine and phenylalanine; and
         (d) the C-terminal amino acid is substituted with an amino acid selected from the group consisting of lysine and arginine; and
      (2) a peptide consisting of an amino acid sequence selected from the group consisting of SEQ ID NOs: 118, 119, and 170 into which one or two substitution(s) selected from the group consisting of (a) to (c) below is introduced:
         (a) the first amino acid from the N terminus is substituted with an amino acid selected from the group consisting of aspartic acid and glutamic acid;
         (b) the second amino acid from the N terminus is substituted with an amino acid selected from the group consisting of phenylalanine, tyrosine, alanine, isoleucine, leucine, and valine; and
         (c) the C-terminal amino acid is substituted with an amino acid selected from the group consisting of arginine and lysine.

12. A method of treating bladder cancer, the method comprising administering to a subject one or more types of peptides having cytotoxic T cell (CTL)-inducing ability and selected from the group below:
   (i) a peptide consisting of an amino acid sequence selected from the group consisting of SEQ ID NOs: 5, 12, 27, 52, 53, 118, 119, and 170; and
   (ii) a peptide consisting of an amino acid sequence selected from the group consisting of (1) to (2) below:
      (1) a peptide consisting of an amino acid sequence selected from the group consisting of SEQ ID NOs: 5, 12, 27, 52, and 53 into which one or two substitution(s) selected from the group consisting of (a) to (d) below is introduced:
         (a) the second amino acid from the N terminus is substituted with an amino acid selected from the group consisting of threonine, valine, isoleucine, leucine, phenylalanine and tyrosine;
         (b) the third amino acid from the N terminus is substituted with an amino acid selected from the group consisting of leucine, phenylalanine, tyrosine, isoleucine and alanine;
         (c) the seventh amino acid from the N terminus is substituted with an amino acid selected from the group consisting of leucine, isoleucine, tyrosine, valine and phenylalanine; and
         (d) the C-terminal amino acid is substituted with an amino acid selected from the group consisting of lysine and arginine; and
      (2) a peptide consisting of an amino acid sequence selected from the group consisting of SEQ ID NOs: 118, 119, and 170 into which one or two substitution(s) selected from the group consisting of (a) to (c) below is introduced:
         (a) the first amino acid from the N terminus is substituted with an amino acid selected from the group consisting of aspartic acid and glutamic acid;

(b) the second amino acid from the N terminus is substituted with an amino acid selected from the group consisting of phenylalanine, tyrosine, alanine, isoleucine, leucine, and valine; and (c) the C-terminal amino acid is substituted with an amino acid selected from the group consisting of arginine and lysine.

13. An emulsion comprising one or more types of peptides having cytotoxic T cell (CTL)-inducing ability and selected from the group below:

(i) a peptide consisting of an amino acid sequence selected from the group consisting of SEQ ID NOs: 5, 12, 27, 52, 53, 118, 119, and 170; and (ii) a peptide consisting of an amino acid sequence selected from the group consisting of (1) to (2) below:

(1) a peptide consisting of an amino acid sequence selected from the group consisting of SEQ ID NOs: 5, 12, 27, 52, and 53 into which one or two substitution(s) selected from the group consisting of (a) to (d) below is introduced:

(a) the second amino acid from the N terminus is substituted with an amino acid selected from the group consisting of threonine, valine, isoleucine, leucine, phenylalanine and tyrosine;

(b) the third amino acid from the N terminus is substituted with an amino acid selected from the group consisting of leucine, phenylalanine, tyrosine, isoleucine and alanine;

(c) the seventh amino acid from the N terminus is substituted with an amino acid selected from the group consisting of leucine, isoleucine, tyrosine, valine and phenylalanine; and (d) the C-terminal amino acid is substituted with an amino acid selected from the group consisting of lysine and arginine; and (2) a peptide consisting of an amino acid sequence selected from the group consisting of SEQ ID NOs: 118, 119, and 170 into which one or two substitution(s) selected from the group consisting of (a) to (c) below is introduced:

(a) the first amino acid from the N terminus is substituted with an amino acid selected from the group consisting of aspartic acid and glutamic acid;

(b) the second amino acid from the N terminus is substituted with an amino acid selected from the group consisting of phenylalanine, tyrosine, alanine, isoleucine, leucine, and valine; and (c) the C-terminal amino acid is substituted with an amino acid selected from the group consisting of arginine and lysine;

a water-soluble carrier; and an oil adjuvant in an amount to enhance an immune response.

14. A kit comprising a container that houses a composition comprising:

a pharmaceutically acceptable carrier; and at least one ingredient selected from the group consisting of (A) to (B) below:

(A) one or more types of peptides having cytotoxic T cell (CTL)-inducing ability and selected from the group below:

(i) a peptide consisting of an amino acid sequence selected from the group consisting of SEQ ID NOs: 5, 12, 27, 52, 53, 118, 119, and 170; and (ii) a peptide consisting of an amino acid sequence selected from the group consisting of (1) to (2) below:

(1) a peptide consisting of an amino acid sequence selected from the group consisting of SEQ ID NOs: 5, 12, 27, 52, and 53 into which one or two substitution(s) selected from the group consisting of (a) to (d) below is introduced:

(a) the second amino acid from the N terminus is substituted with an amino acid selected from the group consisting of threonine, valine, isoleucine, leucine, phenylalanine and tyrosine;

(b) the third amino acid from the N terminus is substituted with an amino acid selected from the group consisting of leucine, phenylalanine, tyrosine, isoleucine and alanine;

(c) the seventh amino acid from the N terminus is substituted with an amino acid selected from the group consisting of leucine, isoleucine, tyrosine, valine and phenylalanine; and (d) the C-terminal amino acid is substituted with an amino acid selected from the group consisting of lysine and arginine; and (2) a peptide consisting of an amino acid sequence selected from the group consisting of SEQ ID NOs: 118, 119, and 170 into which one or two substitution(s) selected from the group consisting of (a) to (c) below is introduced:

(a) the first amino acid from the N terminus is substituted with an amino acid selected from the group consisting of aspartic acid and glutamic acid;

(b) the second amino acid from the N terminus is substituted with an amino acid selected from the group consisting of phenylalanine, tyrosine, alanine, isoleucine, leucine, and valine; and (c) the C-terminal amino acid is substituted with an amino acid selected from the group consisting of arginine and lysine; and (B) one or more types of polynucleotides encoding the peptide(s) of (A) in an expressible form;

and a container that houses an adjuvant in an amount to enhance an immune response.

* * * * *

SEQUENCE LISTING

<160> NUMBER OF SEQ ID NOS: 189

<210> SEQ ID NO 1
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 1

Met Ala Gln Lys Phe Ser Phe Ser Lys
1               5

<210> SEQ ID NO 2
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 2

Leu Thr Gln Gly Val Thr Cys Tyr Lys
1               5

<210> SEQ ID NO 3
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 3

Lys Met Met Leu Ile Thr Gln Ala Lys
1               5

<210> SEQ ID NO 4
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 4

Thr Ile Asn Glu Phe Gln Asn Leu Lys
1               5

<210> SEQ ID NO 5
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 5

Thr Ser Ser Leu Ile Ile Asn Asn Lys
1               5

<210> SEQ ID NO 6
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 6

Arg Leu Tyr Thr Lys Met Asn Leu Lys
1               5

<210> SEQ ID NO 7
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 7

Thr Ser Phe Glu Ile Ser Arg Asn Lys
1               5

<210> SEQ ID NO 8
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 8

Arg Ser His Ser Ile Phe Thr Val Lys
1               5

<210> SEQ ID NO 9
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 9

Lys Ser Ser Gly Gln Met Ala Gln Lys
1               5

<210> SEQ ID NO 10
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 10

Ser Gln Ile Lys Leu Met His Thr Lys
1               5

<210> SEQ ID NO 11
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 11

Ala Ile Ala Glu Leu His Val Gln Lys
1               5

<210> SEQ ID NO 12
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 12

Ser Ser Ala Arg Thr Gln Asn Leu Lys
1               5

<210> SEQ ID NO 13
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 13

Lys Ser His Met Glu Asn Thr Phe Lys
1               5

<210> SEQ ID NO 14
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 14

Ser Leu Gln Glu Arg Leu Tyr Thr Lys
1               5

<210> SEQ ID NO 15
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 15

Ala Leu Ile Ser Ser Asn Val Gln Lys
1               5

<210> SEQ ID NO 16
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 16

Ala Ile Phe Lys Asp Leu Val Gly Lys
1               5

<210> SEQ ID NO 17
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 17

Ile Thr Asn Asn Val Ser Gln Ile Lys
1               5

<210> SEQ ID NO 18
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 18

Asn Thr Ser Leu Leu Thr Leu Gly Lys
1               5

```
<210> SEQ ID NO 19
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 19

Ser Ile Leu Gln Ser Lys Ala Lys Lys
1               5

<210> SEQ ID NO 20
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 20

Lys Ala Phe Ile Ser His Glu Glu Lys
1               5

<210> SEQ ID NO 21
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 21

Lys Val Ala Ile Arg Pro Ser Ser Lys
1               5

<210> SEQ ID NO 22
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 22

Leu Thr Asn Asn Leu Gln Asp Met Lys
1               5

<210> SEQ ID NO 23
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 23

Gly Val Asn Leu Ala Thr Lys Lys Lys
1               5

<210> SEQ ID NO 24
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 24

Lys Leu Ser Asn Val Glu Ala Ser Lys
1               5

<210> SEQ ID NO 25
```

```
<210> SEQ ID NO 25
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 25

Ser Ser Ala Ile Thr Glu Asp Gln Lys
1               5

<210> SEQ ID NO 26
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 26

Lys Val Glu Cys Ser His Ser Ala Lys
1               5

<210> SEQ ID NO 27
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 27

Cys Ile Leu Gly Arg Leu Ser Glu Lys
1               5

<210> SEQ ID NO 28
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 28

Val Ala Ile Arg Pro Ser Ser Lys Lys
1               5

<210> SEQ ID NO 29
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 29

Lys Ser Ala Leu Leu Arg Gln Ile Lys
1               5

<210> SEQ ID NO 30
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 30

Val Ser Ser Lys Phe Gln Lys Arg Lys
1               5

<210> SEQ ID NO 31
<211> LENGTH: 9
```

```
<212> TYPE: PRT
<213> ORGANISM: Artificial Sequence
<220> FEATURE:
<223> OTHER INFORMATION: a peptide derived from MPHOSPH1

<400> SEQUENCE: 31

Thr Gln Ile Met Asp Ile Lys Pro Lys
1               5

<210> SEQ ID NO 32
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 32

Ile Ile Glu Thr Met Ser Ser Ser Lys
1               5

<210> SEQ ID NO 33
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 33

Gln Ser Phe Phe Asn Gly Lys Gly Lys
1               5

<210> SEQ ID NO 34
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 34

Arg Ile Lys Ile Asn Glu Leu Glu Lys
1               5

<210> SEQ ID NO 35
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 35

Ser Leu Asp Ser Asn Ser Asn Ser Lys
1               5

<210> SEQ ID NO 36
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 36

Val Ala Ala Leu Glu Ile Gln Leu Lys
1               5

<210> SEQ ID NO 37
<211> LENGTH: 9
<212> TYPE: PRT
```

```
<213> ORGANISM: Artificial Sequence
<220> FEATURE:
<223> OTHER INFORMATION: a peptide derived from MPHOSPH1

<400> SEQUENCE: 37

Arg Ile Ser Ser Ala Asp Pro Asp Lys
1               5

<210> SEQ ID NO 38
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 38

Leu Gln Ala Glu Val Lys Gly Tyr Lys
1               5

<210> SEQ ID NO 39
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 39

Gly Gln Val Ile Leu Met Asp Gln Lys
1               5

<210> SEQ ID NO 40
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 40

Ile Leu Thr Ala Gln Leu Thr Glu Lys
1               5

<210> SEQ ID NO 41
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 41

Lys Ile Asn Glu Leu Glu Lys Lys Lys
1               5

<210> SEQ ID NO 42
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 42

Gln Ile Gln His Val Val Glu Gly Lys
1               5

<210> SEQ ID NO 43
<211> LENGTH: 9
<212> TYPE: PRT
<213> ORGANISM: Artificial Sequence
```

```
<220> FEATURE:
<223> OTHER INFORMATION: a peptide derived from MPHOSPH1

<400> SEQUENCE: 43

Thr Val Lys Ile Pro Lys Ala Arg Lys
1               5

<210> SEQ ID NO 44
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 44

Val Thr Cys Tyr Lys Ala Lys Ile Lys
1               5

<210> SEQ ID NO 45
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 45

Thr Val Glu Val Pro Lys Asp Ser Lys
1               5

<210> SEQ ID NO 46
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 46

Ile Ala Ser Lys Ser Ala Leu Leu Arg
1               5

<210> SEQ ID NO 47
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 47

Lys Ser Lys Ile Cys Ser Glu Arg Lys
1               5

<210> SEQ ID NO 48
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 48

Ser Ser Lys Lys Thr Tyr Ser Leu Arg
1               5

<210> SEQ ID NO 49
<211> LENGTH: 9
<212> TYPE: PRT
<213> ORGANISM: Artificial Sequence
<220> FEATURE:
```

```
<223> OTHER INFORMATION: a peptide derived from MPHOSPH1

<400> SEQUENCE: 49

Ile Ile Gly Val Asn Leu Ala Thr Lys
1               5

<210> SEQ ID NO 50
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 50

Tyr Phe Gln Ser Phe Phe Asn Gly Lys
1               5

<210> SEQ ID NO 51
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 51

Arg Ala Cys Lys Asp Leu Asn Val Lys
1               5

<210> SEQ ID NO 52
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 52

Ser Thr Ser Phe Glu Ile Ser Arg Asn Lys
1               5                   10

<210> SEQ ID NO 53
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 53

Ser Ile Ile Gly Val Asn Leu Ala Thr Lys
1               5                   10

<210> SEQ ID NO 54
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 54

Ala Ser Ser Ala Arg Thr Gln Asn Leu Lys
1               5                   10

<210> SEQ ID NO 55
<211> LENGTH: 10
<212> TYPE: PRT
<213> ORGANISM: Artificial Sequence
<220> FEATURE:
<223> OTHER INFORMATION: a peptide derived from MPHOSPH1
```

```
<400> SEQUENCE: 55

Thr Thr Pro Val Thr Val Lys Ile Pro Lys
1               5                   10

<210> SEQ ID NO 56
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 56

Ser Ile Thr Asn Asn Val Ser Gln Ile Lys
1               5                   10

<210> SEQ ID NO 57
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 57

Phe Thr Tyr Gly Leu Thr Asn Ser Gly Lys
1               5                   10

<210> SEQ ID NO 58
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 58

Lys Ile Ile Glu Thr Met Ser Ser Ser Lys
1               5                   10

<210> SEQ ID NO 59
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 59

Lys Val Phe Gly Pro Ala Thr Thr Gln Lys
1               5                   10

<210> SEQ ID NO 60
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 60

Gln Met Ala Gln Lys Phe Ser Phe Ser Lys
1               5                   10

<210> SEQ ID NO 61
<211> LENGTH: 10
<212> TYPE: PRT
<213> ORGANISM: Artificial Sequence
<220> FEATURE:
<223> OTHER INFORMATION: a peptide derived from MPHOSPH1
```

```
<400> SEQUENCE: 61

Val Ser Leu Asp Ser Asn Ser Asn Ser Lys
1               5                   10

<210> SEQ ID NO 62
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 62

Ala Ser Lys Glu Asn Val Ser Gln Pro Lys
1               5                   10

<210> SEQ ID NO 63
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 63

Lys Ala Leu Ile Ser Ser Asn Val Gln Lys
1               5                   10

<210> SEQ ID NO 64
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 64

Lys Val Ala Ile Arg Pro Ser Ser Lys Lys
1               5                   10

<210> SEQ ID NO 65
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 65

Val Ser Ser Ala Ile Thr Glu Asp Gln Lys
1               5                   10

<210> SEQ ID NO 66
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 66

Ile Met Gln Pro Val Lys Asp Leu Leu Lys
1               5                   10

<210> SEQ ID NO 67
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 67
```

```
Asp Thr Ser Ser Leu Ile Ile Asn Asn Lys
1               5                   10

<210> SEQ ID NO 68
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 68

Asp Ser Leu Gln Glu Arg Leu Tyr Thr Lys
1               5                   10

<210> SEQ ID NO 69
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 69

Ser Ser Ala Ile Thr Glu Asp Gln Lys Lys
1               5                   10

<210> SEQ ID NO 70
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 70

Leu Val Ala Ala Leu Glu Ile Gln Leu Lys
1               5                   10

<210> SEQ ID NO 71
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 71

Phe Val Pro Val Ser Ser Lys Phe Gln Lys
1               5                   10

<210> SEQ ID NO 72
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 72

Val Ser Gln Ile Lys Leu Met His Thr Lys
1               5                   10

<210> SEQ ID NO 73
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 73
```

```
Leu Ala Ile Phe Lys Asp Leu Val Gly Lys
1               5                   10

<210> SEQ ID NO 74
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 74

Ile Ala Ile Ala Glu Leu His Val Gln Lys
1               5                   10

<210> SEQ ID NO 75
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 75

Arg Ile Arg Pro Phe Thr Gln Ser Glu Lys
1               5                   10

<210> SEQ ID NO 76
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 76

Asn Thr Glu Ala Asn Ser Phe Glu Ser Lys
1               5                   10

<210> SEQ ID NO 77
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 77

Asp Thr Ile Asn Glu Phe Gln Asn Leu Lys
1               5                   10

<210> SEQ ID NO 78
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 78

Gln Val Ile Leu Met Asp Gln Lys Met Lys
1               5                   10

<210> SEQ ID NO 79
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 79

Asn Ser Asn Ser Lys Ile Leu Asn Val Lys
```

```
<210> SEQ ID NO 80
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 80

Ile Leu Asp Ser Gln Thr Val Val Leu Lys
1               5                   10

<210> SEQ ID NO 81
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 81

Gln Ile Ile Lys Arg Arg Leu Arg Thr Lys
1               5                   10

<210> SEQ ID NO 82
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 82

Glu Leu Thr Gln Gly Val Thr Cys Tyr Lys
1               5                   10

<210> SEQ ID NO 83
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 83

Glu Ile Leu Thr Ala Gln Leu Thr Glu Lys
1               5                   10

<210> SEQ ID NO 84
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 84

Ile Ser Asp Asp Arg Asn Ser Ser Val Lys
1               5                   10

<210> SEQ ID NO 85
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 85

Ile Gln Phe Thr Pro Leu Gln Pro Asn Lys
1               5                   10
```

```
<210> SEQ ID NO 86
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 86

Tyr Ala Glu Asp Arg Glu Arg Phe Phe Lys
1               5                   10

<210> SEQ ID NO 87
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 87

Phe Leu Leu Thr Ile Glu Asn Glu Leu Lys
1               5                   10

<210> SEQ ID NO 88
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 88

Leu Leu Gly Asn Asp Tyr Leu Val Ser Lys
1               5                   10

<210> SEQ ID NO 89
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 89

Thr Leu Gly Lys Cys Ile Asn Val Leu Lys
1               5                   10

<210> SEQ ID NO 90
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 90

Asn Ile Ser Glu Phe Glu Glu Ser Ile Lys
1               5                   10

<210> SEQ ID NO 91
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 91

Val Gln Ile Gln His Val Val Glu Gly Lys
1               5                   10
```

```
<210> SEQ ID NO 92
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 92

Lys Leu Leu Asp Leu Ile Glu Asp Leu Lys
1               5                   10

<210> SEQ ID NO 93
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 93

Leu Thr Glu Lys Asp Ser Asp Leu Gln Lys
1               5                   10

<210> SEQ ID NO 94
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 94

Leu Ile Gln Glu Leu Glu Thr Ser Asn Lys
1               5                   10

<210> SEQ ID NO 95
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 95

Ile Ile Leu Lys Leu Glu Arg Asn Leu Lys
1               5                   10

<210> SEQ ID NO 96
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 96

Arg Ile Lys Ile Asn Glu Leu Glu Lys Lys
1               5                   10

<210> SEQ ID NO 97
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 97

Cys Ile Asn Val Leu Lys Asn Ser Glu Lys
1               5                   10
```

```
<210> SEQ ID NO 98
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 98

Tyr Val Phe Ser Ala Asp Pro Ile Ala Arg
1               5                   10

<210> SEQ ID NO 99
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 99

Ala Thr Glu Leu Glu Lys Trp Lys Glu Lys
1               5                   10

<210> SEQ ID NO 100
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 100

Ala Ile Gln Gln Tyr Glu Arg Ala Cys Lys
1               5                   10

<210> SEQ ID NO 101
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 101

Phe Gln Ser Phe Phe Asn Gly Lys Gly Lys
1               5                   10

<210> SEQ ID NO 102
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 102

Lys Thr Lys Gly Glu Leu Ile Lys Thr Lys
1               5                   10

<210> SEQ ID NO 103
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 103

Gly Val Thr Cys Tyr Lys Ala Lys Ile Lys
1               5                   10

<210> SEQ ID NO 104
```

```
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 104

Ser Leu Cys Asp Leu Ala Gly Ser Glu Arg
1               5                   10

<210> SEQ ID NO 105
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 105

Leu Leu Asp Leu Ile Glu Asp Leu Lys Lys
1               5                   10

<210> SEQ ID NO 106
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 106

Lys Ile Ile Thr Gln Asn Gln Arg Ile Lys
1               5                   10

<210> SEQ ID NO 107
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 107

Asn Val Leu Phe Asp Ser Leu Gln Glu Arg
1               5                   10

<210> SEQ ID NO 108
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 108

Val Thr Val Lys Ile Pro Lys Ala Arg Lys
1               5                   10

<210> SEQ ID NO 109
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 109

Val Ser Phe Phe Glu Ile Tyr Asn Glu Tyr
1               5                   10

<210> SEQ ID NO 110
<211> LENGTH: 10
```

<212> TYPE: PRT
<213> ORGANISM: Artificial Sequence
<220> FEATURE:
<223> OTHER INFORMATION: a peptide derived from MPHOSPH1

<400> SEQUENCE: 110

Lys Met Leu Arg Leu Ser Gln Asp Val Lys
1               5                   10

<210> SEQ ID NO 111
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 111

Asp Ser Lys Glu Ala Tyr Arg Leu Leu Lys
1               5                   10

<210> SEQ ID NO 112
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 112

Lys Leu Gln Ala Glu Val Lys Gly Tyr Lys
1               5                   10

<210> SEQ ID NO 113
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 113

Phe Gln Gln Glu Leu Ser Leu Ser Glu Lys
1               5                   10

<210> SEQ ID NO 114
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 114

Lys Leu Thr Asp Ala Lys Lys Gln Ile Lys
1               5                   10

<210> SEQ ID NO 115
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 115

Ile Ile Gly Val Asn Leu Ala Thr Lys Lys
1               5                   10

<210> SEQ ID NO 116
<211> LENGTH: 10
<212> TYPE: PRT

```
<213> ORGANISM: Artificial Sequence
<220> FEATURE:
<223> OTHER INFORMATION: a peptide derived from MPHOSPH1

<400> SEQUENCE: 116

Gln Leu Thr Asn Asn Leu Gln Asp Met Lys
1               5                   10

<210> SEQ ID NO 117
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 117

Val Leu Lys Phe Ser Ala Ile Ala Gln Lys
1               5                   10

<210> SEQ ID NO 118
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 118

Glu Phe Thr Gln Tyr Trp Ala Gln Arg
1               5

<210> SEQ ID NO 119
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 119

Asp Leu Gln Lys Trp Arg Glu Glu Arg
1               5

<210> SEQ ID NO 120
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 120

Gln Ile Met Asp Ile Lys Pro Lys Arg
1               5

<210> SEQ ID NO 121
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 121

Asn Ser Lys Ile Leu Asn Val Lys Arg
1               5

<210> SEQ ID NO 122
<211> LENGTH: 9
<212> TYPE: PRT
<213> ORGANISM: Artificial Sequence
```

```
<220> FEATURE:
<223> OTHER INFORMATION: a peptide derived from MPHOSPH1

<400> SEQUENCE: 122

His Gln Ile Ile Lys Arg Arg Leu Arg
1               5

<210> SEQ ID NO 123
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 123

Glu Ile Leu Glu Glu Asn Ala Glu Arg
1               5

<210> SEQ ID NO 124
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 124

Val Thr Val Lys Ile Pro Lys Ala Arg
1               5

<210> SEQ ID NO 125
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 125

Lys Phe Gln Lys Arg Lys Met Leu Arg
1               5

<210> SEQ ID NO 126
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 126

Glu Ser Ile Ile Leu Lys Leu Glu Arg
1               5

<210> SEQ ID NO 127
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 127

Lys Phe Gln Gln His Val Pro Phe Arg
1               5

<210> SEQ ID NO 128
<211> LENGTH: 9
<212> TYPE: PRT
<213> ORGANISM: Artificial Sequence
<220> FEATURE:
```

```
<223> OTHER INFORMATION: a peptide derived from MPHOSPH1

<400> SEQUENCE: 128

Asn Phe Asn Gln Glu Gly Val Pro Arg
1               5

<210> SEQ ID NO 129
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 129

Asp Val Lys Gly Tyr Ser Phe Ile Lys
1               5

<210> SEQ ID NO 130
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 130

Asp Met Lys His Leu Leu Gln Leu Lys
1               5

<210> SEQ ID NO 131
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 131

Ser Asn Ile Asp Leu Leu Asn Leu Arg
1               5

<210> SEQ ID NO 132
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 132

Val Phe Ser Ala Asp Pro Ile Ala Arg
1               5

<210> SEQ ID NO 133
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 133

Glu Met Lys Lys Tyr Ala Glu Asp Arg
1               5

<210> SEQ ID NO 134
<211> LENGTH: 9
<212> TYPE: PRT
<213> ORGANISM: Artificial Sequence
<220> FEATURE:
<223> OTHER INFORMATION: a peptide derived from MPHOSPH1
```

```
<400> SEQUENCE: 134

Val Ser Gln Pro Lys Arg Ala Lys Arg
1               5

<210> SEQ ID NO 135
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 135

Glu Tyr Arg Ile Gln Glu Pro Asn Arg
1               5

<210> SEQ ID NO 136
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 136

Val Ser Lys Gln Val Lys Glu Tyr Arg
1               5

<210> SEQ ID NO 137
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 137

Val Leu Phe Asp Ser Leu Gln Glu Arg
1               5

<210> SEQ ID NO 138
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 138

Asn Ile Ala Glu Ile Glu Asp Ile Arg
1               5

<210> SEQ ID NO 139
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 139

Leu Ser Thr Ser Phe Glu Ile Ser Arg
1               5

<210> SEQ ID NO 140
<211> LENGTH: 9
<212> TYPE: PRT
<213> ORGANISM: Artificial Sequence
<220> FEATURE:
<223> OTHER INFORMATION: a peptide derived from MPHOSPH1
```

```
<400> SEQUENCE: 140

Met Asn Leu Lys Pro His Arg Ser Arg
1               5

<210> SEQ ID NO 141
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 141

Val Gln Lys Glu Val Ser Val Met Arg
1               5

<210> SEQ ID NO 142
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 142

Asp Leu Phe Val Pro Val Ser Ser Lys
1               5

<210> SEQ ID NO 143
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 143

Glu Ala Lys Leu Glu Glu Val Glu Arg
1               5

<210> SEQ ID NO 144
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 144

Tyr Ile Tyr Asp Leu Phe Val Pro Val
1               5

<210> SEQ ID NO 145
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 145

Asp Leu Glu Thr Lys Asn Asn Gln Arg
1               5

<210> SEQ ID NO 146
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 146
```

Ala Phe Ile Ser His Glu Glu Lys Arg
1               5

<210> SEQ ID NO 147
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 147

Ser Phe Phe Glu Ile Tyr Asn Glu Tyr
1               5

<210> SEQ ID NO 148
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 148

Pro Val Ser Ser Lys Phe Gln Lys Arg
1               5

<210> SEQ ID NO 149
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 149

Asn Ala Thr Pro Arg Thr Asn Leu Lys
1               5

<210> SEQ ID NO 150
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 150

Asp Leu Val Gly Lys Cys Asp Thr Arg
1               5

<210> SEQ ID NO 151
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 151

Glu Asn Lys Lys Asn Ala Thr Pro Arg
1               5

<210> SEQ ID NO 152
<211> LENGTH: 9
<212> TYPE: PRT
<213> ORGANISM: Artificial Sequence
<220> FEATURE:
<223> OTHER INFORMATION: a peptide derived from MPHOSPH1

<400> SEQUENCE: 152

Asp Ser Glu Met Ser Arg Val Ile Arg
1               5

<210> SEQ ID NO 153
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 153

Asp Phe Lys Glu Thr Leu Leu Gln Glu Arg
1               5                   10

<210> SEQ ID NO 154
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 154

Phe Thr Lys Leu Asn Asn Ala Ser Ser Arg
1               5                   10

<210> SEQ ID NO 155
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 155

Asp Ser Lys Ser Lys Ile Cys Ser Glu Arg
1               5                   10

<210> SEQ ID NO 156
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 156

Tyr Thr Lys Met Asn Leu Lys Pro His Arg
1               5                   10

<210> SEQ ID NO 157
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 157

Glu Ile Ala Ser Lys Ser Ala Leu Leu Arg
1               5                   10

<210> SEQ ID NO 158
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 158

His Tyr Phe Gln Ser Phe Phe Asn Gly Lys

```
1               5                   10
```

<210> SEQ ID NO 159
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 159

```
Gln Val Ser Asp Ser Lys Glu Ala Tyr Arg
1               5                   10
```

<210> SEQ ID NO 160
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 160

```
Asn Val Ser Gln Pro Lys Arg Ala Lys Arg
1               5                   10
```

<210> SEQ ID NO 161
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 161

```
Leu Met His Thr Lys Ile Asp Glu Leu Arg
1               5                   10
```

<210> SEQ ID NO 162
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 162

```
Thr Val Lys Ile Pro Lys Ala Arg Lys Arg
1               5                   10
```

<210> SEQ ID NO 163
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 163

```
Leu Val Ser Lys Gln Val Lys Glu Tyr Arg
1               5                   10
```

<210> SEQ ID NO 164
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 164

```
Thr Met Lys Thr Gln Asn Glu Gly Glu Arg
1               5                   10
```

<210> SEQ ID NO 165
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 165

Leu Ser Asn Glu Ile Glu Thr Ala Thr Arg
1               5                   10

<210> SEQ ID NO 166
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 166

Asn Leu Lys Phe Pro Ile Ser Asp Asp Arg
1               5                   10

<210> SEQ ID NO 167
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 167

Glu Ile Leu Glu Glu Asn Ala Glu Arg Arg
1               5                   10

<210> SEQ ID NO 168
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 168

Lys Met Asn Leu Lys Pro His Arg Ser Arg
1               5                   10

<210> SEQ ID NO 169
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 169

Gln Val Gln Lys Glu Val Ser Val Met Arg
1               5                   10

<210> SEQ ID NO 170
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 170

Asp Tyr Leu Gln Val Cys Leu Arg Ile Arg
1               5                   10

<210> SEQ ID NO 171
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 171

Gln Ile Gln His Val Val Glu Gly Lys Arg
1               5                   10

<210> SEQ ID NO 172
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 172

Asp Leu Lys Lys Lys Leu Ile Asn Glu Lys
1               5                   10

<210> SEQ ID NO 173
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 173

Ile Ser Asn Ile Asp Leu Leu Asn Leu Arg
1               5                   10

<210> SEQ ID NO 174
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 174

Ser Asn Ser Lys Ile Leu Asn Val Lys Arg
1               5                   10

<210> SEQ ID NO 175
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 175

Ser Asn Phe Asn Gln Glu Gly Val Pro Arg
1               5                   10

<210> SEQ ID NO 176
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 176

Lys Pro His Arg Ser Arg Glu Tyr Leu Arg
1               5                   10

```
<210> SEQ ID NO 177
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 177

Val Met Arg Asp Glu Asp Lys Leu Leu Arg
1               5                   10

<210> SEQ ID NO 178
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 178

Thr Gln Ile Met Asp Ile Lys Pro Lys Arg
1               5                   10

<210> SEQ ID NO 179
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 179

Gln Glu Phe Thr Gln Tyr Trp Ala Gln Arg
1               5                   10

<210> SEQ ID NO 180
<211> LENGTH: 10
<212> TYPE: PRT
<213> ORGANISM: Artificial Sequence
<220> FEATURE:
<223> OTHER INFORMATION: a peptide derived from MPHOSPH1

<400> SEQUENCE: 180

Lys Ala Phe Ile Ser His Glu Glu Lys Arg
1               5                   10

<210> SEQ ID NO 181
<211> LENGTH: 22
<212> TYPE: DNA
<213> ORGANISM: Artificial Sequence
<220> FEATURE:
<223> OTHER INFORMATION: a PCR primer for the TCR analysis

<400> SEQUENCE: 181
gtctaccagg cattcgcttc at                                    22

<210> SEQ ID NO 182
<211> LENGTH: 24
<212> TYPE: DNA
<213> ORGANISM: Artificial Sequence
<220> FEATURE:
<223> OTHER INFORMATION: a PCR primer for the TCR analysis

<400> SEQUENCE: 182
tcagctggac cacagccgca gcgt                                  24

<210> SEQ ID NO 183
<211> LENGTH: 21
<212> TYPE: DNA
```

```
<213> ORGANISM: Artificial Sequence
<220> FEATURE:
<223> OTHER INFORMATION: a PCR primer for the TCR analysis

<400> SEQUENCE: 183
tcagaaatcc tttctcttga c                                            21

<210> SEQ ID NO 184
<211> LENGTH: 24
<212> TYPE: DNA
<213> ORGANISM: Artificial Sequence
<220> FEATURE:
<223> OTHER INFORMATION: a PCR primer for the TCR analysis

<400> SEQUENCE: 184
ctagcctctg gaatcctttc tctt                                         24

<210> SEQ ID NO 185
<211> LENGTH: 6339
<212> TYPE: DNA
<213> ORGANISM: Homo sapiens
<220> FEATURE:
<221> NAME/KEY: CDS
<222> LOCATION: (93)..(5435)

<400> SEQUENCE: 185
```

| | |
|---|---:|
| agtgcggtgc cctggccgcc attgtttgaa tttgaaaacg gtaacatcgc agtgctgctc | 60 |
| gcgggtctgg ctagtcaggc gaagtttgca ga atg gaa tct aat ttt aat caa | 113 |
|                      Met Glu Ser Asn Phe Asn Gln | |
|                       1     5 | |
| gag gga gta cct cga cca tct tat gtt ttt agt gct gac cca att gca | 161 |
| Glu Gly Val Pro Arg Pro Ser Tyr Val Phe Ser Ala Asp Pro Ile Ala | |
|   10         15         20 | |
| agg cct tca gaa ata aat ttc gat ggc att aag ctt gat ctg tct cat | 209 |
| Arg Pro Ser Glu Ile Asn Phe Asp Gly Ile Lys Leu Asp Leu Ser His | |
| 25         30         35 | |
| gaa ttt tcc tta gtt gct cca aat act gag gca aac agt ttc gaa tct | 257 |
| Glu Phe Ser Leu Val Ala Pro Asn Thr Glu Ala Asn Ser Phe Glu Ser | |
| 40         45         50         55 | |
| aaa gat tat ctc cag gtt tgt ctt cga ata aga cca ttt aca cag tca | 305 |
| Lys Asp Tyr Leu Gln Val Cys Leu Arg Ile Arg Pro Phe Thr Gln Ser | |
|          60         65         70 | |
| gaa aaa gaa ctt gag tct gag ggc tgt gtg cat att ctg gat tca cag | 353 |
| Glu Lys Glu Leu Glu Ser Glu Gly Cys Val His Ile Leu Asp Ser Gln | |
|     75         80         85 | |
| act gtt gtg ctg aaa gag cct caa tgc atc ctt ggt cgg tta agt gaa | 401 |
| Thr Val Val Leu Lys Glu Pro Gln Cys Ile Leu Gly Arg Leu Ser Glu | |
| 90         95         100 | |
| aaa agc tca ggg cag atg gca cag aaa ttc agt ttt tcc aag gtt ttt | 449 |
| Lys Ser Ser Gly Gln Met Ala Gln Lys Phe Ser Phe Ser Lys Val Phe | |
|          105         110         115 | |
| ggc cca gca act aca cag aag gaa ttc ttt cag ggt tgc att atg caa | 497 |
| Gly Pro Ala Thr Thr Gln Lys Glu Phe Phe Gln Gly Cys Ile Met Gln | |
| 120         125         130         135 | |
| cca gta aaa gac ctc ttg aaa gga cag agt cgt ctg att ttt act tac | 545 |
| Pro Val Lys Asp Leu Leu Lys Gly Gln Ser Arg Leu Ile Phe Thr Tyr | |
|          140         145         150 | |
| ggg cta acc aat tca gga aaa aca tat aca ttt caa ggg aca gaa gaa | 593 |
| Gly Leu Thr Asn Ser Gly Lys Thr Tyr Thr Phe Gln Gly Thr Glu Glu | |
|              155         160         165 | |
| aat att ggc att ctg cct cga act ttg aat gta tta ttt gat agt ctt | 641 |
| Asn Ile Gly Ile Leu Pro Arg Thr Leu Asn Val Leu Phe Asp Ser Leu | |

|  |  |  |  |  |  |  |  |  |
|---|---|---|---|---|---|---|---|---|
| | 170 | | | 175 | | | 180 | |

```
caa gaa aga ctg tat aca aag atg aac ctt aaa cca cat aga tcc aga         689
Gln Glu Arg Leu Tyr Thr Lys Met Asn Leu Lys Pro His Arg Ser Arg
        185                 190                 195 gaa tac tta agg tta tca tca gaa caa gag aaa gaa gaa att gct agc         737
Glu Tyr Leu Arg Leu Ser Ser Glu Gln Glu Lys Glu Glu Ile Ala Ser
200                 205                 210                 215 aaa agt gca ttg ctt cgg caa att aaa gag gtt act gtg cat aat gat         785
Lys Ser Ala Leu Leu Arg Gln Ile Lys Glu Val Thr Val His Asn Asp
                220                 225                 230 agt gat gat act ctt tat gga agt tta act aac tct ttg aat atc tca         833
Ser Asp Asp Thr Leu Tyr Gly Ser Leu Thr Asn Ser Leu Asn Ile Ser
            235                 240                 245 gag ttt gaa gaa tcc ata aaa gat tat gaa caa gcc aac ttg aat atg         881
Glu Phe Glu Glu Ser Ile Lys Asp Tyr Glu Gln Ala Asn Leu Asn Met
        250                 255                 260 gct aat agt ata aaa ttt tct gtg tgg gtt tct ttc ttt gaa att tac         929
Ala Asn Ser Ile Lys Phe Ser Val Trp Val Ser Phe Phe Glu Ile Tyr
    265                 270                 275 aat gaa tat att tat gac tta ttt gtt cct gta tca tct aaa ttc caa         977
Asn Glu Tyr Ile Tyr Asp Leu Phe Val Pro Val Ser Ser Lys Phe Gln
280                 285                 290                 295 aag aga aag atg ctg cgc ctt tcc caa gac gta aag ggc tat tct ttt        1025
Lys Arg Lys Met Leu Arg Leu Ser Gln Asp Val Lys Gly Tyr Ser Phe
                300                 305                 310 ata aaa gat cta caa tgg att caa gta tct gat tcc aaa gaa gcc tat        1073
Ile Lys Asp Leu Gln Trp Ile Gln Val Ser Asp Ser Lys Glu Ala Tyr
            315                 320                 325 aga ctt tta aaa cta gga ata aag cac cag agt gtt gcc ttc aca aaa        1121
Arg Leu Leu Lys Leu Gly Ile Lys His Gln Ser Val Ala Phe Thr Lys
        330                 335                 340 ttg aat aat gct tcc agt aga agt cac agc ata ttc act gtt aaa ata        1169
Leu Asn Asn Ala Ser Ser Arg Ser His Ser Ile Phe Thr Val Lys Ile
    345                 350                 355 tta cag att gaa gat tct gaa atg tct cgt gta att cga gtc agt gaa        1217
Leu Gln Ile Glu Asp Ser Glu Met Ser Arg Val Ile Arg Val Ser Glu
360                 365                 370                 375 tta tct tta tgt gat ctt gct ggt tca gaa cga act atg aag aca cag        1265
Leu Ser Leu Cys Asp Leu Ala Gly Ser Glu Arg Thr Met Lys Thr Gln
                380                 385                 390 aat gaa ggt gaa agg tta aga gag act ggg aat atc aac act tct tta        1313
Asn Glu Gly Glu Arg Leu Arg Glu Thr Gly Asn Ile Asn Thr Ser Leu
            395                 400                 405 ttg act ctg gga aag tgt att aac gtc ttg aag aat agt gaa aag tca        1361
Leu Thr Leu Gly Lys Cys Ile Asn Val Leu Lys Asn Ser Glu Lys Ser
        410                 415                 420 aag ttt caa cag cat gtg cct ttc cgg gaa agt aaa ctg act cac tat        1409
Lys Phe Gln Gln His Val Pro Phe Arg Glu Ser Lys Leu Thr His Tyr
    425                 430                 435 ttt caa agt ttt ttt aat ggt aaa ggg aaa att tgt atg att gtc aat        1457
Phe Gln Ser Phe Phe Asn Gly Lys Gly Lys Ile Cys Met Ile Val Asn
440                 445                 450                 455 atc agc caa tgt tat tta gcc tat gat gaa aca ctc aat gta ttg aag        1505
Ile Ser Gln Cys Tyr Leu Ala Tyr Asp Glu Thr Leu Asn Val Leu Lys
                460                 465                 470 ttc tcc gcc att gca caa aaa gtt tgt gtc cca gac act tta aat tcc        1553
Phe Ser Ala Ile Ala Gln Lys Val Cys Val Pro Asp Thr Leu Asn Ser
            475                 480                 485 tct caa gag aaa tta ttt gga cct gtc aaa tct tct caa gat gta tca        1601
```

```
Ser Gln Glu Lys Leu Phe Gly Pro Val Lys Ser Ser Gln Asp Val Ser
        490                 495                 500 cta gac agt aat tca aac agt aaa ata tta aat gta aaa aga gcc acc       1649
Leu Asp Ser Asn Ser Asn Ser Lys Ile Leu Asn Val Lys Arg Ala Thr
    505                 510                 515 att tca tgg gaa aat agt cta gaa gat ttg atg gaa gac gag gat ttg       1697
Ile Ser Trp Glu Asn Ser Leu Glu Asp Leu Met Glu Asp Glu Asp Leu
520                 525                 530                 535 gtt gag gag cta gaa aac gct gaa gaa act caa aat gtg gaa act aaa       1745
Val Glu Glu Leu Glu Asn Ala Glu Glu Thr Gln Asn Val Glu Thr Lys
                540                 545                 550 ctt ctt gat gaa gat cta gat aaa aca tta gag gaa aat aag gct ttc       1793
Leu Leu Asp Glu Asp Leu Asp Lys Thr Leu Glu Glu Asn Lys Ala Phe
            555                 560                 565 att agc cac gag gag aaa aga aaa ctg ttg gac tta ata gaa gac ttg       1841
Ile Ser His Glu Glu Lys Arg Lys Leu Leu Asp Leu Ile Glu Asp Leu
        570                 575                 580 aaa aaa aaa ctg ata aat gaa aaa aag gaa aaa tta acc ttg gaa ttt       1889
Lys Lys Lys Leu Ile Asn Glu Lys Lys Glu Lys Leu Thr Leu Glu Phe
585                 590                 595 aaa att cga gaa gaa gtt aca cag gag ttt act cag tat tgg gct caa       1937
Lys Ile Arg Glu Glu Val Thr Gln Glu Phe Thr Gln Tyr Trp Ala Gln
600                 605                 610                 615 cgg gaa gct gac ttt aag gag act ctg ctt caa gaa cga gag ata tta       1985
Arg Glu Ala Asp Phe Lys Glu Thr Leu Leu Gln Glu Arg Glu Ile Leu
                620                 625                 630 gaa gaa aat gct gaa cgt cgt ttg gct atc ttc aag gat ttg gtt ggt       2033
Glu Glu Asn Ala Glu Arg Arg Leu Ala Ile Phe Lys Asp Leu Val Gly
            635                 640                 645 aaa tgt gac act cga gaa gaa gca gcg aaa gac att tgt gcc aca aaa       2081
Lys Cys Asp Thr Arg Glu Glu Ala Ala Lys Asp Ile Cys Ala Thr Lys
        650                 655                 660 gtt gaa act gaa gaa gct act gct tgt tta gaa cta aag ttt aat caa       2129
Val Glu Thr Glu Glu Ala Thr Ala Cys Leu Glu Leu Lys Phe Asn Gln
    665                 670                 675 att aaa gct gaa tta gct aaa acc aaa gga gaa tta atc aaa acc aaa       2177
Ile Lys Ala Glu Leu Ala Lys Thr Lys Gly Glu Leu Ile Lys Thr Lys
680                 685                 690                 695 gaa gag tta aaa aag aga gaa aat gaa tca gat tca ttg att caa gag       2225
Glu Glu Leu Lys Lys Arg Glu Asn Glu Ser Asp Ser Leu Ile Gln Glu
                700                 705                 710 ctt gag aca tct aat aag aaa ata att aca cag aat caa aga att aaa       2273
Leu Glu Thr Ser Asn Lys Lys Ile Ile Thr Gln Asn Gln Arg Ile Lys
            715                 720                 725 gaa ttg ata aat ata att gat caa aaa gaa gat act atc aac gaa ttt       2321
Glu Leu Ile Asn Ile Ile Asp Gln Lys Glu Asp Thr Ile Asn Glu Phe
        730                 735                 740 cag aac cta aag tct cat atg gaa aac aca ttt aaa tgc aat gac aag       2369
Gln Asn Leu Lys Ser His Met Glu Asn Thr Phe Lys Cys Asn Asp Lys
    745                 750                 755 gct gat aca tct tct tta ata ata aac aat aaa ttg att tgt aat gaa       2417
Ala Asp Thr Ser Ser Leu Ile Ile Asn Asn Lys Leu Ile Cys Asn Glu
760                 765                 770                 775 aca gtt gaa gta cct aag gac agc aaa tct aaa atc tgt tca gaa aga       2465
Thr Val Glu Val Pro Lys Asp Ser Lys Ser Lys Ile Cys Ser Glu Arg
                780                 785                 790 aaa aga gta aat gaa aat gaa ctt cag caa gat gaa cca cca gca aag       2513
Lys Arg Val Asn Glu Asn Glu Leu Gln Gln Asp Glu Pro Pro Ala Lys
            795                 800                 805
```

| | |
|---|---|
| aaa ggg tct atc cat gtt agt tca gct atc act gaa gac caa aag aaa<br>Lys Gly Ser Ile His Val Ser Ser Ala Ile Thr Glu Asp Gln Lys Lys<br>           810                   815               820 | 2561 |
| agt gaa gaa gtg cga ccg aac att gca gaa att gaa gac atc aga gtt<br>Ser Glu Glu Val Arg Pro Asn Ile Ala Glu Ile Glu Asp Ile Arg Val<br>825                 830                   835 | 2609 |
| tta caa gaa aat aat gaa gga ctg aga gca ttt tta ctc act att gag<br>Leu Gln Glu Asn Asn Glu Gly Leu Arg Ala Phe Leu Leu Thr Ile Glu<br>840                 845              850             855 | 2657 |
| aat gaa ctt aaa aat gaa aag gaa gaa aaa gca gaa tta aat aaa cag<br>Asn Glu Leu Lys Asn Glu Lys Glu Glu Lys Ala Glu Leu Asn Lys Gln<br>           860                   865               870 | 2705 |
| att gtt cat ttt cag cag gaa ctt tct ctt tct gaa aaa aag aat tta<br>Ile Val His Phe Gln Gln Glu Leu Ser Leu Ser Glu Lys Lys Asn Leu<br>875                 880              885 | 2753 |
| act tta agt aaa gag gtc caa caa att cag tca aat tat gat att gca<br>Thr Leu Ser Lys Glu Val Gln Gln Ile Gln Ser Asn Tyr Asp Ile Ala<br>           890                   895               900 | 2801 |
| att gct gaa tta cat gtg cag aaa agt aaa aat caa gaa cag gag gaa<br>Ile Ala Glu Leu His Val Gln Lys Ser Lys Asn Gln Glu Gln Glu Glu<br>905                 910                   915 | 2849 |
| aag atc atg aaa ttg tca aat gag ata gaa act gct aca aga agc att<br>Lys Ile Met Lys Leu Ser Asn Glu Ile Glu Thr Ala Thr Arg Ser Ile<br>920                 925              930             935 | 2897 |
| aca aat aat gtt tca caa ata aaa tta atg cac acg aaa ata gac gaa<br>Thr Asn Asn Val Ser Gln Ile Lys Leu Met His Thr Lys Ile Asp Glu<br>           940                   945               950 | 2945 |
| cta cgt act ctt gat tca gtt tct cag att tca aac ata gat ttg ctc<br>Leu Arg Thr Leu Asp Ser Val Ser Gln Ile Ser Asn Ile Asp Leu Leu<br>955                 960              965 | 2993 |
| aat ctc agg gat ctg tca aat ggt tct gag gag gat aat ttg cca aat<br>Asn Leu Arg Asp Leu Ser Asn Gly Ser Glu Glu Asp Asn Leu Pro Asn<br>           970                   975               980 | 3041 |
| aca cag tta gac ctt tta ggt aat gat tat ttg gta agt aag caa gtt<br>Thr Gln Leu Asp Leu Leu Gly Asn Asp Tyr Leu Val Ser Lys Gln Val<br>985                 990              995 | 3089 |
| aaa gaa tat cga att caa gaa ccc aat agg gaa aat tct ttc cac<br>Lys Glu Tyr Arg Ile Gln Glu Pro Asn Arg Glu Asn Ser Phe His<br>1000              1005               1010 | 3134 |
| tct agt att gaa gct att tgg gaa gaa tgt aaa gag att gtg aag<br>Ser Ser Ile Glu Ala Ile Trp Glu Glu Cys Lys Glu Ile Val Lys<br>1015              1020               1025 | 3179 |
| gcc tct tcc aaa aaa agt cat cag att gag gaa ctg gaa caa caa<br>Ala Ser Ser Lys Lys Ser His Gln Ile Glu Glu Leu Glu Gln Gln<br>1030              1035               1040 | 3224 |
| att gaa aaa ttg cag gca gaa gta aaa ggc tat aag gat gaa aac<br>Ile Glu Lys Leu Gln Ala Glu Val Lys Gly Tyr Lys Asp Glu Asn<br>1045              1050               1055 | 3269 |
| aat aga cta aag gag aag gag cat aaa aac caa gat gac cta cta<br>Asn Arg Leu Lys Glu Lys Glu His Lys Asn Gln Asp Asp Leu Leu<br>1060              1065               1070 | 3314 |
| aaa gaa aaa gaa act ctt ata cag cag ctg aaa gaa gaa ttg caa<br>Lys Glu Lys Glu Thr Leu Ile Gln Gln Leu Lys Glu Glu Leu Gln<br>1075              1080               1085 | 3359 |
| gaa aaa aat gtt act ctt gat gtt caa ata cag cat gta gtt gaa<br>Glu Lys Asn Val Thr Leu Asp Val Gln Ile Gln His Val Val Glu<br>1090              1095               1100 | 3404 |
| gga aag aga gcg ctt tca gaa ctt aca caa ggt gtt act tgc tat<br>Gly Lys Arg Ala Leu Ser Glu Leu Thr Gln Gly Val Thr Cys Tyr<br>1105              1110               1115 | 3449 |

| | | | | | | | | | | | | | | |
|---|---|---|---|---|---|---|---|---|---|---|---|---|---|---|
| aag | gca | aaa | ata | aag | gaa | ctt | gaa | aca | att | tta | gag | act | cag | aaa | 3494 |
| Lys | Ala | Lys | Ile | Lys | Glu | Leu | Glu | Thr | Ile | Leu | Glu | Thr | Gln | Lys | |
| 1120 | | | | 1125 | | | | | 1130 | | | | | | |

```
aag gca aaa ata aag gaa ctt gaa aca att tta gag act cag aaa         3494
Lys Ala Lys Ile Lys Glu Leu Glu Thr Ile Leu Glu Thr Gln Lys
1120             1125                1130 gtt gaa tgt agt cat tca gcc aag tta gaa caa gac att ttg gaa         3539
Val Glu Cys Ser His Ser Ala Lys Leu Glu Gln Asp Ile Leu Glu
1135             1140                1145 aag gaa tct atc atc tta aag cta gaa aga aat ttg aag gaa ttt         3584
Lys Glu Ser Ile Ile Leu Lys Leu Glu Arg Asn Leu Lys Glu Phe
1150             1155                1160 caa gaa cat ctt cag gat tct gtc aaa aac acc aaa gat tta aat         3629
Gln Glu His Leu Gln Asp Ser Val Lys Asn Thr Lys Asp Leu Asn
1165             1170                1175 gta aag gaa ctc aag ctg aaa gaa gaa atc aca cag tta aca aat         3674
Val Lys Glu Leu Lys Leu Lys Glu Glu Ile Thr Gln Leu Thr Asn
1180             1185                1190 aat ttg caa gat atg aaa cat tta ctt caa tta aaa gaa gaa gaa         3719
Asn Leu Gln Asp Met Lys His Leu Leu Gln Leu Lys Glu Glu Glu
1195             1200                1205 gaa gaa acc aac agg caa gaa aca gaa aaa ttg aaa gag gaa ctc         3764
Glu Glu Thr Asn Arg Gln Glu Thr Glu Lys Leu Lys Glu Glu Leu
1210             1215                1220 tct gca agc tct gct cgt acc cag aat ctg aaa gca gat ctt cag         3809
Ser Ala Ser Ser Ala Arg Thr Gln Asn Leu Lys Ala Asp Leu Gln
1225             1230                1235 agg aag gaa gaa gat tat gct gac ctg aaa gag aaa ctg act gat         3854
Arg Lys Glu Glu Asp Tyr Ala Asp Leu Lys Glu Lys Leu Thr Asp
1240             1245                1250 gcc aaa aag cag att aag caa gta cag aaa gag gta tct gta atg         3899
Ala Lys Lys Gln Ile Lys Gln Val Gln Lys Glu Val Ser Val Met
1255             1260                1265 cgt gat gag gat aaa tta ctg agg att aaa att aat gaa ctg gag         3944
Arg Asp Glu Asp Lys Leu Leu Arg Ile Lys Ile Asn Glu Leu Glu
1270             1275                1280 aaa aag aaa aac cag tgt tct cag gaa tta gat atg aaa cag cga         3989
Lys Lys Lys Asn Gln Cys Ser Gln Glu Leu Asp Met Lys Gln Arg
1285             1290                1295 acc att cag caa ctc aag gag cag tta aat aat cag aaa gtg gaa         4034
Thr Ile Gln Gln Leu Lys Glu Gln Leu Asn Asn Gln Lys Val Glu
1300             1305                1310 gaa gct ata caa cag tat gag aga gca tgc aaa gat cta aat gtt         4079
Glu Ala Ile Gln Gln Tyr Glu Arg Ala Cys Lys Asp Leu Asn Val
1315             1320                1325 aaa gag aaa ata att gaa gac atg cga atg aca cta gaa gaa cag         4124
Lys Glu Lys Ile Ile Glu Asp Met Arg Met Thr Leu Glu Glu Gln
1330             1335                1340 gaa caa act cag gta gaa cag gat caa gtg ctt gag gct aaa tta         4169
Glu Gln Thr Gln Val Glu Gln Asp Gln Val Leu Glu Ala Lys Leu
1345             1350                1355 gag gaa gtt gaa agg ctg gcc aca gaa ttg gaa aaa tgg aag gaa         4214
Glu Glu Val Glu Arg Leu Ala Thr Glu Leu Glu Lys Trp Lys Glu
1360             1365                1370 aaa tgc aat gat ttg gaa acc aaa aac aat caa agg tca aat aaa         4259
Lys Cys Asn Asp Leu Glu Thr Lys Asn Asn Gln Arg Ser Asn Lys
1375             1380                1385 gaa cat gag aac aac aca gat gtg ctt gga aag ctc act aat ctt         4304
Glu His Glu Asn Asn Thr Asp Val Leu Gly Lys Leu Thr Asn Leu
1390             1395                1400 caa gat gag tta cag gag tct gaa cag aaa tat aat gct gat aga         4349
Gln Asp Glu Leu Gln Glu Ser Glu Gln Lys Tyr Asn Ala Asp Arg
```

-continued

|     |     |     |     |     |     |     |     |     |     |     |     |     |     |     |      |
|-----|-----|-----|-----|-----|-----|-----|-----|-----|-----|-----|-----|-----|-----|-----|------|
|     |     |     |     | 1405 |     |     |     |     | 1410 |     |     |     |     | 1415 |      |
| aag | aaa | tgg | tta | gaa | gaa | aaa | atg | atg | ctt | atc | act | caa | gcg | aaa | 4394 |
| Lys | Lys | Trp | Leu | Glu | Glu | Lys | Met | Met | Leu | Ile | Thr | Gln | Ala | Lys |      |
| 1420 |    |     |     |     | 1425 |    |     |     |     | 1430 |    |     |     |     |      |
| gaa | gca | gag | aat | ata | cga | aat | aaa | gag | atg | aaa | aaa | tat | gct | gag | 4439 |
| Glu | Ala | Glu | Asn | Ile | Arg | Asn | Lys | Glu | Met | Lys | Lys | Tyr | Ala | Glu |      |
| 1435 |    |     |     |     | 1440 |    |     |     |     | 1445 |    |     |     |     |      |
| gac | agg | gag | cgt | ttt | ttt | aag | caa | cag | aat | gaa | atg | gaa | ata | ctg | 4484 |
| Asp | Arg | Glu | Arg | Phe | Phe | Lys | Gln | Gln | Asn | Glu | Met | Glu | Ile | Leu |      |
| 1450 |    |     |     |     | 1455 |    |     |     |     | 1460 |    |     |     |     |      |
| aca | gcc | cag | ctg | aca | gag | aaa | gat | agt | gac | ctt | caa | aag | tgg | cga | 4529 |
| Thr | Ala | Gln | Leu | Thr | Glu | Lys | Asp | Ser | Asp | Leu | Gln | Lys | Trp | Arg |      |
| 1465 |    |     |     |     | 1470 |    |     |     |     | 1475 |    |     |     |     |      |
| gaa | gaa | cga | gat | caa | ctg | gtt | gca | gct | tta | gaa | ata | cag | cta | aaa | 4574 |
| Glu | Glu | Arg | Asp | Gln | Leu | Val | Ala | Ala | Leu | Glu | Ile | Gln | Leu | Lys |      |
| 1480 |    |     |     |     | 1485 |    |     |     |     | 1490 |    |     |     |     |      |
| gca | ctg | ata | tcc | agt | aat | gta | cag | aaa | gat | aat | gaa | att | gaa | caa | 4619 |
| Ala | Leu | Ile | Ser | Ser | Asn | Val | Gln | Lys | Asp | Asn | Glu | Ile | Glu | Gln |      |
| 1495 |    |     |     |     | 1500 |    |     |     |     | 1505 |    |     |     |     |      |
| cta | aaa | agg | atc | ata | tca | gag | act | tct | aaa | ata | gaa | aca | caa | atc | 4664 |
| Leu | Lys | Arg | Ile | Ile | Ser | Glu | Thr | Ser | Lys | Ile | Glu | Thr | Gln | Ile |      |
| 1510 |    |     |     |     | 1515 |    |     |     |     | 1520 |    |     |     |     |      |
| atg | gat | atc | aag | ccc | aaa | cgt | att | agt | tca | gca | gat | cct | gac | aaa | 4709 |
| Met | Asp | Ile | Lys | Pro | Lys | Arg | Ile | Ser | Ser | Ala | Asp | Pro | Asp | Lys |      |
| 1525 |    |     |     |     | 1530 |    |     |     |     | 1535 |    |     |     |     |      |
| ctt | caa | act | gaa | cct | cta | tcg | aca | agt | ttt | gaa | att | tcc | aga | aat | 4754 |
| Leu | Gln | Thr | Glu | Pro | Leu | Ser | Thr | Ser | Phe | Glu | Ile | Ser | Arg | Asn |      |
| 1540 |    |     |     |     | 1545 |    |     |     |     | 1550 |    |     |     |     |      |
| aaa | ata | gag | gat | gga | tct | gta | gtc | ctt | gac | tct | tgt | gaa | gtg | tca | 4799 |
| Lys | Ile | Glu | Asp | Gly | Ser | Val | Val | Leu | Asp | Ser | Cys | Glu | Val | Ser |      |
| 1555 |    |     |     |     | 1560 |    |     |     |     | 1565 |    |     |     |     |      |
| aca | gaa | aat | gat | caa | agc | act | cga | ttt | cca | aaa | cct | gag | tta | gag | 4844 |
| Thr | Glu | Asn | Asp | Gln | Ser | Thr | Arg | Phe | Pro | Lys | Pro | Glu | Leu | Glu |      |
| 1570 |    |     |     |     | 1575 |    |     |     |     | 1580 |    |     |     |     |      |
| att | caa | ttt | aca | cct | tta | cag | cca | aac | aaa | atg | gca | gtg | aaa | cac | 4889 |
| Ile | Gln | Phe | Thr | Pro | Leu | Gln | Pro | Asn | Lys | Met | Ala | Val | Lys | His |      |
| 1585 |    |     |     |     | 1590 |    |     |     |     | 1595 |    |     |     |     |      |
| cct | ggt | tgt | acc | aca | cca | gtg | aca | gtt | aag | att | ccc | aag | gct | cgg | 4934 |
| Pro | Gly | Cys | Thr | Thr | Pro | Val | Thr | Val | Lys | Ile | Pro | Lys | Ala | Arg |      |
| 1600 |    |     |     |     | 1605 |    |     |     |     | 1610 |    |     |     |     |      |
| aag | agg | aag | agt | aat | gaa | atg | gag | gag | gac | ttg | gtg | aaa | tgt | gaa | 4979 |
| Lys | Arg | Lys | Ser | Asn | Glu | Met | Glu | Glu | Asp | Leu | Val | Lys | Cys | Glu |      |
| 1615 |    |     |     |     | 1620 |    |     |     |     | 1625 |    |     |     |     |      |
| aat | aag | aag | aat | gct | aca | ccc | aga | act | aat | ttg | aaa | ttt | cct | att | 5024 |
| Asn | Lys | Lys | Asn | Ala | Thr | Pro | Arg | Thr | Asn | Leu | Lys | Phe | Pro | Ile |      |
| 1630 |    |     |     |     | 1635 |    |     |     |     | 1640 |    |     |     |     |      |
| tca | gat | gat | aga | aat | tct | tct | gtc | aaa | aag | gaa | caa | aag | gtt | gcc | 5069 |
| Ser | Asp | Asp | Arg | Asn | Ser | Ser | Val | Lys | Lys | Glu | Gln | Lys | Val | Ala |      |
| 1645 |    |     |     |     | 1650 |    |     |     |     | 1655 |    |     |     |     |      |
| ata | cgt | cca | tca | tct | aag | aaa | aca | tat | tct | tta | cgg | agt | cag | gca | 5114 |
| Ile | Arg | Pro | Ser | Ser | Lys | Lys | Thr | Tyr | Ser | Leu | Arg | Ser | Gln | Ala |      |
| 1660 |    |     |     |     | 1665 |    |     |     |     | 1670 |    |     |     |     |      |
| tcc | ata | att | ggt | gta | aac | ctg | gcc | act | aag | aaa | aaa | gaa | gga | aca | 5159 |
| Ser | Ile | Ile | Gly | Val | Asn | Leu | Ala | Thr | Lys | Lys | Lys | Glu | Gly | Thr |      |
| 1675 |    |     |     |     | 1680 |    |     |     |     | 1685 |    |     |     |     |      |
| cta | cag | aaa | ttt | gga | gac | ttc | tta | caa | cat | tct | ccc | tca | att | ctt | 5204 |
| Leu | Gln | Lys | Phe | Gly | Asp | Phe | Leu | Gln | His | Ser | Pro | Ser | Ile | Leu |      |
| 1690 |    |     |     |     | 1695 |    |     |     |     | 1700 |    |     |     |     |      |
| caa | tca | aaa | gca | aag | aag | ata | att | gaa | aca | atg | agc | tct | tca | aag | 5249 |

| | | | | | | | | | | | |
|---|---|---|---|---|---|---|---|---|---|---|---|
| Gln | Ser | Lys | Ala | Lys | Lys | Ile | Ile | Glu | Thr | Met | Ser Ser Ser Lys |
| 1705 | | | | 1710 | | | | | 1715 | | |

```
ctc tca aat gta gaa gca agt aaa gaa aat gtg tct caa cca aaa      5294
Leu Ser Asn Val Glu Ala Ser Lys Glu Asn Val Ser Gln Pro Lys
1720                1725                1730 cga gcc aaa cgg aaa tta tac aca agt gaa att tca tct cct att      5339
Arg Ala Lys Arg Lys Leu Tyr Thr Ser Glu Ile Ser Ser Pro Ile
1735                1740                1745 gat ata tca ggc caa gtg att tta atg gac cag aaa atg aag gag      5384
Asp Ile Ser Gly Gln Val Ile Leu Met Asp Gln Lys Met Lys Glu
1750                1755                1760 agt gat cac cag att atc aaa cga cga ctt cga aca aaa aca gcc      5429
Ser Asp His Gln Ile Ile Lys Arg Arg Leu Arg Thr Lys Thr Ala
1765                1770                1775 aaa taa atcacttatg gaaatgttta atataaattt tatagtcata gtcattggaa   5485
Lys
1780 cttgcatcct gtattgtaaa tataaatgta tatattatgc attaaatcac tctgcatata  5545 gattgctgtt ttatacatag tataatttta attcaataaa tgagtcaaaa tttgtatatt  5605 tttataaggc tttttttataa tagcttcttt caaactgtat ttccctatta tctcagacat  5665 tggatcagtg aagatcctag gaaagaggct gttattctca tttattttgc tatacaggat  5725 gtaataggtc aggtatttgg tttacttata tttaacaatg tcttatgaat tttttttact  5785 ttatctgtta tacaactgat tttacatatc tgtttggatt atagctagga tttggagaat  5845 aagtgtgtac agatcacaaa acatgtatat acattattta gaaaagatct caagtcttta  5905 attagaatgt ctcacttatt ttgtaaacat tttgtgggta catagtacat gtatatattt  5965 acggggtatg tgagatgttt tgacacaggc atgcaatgtg aaatacgtgt atcatggaga  6025 atgaggtatc catcccctca agcatttttc ctttgaatta cagataatcc aattacattc  6085 tttagatcat ttaaaaatat acaagtaagt tattattgat tatagtcact ctattgtgct  6145 atcagatagt agatcattct ttttatctta tttgtttttg tacccattaa ccatccccac  6205 ctccccctgc aaccgtcagt acccttacca gccactggta accattcttc tactctgtat  6265 gcccatgagg tcaattgatt tattttttag atcccataaa taaatgagaa catgcagtct  6325 ttgtcaaaaa aaaa                                                   6339
```

<210> SEQ ID NO 186
<211> LENGTH: 1780
<212> TYPE: PRT
<213> ORGANISM: Homo sapiens

<400> SEQUENCE: 186

| Met | Glu | Ser | Asn | Phe | Asn | Gln | Glu | Gly | Val | Pro | Arg | Pro | Ser | Tyr | Val |
|---|---|---|---|---|---|---|---|---|---|---|---|---|---|---|---|
| 1 | | | | 5 | | | | | 10 | | | | | 15 | |

| Phe | Ser | Ala | Asp | Pro | Ile | Ala | Arg | Pro | Ser | Glu | Ile | Asn | Phe | Asp | Gly |
|---|---|---|---|---|---|---|---|---|---|---|---|---|---|---|---|
| | | | 20 | | | | | 25 | | | | | 30 | | |

| Ile | Lys | Leu | Asp | Leu | Ser | His | Glu | Phe | Ser | Leu | Val | Ala | Pro | Asn | Thr |
|---|---|---|---|---|---|---|---|---|---|---|---|---|---|---|---|
| | | | 35 | | | | | 40 | | | | | 45 | | |

| Glu | Ala | Asn | Ser | Phe | Glu | Ser | Lys | Asp | Tyr | Leu | Gln | Val | Cys | Leu | Arg |
|---|---|---|---|---|---|---|---|---|---|---|---|---|---|---|---|
| | 50 | | | | | 55 | | | | | 60 | | | | |

| Ile | Arg | Pro | Phe | Thr | Gln | Ser | Glu | Lys | Glu | Leu | Glu | Ser | Glu | Gly | Cys |
|---|---|---|---|---|---|---|---|---|---|---|---|---|---|---|---|
| 65 | | | | | 70 | | | | | 75 | | | | | 80 |

| Val | His | Ile | Leu | Asp | Ser | Gln | Thr | Val | Val | Leu | Lys | Glu | Pro | Gln | Cys |
|---|---|---|---|---|---|---|---|---|---|---|---|---|---|---|---|
| | | | | 85 | | | | | 90 | | | | | 95 | |

```
Ile Leu Gly Arg Leu Ser Glu Lys Ser Ser Gly Gln Met Ala Gln Lys
                100                 105                 110

Phe Ser Phe Ser Lys Val Phe Gly Pro Ala Thr Thr Gln Lys Glu Phe
            115                 120                 125

Phe Gln Gly Cys Ile Met Gln Pro Val Lys Asp Leu Leu Lys Gly Gln
        130                 135                 140

Ser Arg Leu Ile Phe Thr Tyr Gly Leu Thr Asn Ser Gly Lys Thr Tyr
145                 150                 155                 160

Thr Phe Gln Gly Thr Glu Glu Asn Ile Gly Ile Leu Pro Arg Thr Leu
                165                 170                 175

Asn Val Leu Phe Asp Ser Leu Gln Glu Arg Leu Tyr Thr Lys Met Asn
            180                 185                 190

Leu Lys Pro His Arg Ser Arg Glu Tyr Leu Arg Leu Ser Ser Glu Gln
        195                 200                 205

Glu Lys Glu Glu Ile Ala Ser Lys Ser Ala Leu Leu Arg Gln Ile Lys
210                 215                 220

Glu Val Thr Val His Asn Asp Ser Asp Thr Leu Tyr Gly Ser Leu
225                 230                 235                 240

Thr Asn Ser Leu Asn Ile Ser Glu Phe Glu Glu Ser Ile Lys Asp Tyr
            245                 250                 255

Glu Gln Ala Asn Leu Asn Met Ala Asn Ser Ile Lys Phe Ser Val Trp
        260                 265                 270

Val Ser Phe Phe Glu Ile Tyr Asn Glu Tyr Ile Tyr Asp Leu Phe Val
            275                 280                 285

Pro Val Ser Ser Lys Phe Gln Lys Arg Lys Met Leu Arg Leu Ser Gln
290                 295                 300

Asp Val Lys Gly Tyr Ser Phe Ile Lys Asp Leu Gln Trp Ile Gln Val
305                 310                 315                 320

Ser Asp Ser Lys Glu Ala Tyr Arg Leu Leu Lys Leu Gly Ile Lys His
                325                 330                 335

Gln Ser Val Ala Phe Thr Lys Leu Asn Asn Ala Ser Ser Arg Ser His
            340                 345                 350

Ser Ile Phe Thr Val Lys Ile Leu Gln Ile Glu Asp Ser Glu Met Ser
        355                 360                 365

Arg Val Ile Arg Val Ser Glu Leu Ser Leu Cys Asp Leu Ala Gly Ser
370                 375                 380

Glu Arg Thr Met Lys Thr Gln Asn Glu Gly Glu Arg Leu Arg Glu Thr
385                 390                 395                 400

Gly Asn Ile Asn Thr Ser Leu Leu Thr Leu Gly Lys Cys Ile Asn Val
                405                 410                 415

Leu Lys Asn Ser Glu Lys Ser Lys Phe Gln Gln His Val Pro Phe Arg
            420                 425                 430

Glu Ser Lys Leu Thr His Tyr Phe Gln Ser Phe Phe Asn Gly Lys Gly
        435                 440                 445

Lys Ile Cys Met Ile Val Asn Ile Ser Gln Cys Tyr Leu Ala Tyr Asp
        450                 455                 460

Glu Thr Leu Asn Val Leu Lys Phe Ser Ala Ile Ala Gln Lys Val Cys
465                 470                 475                 480

Val Pro Asp Thr Leu Asn Ser Ser Gln Glu Lys Leu Phe Gly Pro Val
                485                 490                 495

Lys Ser Ser Gln Asp Val Ser Leu Asp Ser Asn Ser Asn Ser Lys Ile
            500                 505                 510

Leu Asn Val Lys Arg Ala Thr Ile Ser Trp Glu Asn Ser Leu Glu Asp
```

```
                515                 520                 525
Leu Met Glu Asp Glu Asp Leu Val Glu Glu Leu Glu Asn Ala Glu Glu
    530                 535                 540

Thr Gln Asn Val Glu Thr Lys Leu Leu Asp Glu Asp Leu Asp Lys Thr
545                 550                 555                 560

Leu Glu Glu Asn Lys Ala Phe Ile Ser His Glu Glu Lys Arg Lys Leu
                565                 570                 575

Leu Asp Leu Ile Glu Asp Leu Lys Lys Lys Leu Ile Asn Glu Lys Lys
            580                 585                 590

Glu Lys Leu Thr Leu Glu Phe Lys Ile Arg Glu Glu Val Thr Gln Glu
        595                 600                 605

Phe Thr Gln Tyr Trp Ala Gln Arg Glu Ala Asp Phe Lys Glu Thr Leu
    610                 615                 620

Leu Gln Glu Arg Glu Ile Leu Glu Glu Asn Ala Glu Arg Arg Leu Ala
625                 630                 635                 640

Ile Phe Lys Asp Leu Val Gly Lys Cys Asp Thr Arg Glu Glu Ala Ala
                645                 650                 655

Lys Asp Ile Cys Ala Thr Lys Val Glu Thr Glu Glu Ala Thr Ala Cys
            660                 665                 670

Leu Glu Leu Lys Phe Asn Gln Ile Lys Ala Glu Leu Ala Lys Thr Lys
        675                 680                 685

Gly Glu Leu Ile Lys Thr Lys Glu Glu Leu Lys Lys Arg Glu Asn Glu
    690                 695                 700

Ser Asp Ser Leu Ile Gln Glu Leu Glu Thr Ser Asn Lys Lys Ile Ile
705                 710                 715                 720

Thr Gln Asn Gln Arg Ile Lys Glu Leu Ile Asn Ile Asp Gln Lys
                725                 730                 735

Glu Asp Thr Ile Asn Glu Phe Gln Asn Leu Lys Ser His Met Glu Asn
            740                 745                 750

Thr Phe Lys Cys Asn Asp Lys Ala Asp Thr Ser Ser Leu Ile Ile Asn
        755                 760                 765

Asn Lys Leu Ile Cys Asn Glu Thr Val Glu Val Pro Lys Asp Ser Lys
    770                 775                 780

Ser Lys Ile Cys Ser Glu Arg Lys Arg Val Asn Glu Asn Glu Leu Gln
785                 790                 795                 800

Gln Asp Glu Pro Pro Ala Lys Lys Gly Ser Ile His Val Ser Ser Ala
                805                 810                 815

Ile Thr Glu Asp Gln Lys Lys Ser Glu Glu Val Arg Pro Asn Ile Ala
            820                 825                 830

Glu Ile Glu Asp Ile Arg Val Leu Gln Glu Asn Asn Glu Gly Leu Arg
        835                 840                 845

Ala Phe Leu Leu Thr Ile Glu Asn Glu Leu Lys Asn Glu Lys Glu Glu
    850                 855                 860

Lys Ala Glu Leu Asn Lys Gln Ile Val His Phe Gln Gln Glu Leu Ser
865                 870                 875                 880

Leu Ser Glu Lys Lys Asn Leu Thr Leu Ser Lys Glu Val Gln Gln Ile
                885                 890                 895

Gln Ser Asn Tyr Asp Ile Ala Ile Ala Glu Leu His Val Gln Lys Ser
            900                 905                 910

Lys Asn Gln Glu Gln Glu Glu Lys Ile Met Lys Leu Ser Asn Glu Ile
        915                 920                 925

Glu Thr Ala Thr Arg Ser Ile Thr Asn Asn Val Ser Gln Ile Lys Leu
    930                 935                 940
```

-continued

```
Met His Thr Lys Ile Asp Glu Leu Arg Thr Leu Asp Ser Val Ser Gln
945                 950                 955                 960

Ile Ser Asn Ile Asp Leu Leu Asn Leu Arg Asp Leu Ser Asn Gly Ser
                965                 970                 975

Glu Glu Asp Asn Leu Pro Asn Thr Gln Leu Asp Leu Leu Gly Asn Asp
            980                 985                 990

Tyr Leu Val Ser Lys Gln Val Lys Glu Tyr Arg Ile Gln Glu Pro Asn
        995                 1000                1005

Arg Glu Asn Ser Phe His Ser Ser Ile Glu Ala Ile Trp Glu Glu
    1010                1015                1020

Cys Lys Glu Ile Val Lys Ala Ser Ser Lys Ser His Gln Ile
    1025                1030                1035

Glu Glu Leu Glu Gln Gln Ile Glu Lys Leu Gln Ala Glu Val Lys
    1040                1045                1050

Gly Tyr Lys Asp Glu Asn Asn Arg Leu Lys Glu Lys Glu His Lys
    1055                1060                1065

Asn Gln Asp Asp Leu Leu Lys Glu Lys Glu Thr Leu Ile Gln Gln
    1070                1075                1080

Leu Lys Glu Glu Leu Gln Glu Lys Asn Val Thr Leu Asp Val Gln
    1085                1090                1095

Ile Gln His Val Val Glu Gly Lys Arg Ala Leu Ser Glu Leu Thr
    1100                1105                1110

Gln Gly Val Thr Cys Tyr Lys Ala Lys Ile Lys Glu Leu Glu Thr
    1115                1120                1125

Ile Leu Glu Thr Gln Lys Val Glu Cys Ser His Ser Ala Lys Leu
    1130                1135                1140

Glu Gln Asp Ile Leu Glu Lys Glu Ser Ile Ile Leu Lys Leu Glu
    1145                1150                1155

Arg Asn Leu Lys Glu Phe Gln Glu His Leu Gln Asp Ser Val Lys
    1160                1165                1170

Asn Thr Lys Asp Leu Asn Val Lys Glu Leu Lys Leu Lys Glu Glu
    1175                1180                1185

Ile Thr Gln Leu Thr Asn Asn Leu Gln Asp Met Lys His Leu Leu
    1190                1195                1200

Gln Leu Lys Glu Glu Glu Glu Thr Asn Arg Gln Glu Thr Glu
    1205                1210                1215

Lys Leu Lys Glu Glu Leu Ser Ala Ser Ser Ala Arg Thr Gln Asn
    1220                1225                1230

Leu Lys Ala Asp Leu Gln Arg Lys Glu Glu Asp Tyr Ala Asp Leu
    1235                1240                1245

Lys Glu Lys Leu Thr Asp Ala Lys Lys Gln Ile Lys Gln Val Gln
    1250                1255                1260

Lys Glu Val Ser Val Met Arg Asp Glu Asp Lys Leu Leu Arg Ile
    1265                1270                1275

Lys Ile Asn Glu Leu Glu Lys Lys Lys Asn Gln Cys Ser Gln Glu
    1280                1285                1290

Leu Asp Met Lys Gln Arg Thr Ile Gln Gln Leu Lys Glu Gln Leu
    1295                1300                1305

Asn Asn Gln Lys Val Glu Glu Ala Ile Gln Gln Tyr Glu Arg Ala
    1310                1315                1320

Cys Lys Asp Leu Asn Val Lys Glu Lys Ile Ile Glu Asp Met Arg
    1325                1330                1335
```

-continued

```
Met Thr Leu Glu Glu Gln Glu Gln Thr Gln Val Glu Gln Asp Gln
    1340                1345                1350

Val Leu Glu Ala Lys Leu Glu Glu Val Glu Arg Leu Ala Thr Glu
    1355                1360                1365

Leu Glu Lys Trp Lys Glu Lys Cys Asn Asp Leu Glu Thr Lys Asn
    1370                1375                1380

Asn Gln Arg Ser Asn Lys Glu His Glu Asn Asn Thr Asp Val Leu
    1385                1390                1395

Gly Lys Leu Thr Asn Leu Gln Asp Glu Leu Gln Glu Ser Glu Gln
    1400                1405                1410

Lys Tyr Asn Ala Asp Arg Lys Lys Trp Leu Glu Glu Lys Met Met
    1415                1420                1425

Leu Ile Thr Gln Ala Lys Glu Ala Glu Asn Ile Arg Asn Lys Glu
    1430                1435                1440

Met Lys Lys Tyr Ala Glu Asp Arg Glu Arg Phe Phe Lys Gln Gln
    1445                1450                1455

Asn Glu Met Glu Ile Leu Thr Ala Gln Leu Thr Glu Lys Asp Ser
    1460                1465                1470

Asp Leu Gln Lys Trp Arg Glu Glu Arg Asp Gln Leu Val Ala Ala
    1475                1480                1485

Leu Glu Ile Gln Leu Lys Ala Leu Ile Ser Ser Asn Val Gln Lys
    1490                1495                1500

Asp Asn Glu Ile Glu Gln Leu Lys Arg Ile Ile Ser Glu Thr Ser
    1505                1510                1515

Lys Ile Glu Thr Gln Ile Met Asp Ile Lys Pro Lys Arg Ile Ser
    1520                1525                1530

Ser Ala Asp Pro Asp Lys Leu Gln Thr Glu Pro Leu Ser Thr Ser
    1535                1540                1545

Phe Glu Ile Ser Arg Asn Lys Ile Glu Asp Gly Ser Val Val Leu
    1550                1555                1560

Asp Ser Cys Glu Val Ser Thr Glu Asn Asp Gln Ser Thr Arg Phe
    1565                1570                1575

Pro Lys Pro Glu Leu Glu Ile Gln Phe Thr Pro Leu Gln Pro Asn
    1580                1585                1590

Lys Met Ala Val Lys His Pro Gly Cys Thr Thr Pro Val Thr Val
    1595                1600                1605

Lys Ile Pro Lys Ala Arg Lys Arg Lys Ser Asn Glu Met Glu Glu
    1610                1615                1620

Asp Leu Val Lys Cys Glu Asn Lys Lys Asn Ala Thr Pro Arg Thr
    1625                1630                1635

Asn Leu Lys Phe Pro Ile Ser Asp Asp Arg Asn Ser Ser Val Lys
    1640                1645                1650

Lys Glu Gln Lys Val Ala Ile Arg Pro Ser Ser Lys Lys Thr Tyr
    1655                1660                1665

Ser Leu Arg Ser Gln Ala Ser Ile Ile Gly Val Asn Leu Ala Thr
    1670                1675                1680

Lys Lys Lys Glu Gly Thr Leu Gln Lys Phe Gly Asp Phe Leu Gln
    1685                1690                1695

His Ser Pro Ser Ile Leu Gln Ser Lys Ala Lys Lys Ile Ile Glu
    1700                1705                1710

Thr Met Ser Ser Ser Lys Leu Ser Asn Val Glu Ala Ser Lys Glu
    1715                1720                1725

Asn Val Ser Gln Pro Lys Arg Ala Lys Arg Lys Leu Tyr Thr Ser
```

```
                   1730                1735                1740
Glu Ile  Ser Ser Pro Ile  Asp Ile Ser Gly Gln Val  Ile Leu Met
         1745                1750                1755

Asp Gln  Lys Met Lys Glu  Ser Asp His Gln Ile  Ile Lys Arg Arg
    1760                1765                1770

Leu Arg  Thr Lys Thr Ala  Lys
    1775                1780

<210> SEQ ID NO 187
<211> LENGTH: 6459
<212> TYPE: DNA
<213> ORGANISM: Homo sapiens
<220> FEATURE:
<221> NAME/KEY: CDS
<222> LOCATION: (93)..(5555)

<400> SEQUENCE: 187
agtgcggtgc cctggccgcc attgtttgaa tttgaaaacg gtaacatcgc agtgctgctc         60
gcgggtctgg ctagtcaggc gaagtttgca ga atg gaa tct aat ttt aat caa         113
                                   Met Glu Ser Asn Phe Asn Gln
                                   1               5 gag gga gta cct cga cca tct tat gtt ttt agt gct gac cca att gca         161
Glu Gly Val Pro Arg Pro Ser Tyr Val Phe Ser Ala Asp Pro Ile Ala
        10                  15                  20 agg cct tca gaa ata aat ttc gat ggc att aag ctt gat ctg tct cat         209
Arg Pro Ser Glu Ile Asn Phe Asp Gly Ile Lys Leu Asp Leu Ser His
    25                  30                  35 gaa ttt tcc tta gtt gct cca aat act gag gca aac agt ttc gaa tct         257
Glu Phe Ser Leu Val Ala Pro Asn Thr Glu Ala Asn Ser Phe Glu Ser
40                  45                  50                  55 aaa gat tat ctc cag gtt tgt ctt cga ata aga cca ttt aca cag tca         305
Lys Asp Tyr Leu Gln Val Cys Leu Arg Ile Arg Pro Phe Thr Gln Ser
                60                  65                  70 gaa aaa gaa ctt gag tct gag ggc tgt gtg cat att ctg gat tca cag         353
Glu Lys Glu Leu Glu Ser Glu Gly Cys Val His Ile Leu Asp Ser Gln
            75                  80                  85 act gtt gtg ctg aaa gag cct caa tgc atc ctt ggt cgg tta agt gaa         401
Thr Val Val Leu Lys Glu Pro Gln Cys Ile Leu Gly Arg Leu Ser Glu
        90                  95                 100 aaa agc tca ggg cag atg gca cag aaa ttc agt ttt tcc aag gtt ttt         449
Lys Ser Ser Gly Gln Met Ala Gln Lys Phe Ser Phe Ser Lys Val Phe
    105                 110                 115 ggc cca gca act aca cag aag gaa ttc ttt cag ggt tgc att atg caa         497
Gly Pro Ala Thr Thr Gln Lys Glu Phe Phe Gln Gly Cys Ile Met Gln
120                 125                 130                 135 cca gta aaa gac ctc ttg aaa gga cag agt cgt ctg att ttt act tac         545
Pro Val Lys Asp Leu Leu Lys Gly Gln Ser Arg Leu Ile Phe Thr Tyr
                140                 145                 150 ggg cta acc aat tca gga aaa aca tat aca ttt caa ggg aca gaa gaa         593
Gly Leu Thr Asn Ser Gly Lys Thr Tyr Thr Phe Gln Gly Thr Glu Glu
            155                 160                 165 aat att ggc att ctg cct cga act ttg aat gta tta ttt gat agt ctt         641
Asn Ile Gly Ile Leu Pro Arg Thr Leu Asn Val Leu Phe Asp Ser Leu
        170                 175                 180 caa gaa aga ctg tat aca aag atg aac ctt aaa cca cat aga tcc aga         689
Gln Glu Arg Leu Tyr Thr Lys Met Asn Leu Lys Pro His Arg Ser Arg
    185                 190                 195 gaa tac tta agg tta tca tca gaa caa gag aaa gaa gaa att gct agc         737
Glu Tyr Leu Arg Leu Ser Ser Glu Gln Glu Lys Glu Glu Ile Ala Ser
200                 205                 210                 215
```

```
aaa agt gca ttg ctt cgg caa att aaa gag gtt act gtg cat aat gat        785
Lys Ser Ala Leu Leu Arg Gln Ile Lys Glu Val Thr Val His Asn Asp
            220                 225                 230 agt gat gat act ctt tat gga agt tta act aac tct ttg aat atc tca        833
Ser Asp Asp Thr Leu Tyr Gly Ser Leu Thr Asn Ser Leu Asn Ile Ser
        235                 240                 245 gag ttt gaa gaa tcc ata aaa gat tat gaa caa gcc aac ttg aat atg        881
Glu Phe Glu Glu Ser Ile Lys Asp Tyr Glu Gln Ala Asn Leu Asn Met
    250                 255                 260 gct aat agt ata aaa ttt tct gtg tgg gtt tct ttc ttt gaa att tac        929
Ala Asn Ser Ile Lys Phe Ser Val Trp Val Ser Phe Phe Glu Ile Tyr
265                 270                 275 aat gaa tat att tat gac tta ttt gtt cct gta tca tct aaa ttc caa        977
Asn Glu Tyr Ile Tyr Asp Leu Phe Val Pro Val Ser Ser Lys Phe Gln
280                 285                 290                 295 aag aga aag atg ctg cgc ctt tcc caa gac gta aag ggc tat tct ttt       1025
Lys Arg Lys Met Leu Arg Leu Ser Gln Asp Val Lys Gly Tyr Ser Phe
                300                 305                 310 ata aaa gat cta caa tgg att caa gta tct gat tcc aaa gaa gcc tat       1073
Ile Lys Asp Leu Gln Trp Ile Gln Val Ser Asp Ser Lys Glu Ala Tyr
            315                 320                 325 aga ctt tta aaa cta gga ata aag cac cag agt gtt gcc ttc aca aaa       1121
Arg Leu Leu Lys Leu Gly Ile Lys His Gln Ser Val Ala Phe Thr Lys
        330                 335                 340 ttg aat aat gct tcc agt aga agt cac agc ata ttc act gtt aaa ata       1169
Leu Asn Asn Ala Ser Ser Arg Ser His Ser Ile Phe Thr Val Lys Ile
    345                 350                 355 tta cag att gaa gat tct gaa atg tct cgt gta att cga gtc agt gaa       1217
Leu Gln Ile Glu Asp Ser Glu Met Ser Arg Val Ile Arg Val Ser Glu
360                 365                 370                 375 tta tct tta tgt gat ctt gct ggt tca gaa cga act atg aag aca cag       1265
Leu Ser Leu Cys Asp Leu Ala Gly Ser Glu Arg Thr Met Lys Thr Gln
                380                 385                 390 aat gaa ggt gaa agg tta aga gag act ggg aat atc aac act tct tta       1313
Asn Glu Gly Glu Arg Leu Arg Glu Thr Gly Asn Ile Asn Thr Ser Leu
            395                 400                 405 ttg act ctg gga aag tgt att aac gtc ttg aag aat agt gaa aag tca       1361
Leu Thr Leu Gly Lys Cys Ile Asn Val Leu Lys Asn Ser Glu Lys Ser
        410                 415                 420 aag ttt caa cag cat gtg cct ttc cgg gaa agt aaa ctg act cac tat       1409
Lys Phe Gln Gln His Val Pro Phe Arg Glu Ser Lys Leu Thr His Tyr
    425                 430                 435 ttt caa agt ttt ttt aat ggt aaa ggg aaa att tgt atg att gtc aat       1457
Phe Gln Ser Phe Phe Asn Gly Lys Gly Lys Ile Cys Met Ile Val Asn
440                 445                 450                 455 atc agc caa tgt tat tta gcc tat gat gaa aca ctc aat gta ttg aag       1505
Ile Ser Gln Cys Tyr Leu Ala Tyr Asp Glu Thr Leu Asn Val Leu Lys
                460                 465                 470 ttc tcc gcc att gca caa aaa gtt tgt gtc cca gac act tta aat tcc       1553
Phe Ser Ala Ile Ala Gln Lys Val Cys Val Pro Asp Thr Leu Asn Ser
            475                 480                 485 tct caa gag aaa tta ttt gga cct gtc aaa tct tct caa gat gta tca       1601
Ser Gln Glu Lys Leu Phe Gly Pro Val Lys Ser Ser Gln Asp Val Ser
        490                 495                 500 cta gac agt aat tca aac agt aaa ata tta aat gta aaa aga gcc acc       1649
Leu Asp Ser Asn Ser Asn Ser Lys Ile Leu Asn Val Lys Arg Ala Thr
    505                 510                 515 att tca tgg gaa aat agt cta gaa gat ttg atg gaa gac gag gat ttg       1697
Ile Ser Trp Glu Asn Ser Leu Glu Asp Leu Met Glu Asp Glu Asp Leu
```

```
                  520                 525                 530                 535
gtt gag gag cta gaa aac gct gaa gaa act caa aat gtg gaa act aaa              1745
Val Glu Glu Leu Glu Asn Ala Glu Glu Thr Gln Asn Val Glu Thr Lys
                540                 545                 550 ctt ctt gat gaa gat cta gat aaa aca tta gag gaa aat aag gct ttc              1793
Leu Leu Asp Glu Asp Leu Asp Lys Thr Leu Glu Glu Asn Lys Ala Phe
                555                 560                 565 att agc cac gag gag aaa aga aaa ctg ttg gac tta ata gaa gac ttg              1841
Ile Ser His Glu Glu Lys Arg Lys Leu Leu Asp Leu Ile Glu Asp Leu
                570                 575                 580 aaa aaa aaa ctg ata aat gaa aaa aag gaa aaa tta acc ttg gaa ttt              1889
Lys Lys Lys Leu Ile Asn Glu Lys Lys Glu Lys Leu Thr Leu Glu Phe
                585                 590                 595 aaa att cga gaa gaa gtt aca cag gag ttt act cag tat tgg gct caa              1937
Lys Ile Arg Glu Glu Val Thr Gln Glu Phe Thr Gln Tyr Trp Ala Gln
600                 605                 610                 615 cgg gaa gct gac ttt aag gag act ctg ctt caa gaa cga gag ata tta              1985
Arg Glu Ala Asp Phe Lys Glu Thr Leu Leu Gln Glu Arg Glu Ile Leu
                620                 625                 630 gaa gaa aat gct gaa cgt cgt ttg gct atc ttc aag gat ttg gtt ggt              2033
Glu Glu Asn Ala Glu Arg Arg Leu Ala Ile Phe Lys Asp Leu Val Gly
                635                 640                 645 aaa tgt gac act cga gaa gaa gca gcg aaa gac att tgt gcc aca aaa              2081
Lys Cys Asp Thr Arg Glu Glu Ala Ala Lys Asp Ile Cys Ala Thr Lys
                650                 655                 660 gtt gaa act gaa gaa aca cat aat tat gta gga ttt gaa gat att att              2129
Val Glu Thr Glu Glu Thr His Asn Tyr Val Gly Phe Glu Asp Ile Ile
                665                 670                 675 gat tct ctt caa gat aat gtt gct gat att aag aaa cag gct gaa att              2177
Asp Ser Leu Gln Asp Asn Val Ala Asp Ile Lys Lys Gln Ala Glu Ile
680                 685                 690                 695 gct cac tta tat att gca tct ctt cct gac ccc cag gaa gct act gct              2225
Ala His Leu Tyr Ile Ala Ser Leu Pro Asp Pro Gln Glu Ala Thr Ala
                700                 705                 710 tgt tta gaa cta aag ttt aat caa att aaa gct gaa tta gct aaa acc              2273
Cys Leu Glu Leu Lys Phe Asn Gln Ile Lys Ala Glu Leu Ala Lys Thr
                715                 720                 725 aaa gga gaa tta atc aaa acc aaa gaa gag tta aaa aag aga gaa aat              2321
Lys Gly Glu Leu Ile Lys Thr Lys Glu Glu Leu Lys Lys Arg Glu Asn
                730                 735                 740 gaa tca gat tca ttg att caa gag ctt gag aca tct aat aag aaa ata              2369
Glu Ser Asp Ser Leu Ile Gln Glu Leu Glu Thr Ser Asn Lys Lys Ile
745                 750                 755 att aca cag aat caa aga att aaa gaa ttg ata aat ata att gat caa              2417
Ile Thr Gln Asn Gln Arg Ile Lys Glu Leu Ile Asn Ile Ile Asp Gln
760                 765                 770                 775 aaa gaa gat act atc aac gaa ttt cag aac cta aag tct cat atg gaa              2465
Lys Glu Asp Thr Ile Asn Glu Phe Gln Asn Leu Lys Ser His Met Glu
                780                 785                 790 aac aca ttt aaa tgc aat gac aag gct gat aca tct tct tta ata ata              2513
Asn Thr Phe Lys Cys Asn Asp Lys Ala Asp Thr Ser Ser Leu Ile Ile
                795                 800                 805 aac aat aaa ttg att tgt aat gaa aca gtt gaa gta cct aag gac agc              2561
Asn Asn Lys Leu Ile Cys Asn Glu Thr Val Glu Val Pro Lys Asp Ser
                810                 815                 820 aaa tct aaa atc tgt tca gaa aga aaa aga gta aat gaa aat gaa ctt              2609
Lys Ser Lys Ile Cys Ser Glu Arg Lys Arg Val Asn Glu Asn Glu Leu
825                 830                 835 cag caa gat gaa cca cca gca aag aaa ggg tct atc cat gtt agt tca              2657
```

| | | | | | | | | | | | | | |
|---|---|---|---|---|---|---|---|---|---|---|---|---|---|
| Gln | Gln | Asp | Glu | Pro | Pro | Ala | Lys | Lys | Gly | Ser | Ile | His | Val | Ser | Ser |
| 840 | | | | | 845 | | | | 850 | | | | 855 |

```
gct atc act gaa gac caa aag aaa agt gaa gaa gtg cga ccg aac att     2705
Ala Ile Thr Glu Asp Gln Lys Lys Ser Glu Glu Val Arg Pro Asn Ile
                860                 865                 870 gca gaa att gaa gac atc aga gtt tta caa gaa aat aat gaa gga ctg     2753
Ala Glu Ile Glu Asp Ile Arg Val Leu Gln Glu Asn Asn Glu Gly Leu
            875                 880                 885 aga gca ttt tta ctc act att gag aat gaa ctt aaa aat gaa aag gaa     2801
Arg Ala Phe Leu Leu Thr Ile Glu Asn Glu Leu Lys Asn Glu Lys Glu
        890                 895                 900 gaa aaa gca gaa tta aat aaa cag att gtt cat ttt cag cag gaa ctt     2849
Glu Lys Ala Glu Leu Asn Lys Gln Ile Val His Phe Gln Gln Glu Leu
    905                 910                 915 tct ctt tct gaa aaa aag aat tta act tta agt aaa gag gtc caa caa     2897
Ser Leu Ser Glu Lys Lys Asn Leu Thr Leu Ser Lys Glu Val Gln Gln
920                 925                 930                 935 att cag tca aat tat gat att gca att gct gaa tta cat gtg cag aaa     2945
Ile Gln Ser Asn Tyr Asp Ile Ala Ile Ala Glu Leu His Val Gln Lys
                940                 945                 950 agt aaa aat caa gaa cag gag gaa aag atc atg aaa ttg tca aat gag     2993
Ser Lys Asn Gln Glu Gln Glu Glu Lys Ile Met Lys Leu Ser Asn Glu
            955                 960                 965 ata gaa act gct aca aga agc att aca aat aat gtt tca caa ata aaa     3041
Ile Glu Thr Ala Thr Arg Ser Ile Thr Asn Asn Val Ser Gln Ile Lys
        970                 975                 980 tta atg cac acg aaa ata gac gaa cta cgt act ctt gat tca gtt tct     3089
Leu Met His Thr Lys Ile Asp Glu Leu Arg Thr Leu Asp Ser Val Ser
    985                 990                 995 cag att tca aac ata gat ttg ctc aat ctc agg gat ctg tca aat         3134
Gln Ile Ser Asn Ile Asp Leu Leu Asn Leu Arg Asp Leu Ser Asn
1000                1005                1010 ggt tct gag gag gat aat ttg cca aat aca cag tta gac ctt tta         3179
Gly Ser Glu Glu Asp Asn Leu Pro Asn Thr Gln Leu Asp Leu Leu
1015                1020                1025 ggt aat gat tat ttg gta agt aag caa gtt aaa gaa tat cga att         3224
Gly Asn Asp Tyr Leu Val Ser Lys Gln Val Lys Glu Tyr Arg Ile
1030                1035                1040 caa gaa ccc aat agg gaa aat tct ttc cac tct agt att gaa gct         3269
Gln Glu Pro Asn Arg Glu Asn Ser Phe His Ser Ser Ile Glu Ala
1045                1050                1055 att tgg gaa gaa tgt aaa gag att gtg aag gcc tct tcc aaa aaa         3314
Ile Trp Glu Glu Cys Lys Glu Ile Val Lys Ala Ser Ser Lys Lys
1060                1065                1070 agt cat cag att gag gaa ctg gaa caa caa att gaa aaa ttg cag         3359
Ser His Gln Ile Glu Glu Leu Glu Gln Gln Ile Glu Lys Leu Gln
1075                1080                1085 gca gaa gta aaa ggc tat aag gat gaa aac aat aga cta aag gag         3404
Ala Glu Val Lys Gly Tyr Lys Asp Glu Asn Asn Arg Leu Lys Glu
1090                1095                1100 aag gag cat aaa aac caa gat gac cta cta aaa gaa aaa gaa act         3449
Lys Glu His Lys Asn Gln Asp Asp Leu Leu Lys Glu Lys Glu Thr
1105                1110                1115 ctt ata cag cag ctg aaa gaa gaa ttg caa gaa aaa aat gtt act         3494
Leu Ile Gln Gln Leu Lys Glu Glu Leu Gln Glu Lys Asn Val Thr
1120                1125                1130 ctt gat gtt caa ata cag cat gta gtt gaa gga aag aga gcg ctt         3539
Leu Asp Val Gln Ile Gln His Val Val Glu Gly Lys Arg Ala Leu
1135                1140                1145
```

```
tca gaa ctt aca caa ggt gtt act tgc tat aag gca aaa ata aag    3584
Ser Glu Leu Thr Gln Gly Val Thr Cys Tyr Lys Ala Lys Ile Lys
1150                1155                1160 gaa ctt gaa aca att tta gag act cag aaa gtt gaa tgt agt cat    3629
Glu Leu Glu Thr Ile Leu Glu Thr Gln Lys Val Glu Cys Ser His
1165                1170                1175 tca gcc aag tta gaa caa gac att ttg gaa aag gaa tct atc atc    3674
Ser Ala Lys Leu Glu Gln Asp Ile Leu Glu Lys Glu Ser Ile Ile
1180                1185                1190 tta aag cta gaa aga aat ttg aag gaa ttt caa gaa cat ctt cag    3719
Leu Lys Leu Glu Arg Asn Leu Lys Glu Phe Gln Glu His Leu Gln
1195                1200                1205 gat tct gtc aaa aac acc aaa gat tta aat gta aag gaa ctc aag    3764
Asp Ser Val Lys Asn Thr Lys Asp Leu Asn Val Lys Glu Leu Lys
1210                1215                1220 ctg aaa gaa gaa atc aca cag tta aca aat aat ttg caa gat atg    3809
Leu Lys Glu Glu Ile Thr Gln Leu Thr Asn Asn Leu Gln Asp Met
1225                1230                1235 aaa cat tta ctt caa tta aaa gaa gaa gaa gaa gaa acc aac agg    3854
Lys His Leu Leu Gln Leu Lys Glu Glu Glu Glu Thr Asn Arg
1240                1245                1250 caa gaa aca gaa aaa ttg aaa gag gaa ctc tct gca agc tct gct    3899
Gln Glu Thr Glu Lys Leu Lys Glu Glu Leu Ser Ala Ser Ser Ala
1255                1260                1265 cgt acc cag aat ctg aaa gca gat ctt cag agg aag gaa gaa gat    3944
Arg Thr Gln Asn Leu Lys Ala Asp Leu Gln Arg Lys Glu Glu Asp
1270                1275                1280 tat gct gac ctg aaa gag aaa ctg act gat gcc aaa aag cag att    3989
Tyr Ala Asp Leu Lys Glu Lys Leu Thr Asp Ala Lys Lys Gln Ile
1285                1290                1295 aag caa gta cag aaa gag gta tct gta atg cgt gat gag gat aaa    4034
Lys Gln Val Gln Lys Glu Val Ser Val Met Arg Asp Glu Asp Lys
1300                1305                1310 tta ctg agg att aaa att aat gaa ctg gag aaa aag aaa aac cag    4079
Leu Leu Arg Ile Lys Ile Asn Glu Leu Glu Lys Lys Lys Asn Gln
1315                1320                1325 tgt tct cag gaa tta gat atg aaa cag cga acc att cag caa ctc    4124
Cys Ser Gln Glu Leu Asp Met Lys Gln Arg Thr Ile Gln Gln Leu
1330                1335                1340 aag gag cag tta aat aat cag aaa gtg gaa gaa gct ata caa cag    4169
Lys Glu Gln Leu Asn Asn Gln Lys Val Glu Glu Ala Ile Gln Gln
1345                1350                1355 tat gag aga gca tgc aaa gat cta aat gtt aaa gag aaa ata att    4214
Tyr Glu Arg Ala Cys Lys Asp Leu Asn Val Lys Glu Lys Ile Ile
1360                1365                1370 gaa gac atg cga atg aca cta gaa gaa cag gaa caa act cag gta    4259
Glu Asp Met Arg Met Thr Leu Glu Glu Gln Glu Gln Thr Gln Val
1375                1380                1385 gaa cag gat caa gtg ctt gag gct aaa tta gag gaa gtt gaa agg    4304
Glu Gln Asp Gln Val Leu Glu Ala Lys Leu Glu Glu Val Glu Arg
1390                1395                1400 ctg gcc aca gaa ttg gaa aaa tgg aag gaa aaa tgc aat gat ttg    4349
Leu Ala Thr Glu Leu Glu Lys Trp Lys Glu Lys Cys Asn Asp Leu
1405                1410                1415 gaa acc aaa aac aat caa agg tca aat aaa gaa cat gag aac aac    4394
Glu Thr Lys Asn Asn Gln Arg Ser Asn Lys Glu His Glu Asn Asn
1420                1425                1430 aca gat gtg ctt gga aag ctc act aat ctt caa gat gag tta cag    4439
Thr Asp Val Leu Gly Lys Leu Thr Asn Leu Gln Asp Glu Leu Gln
1435                1440                1445
```

-continued

| | | | | | | | | | | | |
|---|---|---|---|---|---|---|---|---|---|---|---|
| gag | tct | gaa | cag | aaa | tat | aat | gct | gat | aga | aag | |
| Glu | Ser | Glu | Gln | Lys | Tyr | Asn | Ala | Asp | Arg | Lys | |
| 1450 | | | | 1455 | | | | 1460 | | | |

```
gag  tct  gaa  cag  aaa  tat  aat  gct  gat  aga  aag  aaa  tgg  tta  gaa         4484
Glu  Ser  Glu  Gln  Lys  Tyr  Asn  Ala  Asp  Arg  Lys  Lys  Trp  Leu  Glu
1450                1455                1460 gaa  aaa  atg  atg  ctt  atc  act  caa  gcg  aaa  gaa  gca  gag  aat  ata         4529
Glu  Lys  Met  Met  Leu  Ile  Thr  Gln  Ala  Lys  Glu  Ala  Glu  Asn  Ile
     1465                1470                1475 cga  aat  aaa  gag  atg  aaa  aaa  tat  gct  gag  gac  agg  gag  cgt  ttt         4574
Arg  Asn  Lys  Glu  Met  Lys  Lys  Tyr  Ala  Glu  Asp  Arg  Glu  Arg  Phe
1480                1485                1490 ttt  aag  caa  cag  aat  gaa  atg  gaa  ata  ctg  aca  gcc  cag  ctg  aca         4619
Phe  Lys  Gln  Gln  Asn  Glu  Met  Glu  Ile  Leu  Thr  Ala  Gln  Leu  Thr
     1495                1500                1505 gag  aaa  gat  agt  gac  ctt  caa  aag  tgg  cga  gaa  gaa  cga  gat  caa         4664
Glu  Lys  Asp  Ser  Asp  Leu  Gln  Lys  Trp  Arg  Glu  Glu  Arg  Asp  Gln
1510                1515                1520 ctg  gtt  gca  gct  tta  gaa  ata  cag  cta  aaa  gca  ctg  ata  tcc  agt         4709
Leu  Val  Ala  Ala  Leu  Glu  Ile  Gln  Leu  Lys  Ala  Leu  Ile  Ser  Ser
     1525                1530                1535 aat  gta  cag  aaa  gat  aat  gaa  att  gaa  caa  cta  aaa  agg  atc  ata         4754
Asn  Val  Gln  Lys  Asp  Asn  Glu  Ile  Glu  Gln  Leu  Lys  Arg  Ile  Ile
1540                1545                1550 tca  gag  act  tct  aaa  ata  gaa  aca  caa  atc  atg  gat  atc  aag  ccc         4799
Ser  Glu  Thr  Ser  Lys  Ile  Glu  Thr  Gln  Ile  Met  Asp  Ile  Lys  Pro
     1555                1560                1565 aaa  cgt  att  agt  tca  gca  gat  cct  gac  aaa  ctt  caa  act  gaa  cct         4844
Lys  Arg  Ile  Ser  Ser  Ala  Asp  Pro  Asp  Lys  Leu  Gln  Thr  Glu  Pro
1570                1575                1580 cta  tcg  aca  agt  ttt  gaa  att  tcc  aga  aat  aaa  ata  gag  gat  gga         4889
Leu  Ser  Thr  Ser  Phe  Glu  Ile  Ser  Arg  Asn  Lys  Ile  Glu  Asp  Gly
     1585                1590                1595 tct  gta  gtc  ctt  gac  tct  tgt  gaa  gtg  tca  aca  gaa  aat  gat  caa         4934
Ser  Val  Val  Leu  Asp  Ser  Cys  Glu  Val  Ser  Thr  Glu  Asn  Asp  Gln
1600                1605                1610 agc  act  cga  ttt  cca  aaa  cct  gag  tta  gag  att  caa  ttt  aca  cct         4979
Ser  Thr  Arg  Phe  Pro  Lys  Pro  Glu  Leu  Glu  Ile  Gln  Phe  Thr  Pro
     1615                1620                1625 tta  cag  cca  aac  aaa  atg  gca  gtg  aaa  cac  cct  ggt  tgt  acc  aca         5024
Leu  Gln  Pro  Asn  Lys  Met  Ala  Val  Lys  His  Pro  Gly  Cys  Thr  Thr
1630                1635                1640 cca  gtg  aca  gtt  aag  att  ccc  aag  gct  cgg  aag  agg  aag  agt  aat         5069
Pro  Val  Thr  Val  Lys  Ile  Pro  Lys  Ala  Arg  Lys  Arg  Lys  Ser  Asn
     1645                1650                1655 gaa  atg  gag  gag  gac  ttg  gtg  aaa  tgt  gaa  aat  aag  aag  aat  gct         5114
Glu  Met  Glu  Glu  Asp  Leu  Val  Lys  Cys  Glu  Asn  Lys  Lys  Asn  Ala
1660                1665                1670 aca  ccc  aga  act  aat  ttg  aaa  ttt  cct  att  tca  gat  gat  aga  aat         5159
Thr  Pro  Arg  Thr  Asn  Leu  Lys  Phe  Pro  Ile  Ser  Asp  Asp  Arg  Asn
     1675                1680                1685 tct  tct  gtc  aaa  aag  gaa  caa  aag  gtt  gcc  ata  cgt  cca  tca  tct         5204
Ser  Ser  Val  Lys  Lys  Glu  Gln  Lys  Val  Ala  Ile  Arg  Pro  Ser  Ser
1690                1695                1700 aag  aaa  aca  tat  tct  tta  cgg  agt  cag  gca  tcc  ata  att  ggt  gta         5249
Lys  Lys  Thr  Tyr  Ser  Leu  Arg  Ser  Gln  Ala  Ser  Ile  Ile  Gly  Val
     1705                1710                1715 aac  ctg  gcc  act  aag  aaa  aaa  gaa  gga  aca  cta  cag  aaa  ttt  gga         5294
Asn  Leu  Ala  Thr  Lys  Lys  Lys  Glu  Gly  Thr  Leu  Gln  Lys  Phe  Gly
1720                1725                1730 gac  ttc  tta  caa  cat  tct  ccc  tca  att  ctt  caa  tca  aaa  gca  aag         5339
Asp  Phe  Leu  Gln  His  Ser  Pro  Ser  Ile  Leu  Gln  Ser  Lys  Ala  Lys
```

| | | |
|---|---|---|
| aag ata att gaa aca atg agc tct tca aag ctc tca aat gta gaa<br>Lys Ile Ile Glu Thr Met Ser Ser Ser Lys Leu Ser Asn Val Glu<br>1750                         1755                      1760 | | 5384 |
| gca agt aaa gaa aat gtg tct caa cca aaa cga gcc aaa cgg aaa<br>Ala Ser Lys Glu Asn Val Ser Gln Pro Lys Arg Ala Lys Arg Lys<br>1765                         1770                      1775 | | 5429 |
| tta tac aca agt gaa att tca tct cct att gat ata tca ggc caa<br>Leu Tyr Thr Ser Glu Ile Ser Ser Pro Ile Asp Ile Ser Gly Gln<br>1780                         1785                      1790 | | 5474 |
| gtg att tta atg gac cag aaa atg aag gag agt gat cac cag att<br>Val Ile Leu Met Asp Gln Lys Met Lys Glu Ser Asp His Gln Ile<br>1795                         1800                      1805 | | 5519 |
| atc aaa cga cga ctt cga aca aaa aca gcc aaa taa atcacttatg<br>Ile Lys Arg Arg Leu Arg Thr Lys Thr Ala Lys<br>1810                         1815                      1820 | | 5565 |
| gaaatgttta atataaattt tatagtcata gtcattggaa cttgcatcct gtattgtaaa | | 5625 |
| tataaatgta tatattatgc attaaatcac tctgcatata gattgctgtt ttatacatag | | 5685 |
| tataatttta attcaataaa tgagtcaaaa tttgtatatt tttataaggc ttttttataa | | 5745 |
| tagcttcttt caaactgtat ttccctatta tctcagacat tggatcagtg aagatcctag | | 5805 |
| gaaagaggct gttattctca tttattttgc tatacaggat gtaataggtc aggtatttgg | | 5865 |
| tttacttata tttaacaatg tcttatgaat ttttttact ttatctgtta tacaactgat | | 5925 |
| tttacatatc tgtttggatt atagctagga tttggagaat aagtgtgtac agatcacaaa | | 5985 |
| acatgtatat acattattta gaaaagatct caagtcttta attagaatgt ctcacttatt | | 6045 |
| ttgtaaacat tttgtgggta catagtacat gtatatattt acggggtatg tgagatgttt | | 6105 |
| tgacacaggc atgcaatgtg aaatacgtgt atcatggaga atgaggtatc catcccctca | | 6165 |
| agcattttc ctttgaatta cagataatcc aattacattc tttagatcat ttaaaaatat | | 6225 |
| acaagtaagt tattattgat tatagtcact ctattgtgct atcagatagt agatcattct | | 6285 |
| ttttatctta tttgttttg tacccattaa ccatccccac ctcccctgc aaccgtcagt | | 6345 |
| acccttacca gccactggta accattcttc tactctgtat gcccatgagg tcaattgatt | | 6405 |
| ttatttttag atcccataaa taaatgagaa catgcagtct ttgtcaaaaa aaaa | | 6459 |

<210> SEQ ID NO 188
<211> LENGTH: 1820
<212> TYPE: PRT
<213> ORGANISM: Homo sapiens

<400> SEQUENCE: 188

Met Glu Ser Asn Phe Asn Gln Glu Gly Val Pro Arg Pro Ser Tyr Val
1              5                    10                 15

Phe Ser Ala Asp Pro Ile Ala Arg Pro Ser Glu Ile Asn Phe Asp Gly
              20                    25                    30

Ile Lys Leu Asp Leu Ser His Glu Phe Ser Leu Val Ala Pro Asn Thr
        35                    40                    45

Glu Ala Asn Ser Phe Glu Ser Lys Asp Tyr Leu Gln Val Cys Leu Arg
50                    55                    60

Ile Arg Pro Phe Thr Gln Ser Glu Lys Glu Leu Glu Ser Glu Gly Cys
65              70                    75                    80

Val His Ile Leu Asp Ser Gln Thr Val Val Leu Lys Glu Pro Gln Cys
              85                    90                    95

Ile Leu Gly Arg Leu Ser Glu Lys Ser Ser Gly Gln Met Ala Gln Lys

```
                100                 105                 110
Phe Ser Phe Ser Lys Val Phe Gly Pro Ala Thr Thr Gln Lys Glu Phe
        115                 120                 125
Phe Gln Gly Cys Ile Met Gln Pro Val Lys Asp Leu Leu Lys Gly Gln
        130                 135                 140
Ser Arg Leu Ile Phe Thr Tyr Gly Leu Thr Asn Ser Gly Lys Thr Tyr
145                 150                 155                 160
Thr Phe Gln Gly Thr Glu Glu Asn Ile Gly Ile Leu Pro Arg Thr Leu
                165                 170                 175
Asn Val Leu Phe Asp Ser Leu Gln Glu Arg Leu Tyr Thr Lys Met Asn
                180                 185                 190
Leu Lys Pro His Arg Ser Arg Glu Tyr Leu Arg Leu Ser Ser Glu Gln
        195                 200                 205
Glu Lys Glu Glu Ile Ala Ser Lys Ser Ala Leu Leu Arg Gln Ile Lys
        210                 215                 220
Glu Val Thr Val His Asn Asp Ser Asp Asp Thr Leu Tyr Gly Ser Leu
225                 230                 235                 240
Thr Asn Ser Leu Asn Ile Ser Glu Phe Glu Glu Ser Ile Lys Asp Tyr
                245                 250                 255
Glu Gln Ala Asn Leu Asn Met Ala Asn Ser Ile Lys Phe Ser Val Trp
        260                 265                 270
Val Ser Phe Phe Glu Ile Tyr Asn Glu Tyr Ile Tyr Asp Leu Phe Val
        275                 280                 285
Pro Val Ser Ser Lys Phe Gln Lys Arg Lys Met Leu Arg Leu Ser Gln
        290                 295                 300
Asp Val Lys Gly Tyr Ser Phe Ile Lys Asp Leu Gln Trp Ile Gln Val
305                 310                 315                 320
Ser Asp Ser Lys Glu Ala Tyr Arg Leu Leu Lys Leu Gly Ile Lys His
                325                 330                 335
Gln Ser Val Ala Phe Thr Lys Leu Asn Asn Ala Ser Ser Arg Ser His
                340                 345                 350
Ser Ile Phe Thr Val Lys Ile Leu Gln Ile Glu Asp Ser Glu Met Ser
        355                 360                 365
Arg Val Ile Arg Val Ser Glu Leu Ser Leu Cys Asp Leu Ala Gly Ser
        370                 375                 380
Glu Arg Thr Met Lys Thr Gln Asn Glu Gly Glu Arg Leu Arg Glu Thr
385                 390                 395                 400
Gly Asn Ile Asn Thr Ser Leu Leu Thr Leu Gly Lys Cys Ile Asn Val
                405                 410                 415
Leu Lys Asn Ser Glu Lys Ser Lys Phe Gln Gln His Val Pro Phe Arg
                420                 425                 430
Glu Ser Lys Leu Thr His Tyr Phe Gln Ser Phe Asn Gly Lys Gly
        435                 440                 445
Lys Ile Cys Met Ile Val Asn Ile Ser Gln Cys Tyr Leu Ala Tyr Asp
        450                 455                 460
Glu Thr Leu Asn Val Leu Lys Phe Ser Ala Ile Ala Gln Lys Val Cys
465                 470                 475                 480
Val Pro Asp Thr Leu Asn Ser Ser Gln Glu Lys Leu Phe Gly Pro Val
                485                 490                 495
Lys Ser Ser Gln Asp Val Ser Leu Asp Ser Asn Ser Asn Ser Lys Ile
                500                 505                 510
Leu Asn Val Lys Arg Ala Thr Ile Ser Trp Glu Asn Ser Leu Glu Asp
        515                 520                 525
```

```
Leu Met Glu Asp Glu Asp Leu Val Glu Glu Leu Glu Asn Ala Glu Glu
    530             535                 540

Thr Gln Asn Val Glu Thr Lys Leu Leu Asp Glu Asp Leu Asp Lys Thr
545                 550                 555                 560

Leu Glu Glu Asn Lys Ala Phe Ile Ser His Glu Glu Lys Arg Lys Leu
                565                 570                 575

Leu Asp Leu Ile Glu Asp Leu Lys Lys Lys Leu Ile Asn Glu Lys Lys
                580                 585                 590

Glu Lys Leu Thr Leu Glu Phe Lys Ile Arg Glu Glu Val Thr Gln Glu
            595                 600                 605

Phe Thr Gln Tyr Trp Ala Gln Arg Glu Ala Asp Phe Lys Glu Thr Leu
    610                 615                 620

Leu Gln Glu Arg Glu Ile Leu Glu Glu Asn Ala Glu Arg Arg Leu Ala
625                 630                 635                 640

Ile Phe Lys Asp Leu Val Gly Lys Cys Asp Thr Arg Glu Glu Ala Ala
                645                 650                 655

Lys Asp Ile Cys Ala Thr Lys Val Glu Thr Glu Glu Thr His Asn Tyr
                660                 665                 670

Val Gly Phe Glu Asp Ile Ile Asp Ser Leu Gln Asp Asn Val Ala Asp
            675                 680                 685

Ile Lys Lys Gln Ala Glu Ile Ala His Leu Tyr Ile Ala Ser Leu Pro
    690                 695                 700

Asp Pro Gln Glu Ala Thr Ala Cys Leu Glu Leu Lys Phe Asn Gln Ile
705                 710                 715                 720

Lys Ala Glu Leu Ala Lys Thr Lys Gly Glu Leu Ile Lys Thr Lys Glu
                725                 730                 735

Glu Leu Lys Lys Arg Glu Asn Glu Ser Asp Ser Leu Ile Gln Glu Leu
            740                 745                 750

Glu Thr Ser Asn Lys Lys Ile Ile Thr Gln Asn Gln Arg Ile Lys Glu
    755                 760                 765

Leu Ile Asn Ile Ile Asp Gln Lys Glu Asp Thr Ile Asn Glu Phe Gln
770                 775                 780

Asn Leu Lys Ser His Met Glu Asn Thr Phe Lys Cys Asn Asp Lys Ala
785                 790                 795                 800

Asp Thr Ser Ser Leu Ile Ile Asn Asn Lys Leu Ile Cys Asn Glu Thr
                805                 810                 815

Val Glu Val Pro Lys Asp Ser Lys Ser Lys Ile Cys Ser Glu Arg Lys
            820                 825                 830

Arg Val Asn Glu Asn Glu Leu Gln Gln Asp Glu Pro Pro Ala Lys Lys
    835                 840                 845

Gly Ser Ile His Val Ser Ser Ala Ile Thr Glu Asp Gln Lys Lys Ser
850                 855                 860

Glu Glu Val Arg Pro Asn Ile Ala Glu Ile Glu Asp Ile Arg Val Leu
865                 870                 875                 880

Gln Glu Asn Asn Glu Gly Leu Arg Ala Phe Leu Thr Ile Glu Asn
                885                 890                 895

Glu Leu Lys Asn Glu Lys Glu Glu Lys Ala Glu Leu Asn Lys Gln Ile
            900                 905                 910

Val His Phe Gln Gln Glu Leu Ser Leu Ser Glu Lys Lys Asn Leu Thr
    915                 920                 925

Leu Ser Lys Glu Val Gln Gln Ile Gln Ser Asn Tyr Asp Ile Ala Ile
930                 935                 940
```

-continued

```
Ala Glu Leu His Val Gln Lys Ser Lys Asn Gln Gln Glu Lys
945                 950                 955                 960

Ile Met Lys Leu Ser Asn Glu Ile Glu Thr Ala Thr Arg Ser Ile Thr
            965                 970                 975

Asn Asn Val Ser Gln Ile Lys Leu Met His Thr Lys Ile Asp Glu Leu
            980                 985                 990

Arg Thr Leu Asp Ser Val Ser Gln Ile Ser Asn Ile Asp Leu Leu Asn
            995                 1000                1005

Leu Arg Asp Leu Ser Asn Gly Ser Glu Glu Asp Asn Leu Pro Asn
        1010                1015                1020

Thr Gln Leu Asp Leu Leu Gly Asn Asp Tyr Leu Val Ser Lys Gln
        1025                1030                1035

Val Lys Glu Tyr Arg Ile Gln Glu Pro Asn Arg Glu Asn Ser Phe
        1040                1045                1050

His Ser Ser Ile Glu Ala Ile Trp Glu Glu Cys Lys Glu Ile Val
        1055                1060                1065

Lys Ala Ser Ser Lys Lys Ser His Gln Ile Glu Glu Leu Glu Gln
        1070                1075                1080

Gln Ile Glu Lys Leu Gln Ala Glu Val Lys Gly Tyr Lys Asp Glu
        1085                1090                1095

Asn Asn Arg Leu Lys Glu Lys Glu His Lys Asn Gln Asp Asp Leu
        1100                1105                1110

Leu Lys Glu Lys Glu Thr Leu Ile Gln Gln Leu Lys Glu Glu Leu
        1115                1120                1125

Gln Glu Lys Asn Val Thr Leu Asp Val Gln Ile Gln His Val Val
        1130                1135                1140

Glu Gly Lys Arg Ala Leu Ser Glu Leu Thr Gln Gly Val Thr Cys
        1145                1150                1155

Tyr Lys Ala Lys Ile Lys Glu Leu Glu Thr Ile Leu Glu Thr Gln
        1160                1165                1170

Lys Val Glu Cys Ser His Ser Ala Lys Leu Glu Gln Asp Ile Leu
        1175                1180                1185

Glu Lys Glu Ser Ile Ile Leu Lys Leu Glu Arg Asn Leu Lys Glu
        1190                1195                1200

Phe Gln Glu His Leu Gln Asp Ser Val Lys Asn Thr Lys Asp Leu
        1205                1210                1215

Asn Val Lys Glu Leu Lys Leu Lys Glu Glu Ile Thr Gln Leu Thr
        1220                1225                1230

Asn Asn Leu Gln Asp Met Lys His Leu Leu Gln Leu Lys Glu Glu
        1235                1240                1245

Glu Glu Glu Thr Asn Arg Gln Glu Thr Glu Lys Leu Lys Glu Glu
        1250                1255                1260

Leu Ser Ala Ser Ser Ala Arg Thr Gln Asn Leu Lys Ala Asp Leu
        1265                1270                1275

Gln Arg Lys Glu Glu Asp Tyr Ala Asp Leu Lys Glu Lys Leu Thr
        1280                1285                1290

Asp Ala Lys Lys Gln Ile Lys Gln Val Gln Lys Glu Val Ser Val
        1295                1300                1305

Met Arg Asp Glu Asp Lys Leu Leu Arg Ile Lys Ile Asn Glu Leu
        1310                1315                1320

Glu Lys Lys Lys Asn Gln Cys Ser Gln Glu Leu Asp Met Lys Gln
        1325                1330                1335

Arg Thr Ile Gln Gln Leu Lys Glu Gln Leu Asn Asn Gln Lys Val
```

```
              1340                1345                1350
    Glu  Glu  Ala  Ile  Gln  Gln  Tyr  Glu  Arg  Ala  Cys  Lys  Asp  Leu  Asn
              1355                1360                1365

Val  Lys  Glu  Lys  Ile  Ile  Glu  Asp  Met  Arg  Met  Thr  Leu  Glu  Glu
              1370                1375                1380

Gln  Glu  Gln  Thr  Gln  Val  Glu  Gln  Asp  Gln  Val  Leu  Glu  Ala  Lys
              1385                1390                1395

Leu  Glu  Glu  Val  Glu  Arg  Leu  Ala  Thr  Glu  Leu  Glu  Lys  Trp  Lys
              1400                1405                1410

Glu  Lys  Cys  Asn  Asp  Leu  Glu  Thr  Lys  Asn  Asn  Gln  Arg  Ser  Asn
              1415                1420                1425

Lys  Glu  His  Glu  Asn  Asn  Thr  Asp  Val  Leu  Gly  Lys  Leu  Thr  Asn
              1430                1435                1440

Leu  Gln  Asp  Glu  Leu  Gln  Glu  Ser  Glu  Gln  Lys  Tyr  Asn  Ala  Asp
              1445                1450                1455

Arg  Lys  Lys  Trp  Leu  Glu  Glu  Lys  Met  Met  Leu  Ile  Thr  Gln  Ala
              1460                1465                1470

Lys  Glu  Ala  Glu  Asn  Ile  Arg  Asn  Lys  Glu  Met  Lys  Lys  Tyr  Ala
              1475                1480                1485

Glu  Asp  Arg  Glu  Arg  Phe  Phe  Lys  Gln  Gln  Asn  Glu  Met  Glu  Ile
              1490                1495                1500

Leu  Thr  Ala  Gln  Leu  Thr  Glu  Lys  Asp  Ser  Asp  Leu  Gln  Lys  Trp
              1505                1510                1515

Arg  Glu  Glu  Arg  Asp  Gln  Leu  Val  Ala  Ala  Leu  Glu  Ile  Gln  Leu
              1520                1525                1530

Lys  Ala  Leu  Ile  Ser  Ser  Asn  Val  Gln  Lys  Asp  Asn  Glu  Ile  Glu
              1535                1540                1545

Gln  Leu  Lys  Arg  Ile  Ile  Ser  Glu  Thr  Ser  Lys  Ile  Glu  Thr  Gln
              1550                1555                1560

Ile  Met  Asp  Ile  Lys  Pro  Lys  Arg  Ile  Ser  Ser  Ala  Asp  Pro  Asp
              1565                1570                1575

Lys  Leu  Gln  Thr  Glu  Pro  Leu  Ser  Thr  Ser  Phe  Glu  Ile  Ser  Arg
              1580                1585                1590

Asn  Lys  Ile  Glu  Asp  Gly  Ser  Val  Val  Leu  Asp  Ser  Cys  Glu  Val
              1595                1600                1605

Ser  Thr  Glu  Asn  Asp  Gln  Ser  Thr  Arg  Phe  Pro  Lys  Pro  Glu  Leu
              1610                1615                1620

Glu  Ile  Gln  Phe  Thr  Pro  Leu  Gln  Pro  Asn  Lys  Met  Ala  Val  Lys
              1625                1630                1635

His  Pro  Gly  Cys  Thr  Thr  Pro  Val  Thr  Val  Lys  Ile  Pro  Lys  Ala
              1640                1645                1650

Arg  Lys  Arg  Lys  Ser  Asn  Glu  Met  Glu  Glu  Asp  Leu  Val  Lys  Cys
              1655                1660                1665

Glu  Asn  Lys  Lys  Asn  Ala  Thr  Pro  Arg  Thr  Asn  Leu  Lys  Phe  Pro
              1670                1675                1680

Ile  Ser  Asp  Asp  Arg  Asn  Ser  Ser  Val  Lys  Lys  Glu  Gln  Lys  Val
              1685                1690                1695

Ala  Ile  Arg  Pro  Ser  Ser  Lys  Lys  Thr  Tyr  Ser  Leu  Arg  Ser  Gln
              1700                1705                1710

Ala  Ser  Ile  Ile  Gly  Val  Asn  Leu  Ala  Thr  Lys  Lys  Lys  Glu  Gly
              1715                1720                1725

Thr  Leu  Gln  Lys  Phe  Gly  Asp  Phe  Leu  Gln  His  Ser  Pro  Ser  Ile
              1730                1735                1740
```

```
Leu Gln Ser Lys Ala Lys Lys Ile Ile Glu Thr Met Ser Ser Ser
    1745            1750                1755

Lys Leu Ser Asn Val Glu Ala Ser Lys Glu Asn Val Ser Gln Pro
    1760            1765                1770

Lys Arg Ala Lys Arg Lys Leu Tyr Thr Ser Glu Ile Ser Ser Pro
    1775            1780                1785

Ile Asp Ile Ser Gly Gln Val Ile Leu Met Asp Gln Lys Met Lys
    1790            1795                1800

Glu Ser Asp His Gln Ile Ile Lys Arg Arg Leu Arg Thr Lys Thr
    1805            1810                1815

Ala Lys
    1820

<210> SEQ ID NO 189
<211> LENGTH: 4
<212> TYPE: PRT
<213> ORGANISM: Artificial Sequence
<220> FEATURE:
<223> OTHER INFORMATION: a linker peptide

<400> SEQUENCE: 189

Asn Lys Arg Lys
1
```